US011014940B1

(12) United States Patent
Traverse et al.

(10) Patent No.: US 11,014,940 B1
(45) Date of Patent: May 25, 2021

(54) THIAZOLIDINONE AND OXAZOLIDINONE COMPOUNDS AND FORMULATIONS

(71) Applicant: Celgene Corporation, Summit, NJ (US)

(72) Inventors: John Fitzgerald Traverse, Lebanon, NJ (US); Sanjeevani Ghone, Plainsboro, NJ (US); Fu-An Kang, Collegeville, PA (US); Francisco Velazquez, Clinton, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 16/653,223

(22) Filed: Oct. 15, 2019

Related U.S. Application Data

(60) Provisional application No. 62/746,312, filed on Oct. 16, 2018.

(51) Int. Cl.
| | | |
|---|---|---|
| C07D 513/10 | (2006.01) | |
| A61K 31/426 | (2006.01) | |
| C07D 277/54 | (2006.01) | |
| C07D 277/34 | (2006.01) | |

(52) U.S. Cl.
CPC ......... C07D 513/10 (2013.01); C07D 277/34 (2013.01); C07D 277/54 (2013.01)

(58) Field of Classification Search
None
See application file for complete search history.

(56) References Cited

U.S. PATENT DOCUMENTS

| | | |
|---|---|---|
| 7,435,828 B2 | 10/2008 | Binkert et al. |
| 8,263,780 B2 | 9/2012 | Abele et al. |
| 8,273,779 B2 | 9/2012 | Binkert et al. |
| RE43,728 E | 10/2012 | Binkert et al. |
| 8,399,514 B2 | 3/2013 | Lukashev et al. |
| 8,524,752 B2 | 9/2013 | Binkert et al. |
| 8,785,484 B2 | 7/2014 | Brossard et al. |
| 8,912,340 B2 | 12/2014 | Abele et al. |
| 9,000,018 B2 | 4/2015 | Binkert et al. |
| 9,062,014 B2 | 6/2015 | Bonham et al. |
| 9,340,518 B2 | 5/2016 | Herse |
| 2014/0303217 A1 | 10/2014 | Brossard et al. |
| 2014/0316140 A1 | 10/2014 | Brossard et al. |

FOREIGN PATENT DOCUMENTS

| | | |
|---|---|---|
| EP | 2 316 430 B1 | 6/2012 |
| WO | WO 2005/054215 A1 | 6/2005 |
| WO | WO 2005/123677 A1 | 12/2005 |
| WO | WO 2006/010379 A1 | 2/2006 |
| WO | WO 2006/010544 A2 | 2/2006 |
| WO | WO 2006/100633 A1 | 9/2006 |
| WO | WO 2006/100635 A2 | 9/2006 |
| WO | WO 2007/080542 A1 | 7/2007 |
| WO | WO 2008/029306 A2 | 3/2008 |
| WO | WO 2008/062376 A2 | 5/2008 |
| WO | WO 2008/097596 A2 | 8/2008 |
| WO | WO 2008/114157 A1 | 9/2008 |
| WO | WO 2009/024905 A1 | 2/2009 |
| WO | WO 2009/074950 A2 | 6/2009 |
| WO | WO 2009/115954 A1 | 9/2009 |
| WO | WO 2010/046835 A1 | 4/2010 |
| WO | WO 2011/007324 A1 | 1/2011 |
| WO | WO 2013/184888 A1 | 12/2013 |
| WO | WO 2014/027330 A1 | 2/2014 |
| WO | WO 2016/091996 A1 | 6/2016 |
| WO | WO 2016/092042 A1 | 6/2016 |
| WO | WO 2017/107972 A1 | 6/2017 |
| WO | WO 2018/167030 A1 | 9/2018 |
| WO | WO 2019/060147 A1 | 3/2019 |

OTHER PUBLICATIONS

Soderberg, Tim, Organic Chemistry With a Biological Emphasis (University of Minnesota, Morris), https://chem.libretexts.org/@go/page/35194, Aug. 13, 2020, pp. 1-2.*
Boehler et al., "Absolute Bioavailability of Ponesimod, a Selective S1P 1 Receptor Modulator, in Healthy Male Subjects," *Eur J Drug Metab Pharmacokinet.*, 42(1):129-134 (2017).
Bolli et al., "2-imino-thiazolidin-4-one Derivatives as Potent, Orally Active S1P1 Receptor Agonists," J Med Chem.;53(10):4198-4211 (2010).
Brossard et al., "Multiple-dose Tolerability, Pharmacokinetics, and Pharmacodynamics of Ponesimod, an S1P1 Receptor Modulator: Favorable Impact of Dose Up-Titration," *J. Clin. Pharmacol.*, 54(2):179-188 (2014).
D'Ambrosio et al., *Immunopharmacol Immunotoxicol.* 37(1):103-109. (2015).
D'Ambrosio et al., "Ponesimod, a Selective S1P1 Receptor Modulator: A Potential Treatment for Multiple Sclerosis and Other Immune-Mediated Diseases," *Ther. Adv. Chronic. Dis.*, 7(1):18-33 (2016).
Guerard et al., "Effect of Hepatic or Renal Impairment on the Pharmacokinetics, Safety, and Tolerability of Ponesimod, a Selective S1P1 Receptor Modulator," *Basic Clin. Pharmacol. Toxicol.*, 118(5):356-368 (2016).
Hoch et al., "Effect of Ponesimod, a Selective S1P1 Receptor Modulator, on the QT Interval in Healthy Individuals," *Basic Clin. Pharmacol. Toxicol.*, 116(5): 429-437 (2015).
Hoch et al., "Clinical Pharmacology of Ponesimod, a Selective $S1P_1$ Receptor Modulator, After Uptitration to Supratherapeutic Doses in Healthy Subjects," *Eur. J. Pharm. Sci.*, 63:147-153 (2014).

(Continued)

*Primary Examiner* — Samantha L Shterengarts
(74) *Attorney, Agent, or Firm* — Jones Day

(57) ABSTRACT

Provided herein are thiazolidinone and oxazolidinone compounds such as Compound 1, 1A, 1B, 1C, 1D, 1E, 1F, and compounds of Formulas (I), (II), (III), and (IV). Also provided herein are uses of these thiazolidinone and oxazolidinone compounds such as Compound 1, 1A, 1B, 1C, 1D, 1E, 1F, and compounds of Formulas (I), (II), (III), and (IV), pharmaceutical compositions and formulations in the treatment of various diseases, including but not limited to diseases or disorders associated with an activated immune system (e.g., multiple sclerosis and psoriasis).

24 Claims, No Drawings

(56) References Cited

OTHER PUBLICATIONS

Juif et al., "Biocomparison of three formulations of the S1P receptor modulator ponesimod in healthy subjects," *Drugs R D.* 15(2):203-210 (2015).

Juif et al., "Clinical Pharmacology, Efficacy, and Safety Aspects of sphingosine-1-phosphate Receptor Modulators,"*Expert Opin Drug Metab Toxicol.* 12(8):879-895 (2016).

Juif et al., "Mitigation of Initial Cardiodynamic Effects of the S1P 1 Receptor Modulator Ponesimod Using a Novel Up-Titration Regimen," *J. Clin. Pharmacol.*, 57(3):401-410 (2017).

Jurcevic et al., "Effects of Multiple-Dose Ponesimod, a Selective S1P 1 Receptor Modulator, on Lymphocyte Subsets in Healthy Humans," *Drug Des. Devel Ther.*, 11:123-131 (2016).

Krause et al., "Population Pharmacokinetics and Pharmacodynamics of Ponesimod, a Selective S1P1 Receptor Modulator," J *Pharmacokinet Pharmacodyn.*, 41(3):261-278 (2014).

Lott et al., "Impact of Demographics, Organ Impairment, Disease, Formulation, and Food on the Pharmacokinetics of the Selective S1P 1 Receptor Modulator Ponesimod Based on 13 Clinical Studies," *Clin. Pharmacokinet.*, 56(4):395-408 (2017).

Lott et al., "Population Pharmacokinetics of Ponesimod and Its Primary Metabolites in Healthy and Organ-Impaired Subjects," *Eur J Pharm Sci.*,89:83-93 (2016).

Lott et al., Pharm Res.;34(3):599-609 (2017).

NCT01006265: Clinical Study to Evaluate the Efficacy, Safety, and Tolerability of ACT-128800 in Patients With Relapsing-remitting Multiple Sclerosis. https://clinicaltrials.gov/ct2/show/NCT01006265. First posted Nov. 1, 2009; last update posted Apr. 4, 2017; downloaded May 28, 2020.

NCT01093326: Clinical Study to Investigate the Long-term Safety, Tolerability, and Efficacy of Ponesimod in Patients With Relapsing-remitting Multiple Sclerosis. https://clinicaltrials.gov/ct2/show/NCT01093326?term=NCT01093326&draw=2&rank=1. Fist posted Mar. 25, 2010; last updated posted May 21, 2020; downloaded May 28, 2020.

NCT01755871: Long-term Effect of Fingolimod on Circulating Immunocompetent Mononuclear Cells in Patients With Multiple Sclerosis (terminated). https://clinicaltrials.gov/ct2/show/NCT01755871?term=NCT01755871&draw=2&rank=1. First posted Dec. 24, 2012; Last Update Posted Jun. 9, 2016; downloaded May 28, 2020.

NCT02029482: Study to Investigate the Safety, Tolerability, Pharmacokinetics, and Pharmacodynamics of ACT-128800 in Healthy Subjects. https://clinicaltrials.gov/ct2/show/NCT02029482?term=NCT02029482&draw=2&rank=1. First Posted Jan. 8, 2014; Last Update Posted Jan. 8, 2014; downloaded May 28, 2020.

NCT02068235: Study to Investigate the Absolute Bioavailability of a Single Oral Dose of Ponesimod in Healthy Male Subjects. https://clinicaltrials.gov/ct2/show/NCT02068235?term=NCT02068235&draw=2&rank=1. First Posted Feb. 21, 2014; Last Update Posted May 21, 2015; downloaded May 28, 2020.

NCT02126956: Mass Balance, Pharmacokinetics, and Metabolism of 14C-labeled ACT-128800 Administered to Healthy Male Subjects. https://clinicaltrials.gov/ct2/show/NCT02126956?term=NCT02126956&draw=2&rank=1. First Posted Apr. 30, 2014; Late Update Posted Apr. 30, 2014; downloaded May 28, 2020.

NCT02136888: Study of the Electrocardiographic Effects of Ponesimod in Healthy Male and Female Subjects. https://clinicaltrials.gov/ct2/show/NCT02136888?term=NCT02136888&draw=2&rank=1. First Posted May 13, 2014; Last Update Posted May 13, 2014; downloaded May 28, 2020.

NCT02223832: Study to Evaluate the Pharmacokinetics, Tolerability, and Safety of ACT-128800 in Japanese and Caucasian Healthy Male and Female Subjects. https://clinicaltrials.gov/ct2/show/NCT02223832?term=NCT02223832&draw=2&rank=1. First Posted Aug. 22, 2014; Last Update Posted Aug. 22, 2014; downloaded May 22, 2020.

NCT02425644: Oral Ponesimod Versus Teriflunomide in Relapsing MUltiple Sclerosis (OPTIMUM). https://clinicaltrials.gov/ct2/show/NCT02425644?term=NCT02425644&draw=2&rank=1. First Posted Apr. 24, 2015; Last Update Posted May 27, 2020; downloaded May 28, 2020.

NCT02461134: Clinical Study to Investigate the Biological Activity, Safety, Tolerability, and Pharmacokinetics of Ponesimod in Subjects With Symptomatic Chronic Gvhd (terminated). https://clinicaltrials.gov/ct2/show/NCT02461134?term=NCT02461134&draw=2&rank=1. First Posted Jun. 3, 2015; Last Update Posted May 9, 2018; downloaded May 28, 2020.

NCT02907177: Clinical Study to Compare the Efficacy and Safety of Ponesimod to Placebo in Subjects With Active Relapsing Multiple Sclerosis Who Are Treated With Dimethyl Fumarate (Tecfidera®). https://clinicaltrials.gov/ct2/show/NCT02907177?term=NCT02907177&draw=2&rank=1. First Posted Sep. 20, 2016; Last Update Posted Apr. 6, 2020; downloaded May 28, 2020.

Olsson et al., "Oral Ponesimod in Relapsing-Remitting Multiple Sclerosis: A Randomised Phase II Trial," *Neuro.l Neurosurg. Psychiatry.*, 85(11):1198-1208 (2014).

Piali et al., "The Selective Sphingosine 1-phosphate Receptor 1 Agonist Ponesimod Protects Against Lymphocyte-Mediated Tissue Inflammation," *J. Pharmacol. Exp. Ther.*, 337(2):547-556 (2011).

Rey et al., "Desensitization by Progressive Up-Titration Prevents First-Dose Effects on the Heart: Guinea Pig Study With Ponesimod, a Selective S1P1 Receptor Modulator," *PLoS One.*, 8(9):e74285 (2013).

Reyes et al., "Effects of Ethnicity and Sex on the Pharmacokinetics and Pharmacodynamics of the Selective sphingosine-1-phosphate Receptor 1 Modulator Ponesimod: A Clinical Study in Japanese and Caucasian Subjects," *Pharmacology*, 94(5-6): 223-229 (2014).

Reyes et al., "Mass Balance, Pharmacokinetics and Metabolism of the Selective S1P1 Receptor Modulator Ponesimod in Humans," *Xenobiotica.*, 45(2):139-149 (2015).

Scherz et al. "Three Different Up-Titration Regimens of Ponesimod, an S1P1 Receptor Modulator, in Healthy Subjects," *J. Clin. Pharmacol.*, 55(6):688-697 (2015).

\* cited by examiner

THIAZOLIDINONE AND OXAZOLIDINONE COMPOUNDS AND FORMULATIONS

This application claims priority to U.S. Provisional Application No. 62/746,312, filed Oct. 16, 2018, the entirety of which is incorporated herein by reference.

1 FIELD

Provided herein are thiazolidinone and oxazolidinone compounds of Compound 1, Compounds 1A-1F, and Formulas (I), (II), (III), and (IV). Also provided herein are uses of Compound 1, Compounds 1A-1F, and compounds of Formulas (I), (II), (III), and (IV) and pharmaceutical compositions and formulations comprising the same in the treatment of various diseases, including but not limited to diseases or disorders associated with an activated immune system (e.g., multiple sclerosis and psoriasis).

2 BACKGROUND

When the immune system functions normally, it produces a response intended to protect against harmful or foreign substances such as bacteria, parasites, and cancerous cells. Autoimmune diseases arise when the immune system attacks one or more of the body's normal constituents as if they were a foreign substance. These attacks cause inflammation and tissue damage that may lead to autoimmune disorders. There are more than 80 diseases that occur as a result of the body's autoimmune response to various harmful or foreign substances, affecting more than 23.5 million people in the United States. Some of the most common types of autoimmune diseases include multiple sclerosis, and psoriasis.

Multiple Sclerosis ("MS") is an autoimmune disease of the central nervous system ("CNS"); characterized by degeneration of the protective sheath ("myelin") that covers nerve fibers in the brain and spinal cord. More than 2.5 million people in the world suffer from MS, and it is the most common neurologic, disabling disease in young adults. Diagnosis is generally made between 15 and 50 years of age, with symptoms either occurring in recurring, isolated attacks (i.e., relapsing forms) or symptoms increasing over time (i.e., progressive forms). Permanent neurological dysfunction can result from incomplete recovery from acute relapses or as a consequence of slow progression of disability.

3 SUMMARY

In one aspect, provided herein is a compound selected from the group consisting of:
5-(3-chloro-4-(2,3-dihydroxypropoxy)benzylidene)-3-(o-tolyl)thiazolidine-2,4-dione (Compound 1);
±(Z)-5-(3-chloro-4-(2,3-dihydroxypropoxy)benzylidene)-3-(o-tolyl)thiazolidine-2,4-dione (Compound 1A);
(R,Z)-5-(3-chloro-4-(2,3-dihydroxypropoxy)benzylidene)-3-(o-tolyl)thiazolidine-2,4-dione (Compound 1B);
(S,Z)-5-(3-chloro-4-(2,3-dihydroxypropoxy)benzylidene)-3-(o-tolyl)thiazolidine-2,4-dione (Compound 1C);
±(E)-5-(3-chloro-4-(2,3-dihydroxypropoxy)benzylidene)-3-(o-tolyl)thiazolidine-2,4-dione (Compound 1D);
(R,E)-5-(3-chloro-4-(2,3-dihydroxypropoxy)benzylidene)-3-(o-tolyl)thiazolidine-2,4-dione (Compound 1E); and
(S,E)-5-(3-chloro-4-(2,3-dihydroxypropoxy)benzylidene)-3-(o-tolyl)thiazolidine-2,4-dione (Compound 1F);
or a pharmaceutically acceptable salt, hydrate, or solvate thereof.

In another aspect, provided herein are compounds of Formula (IA) or Formula (IB):

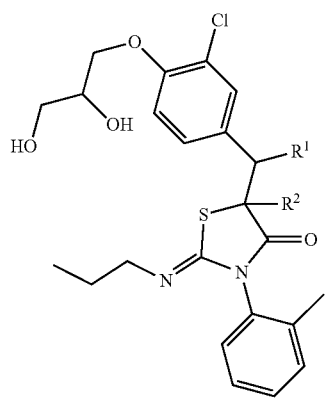

Formula (IA)

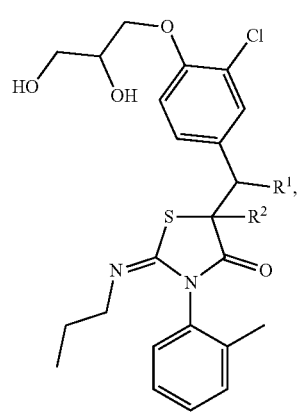

Formula (IB)

or a pharmaceutically acceptable salt, hydrate, or solvate thereof, wherein:

$R^1$ is =O or —OH; and $R^2$ is —H; or wherein $R^1$ and $R^2$ combine to form an epoxide ring with the carbon atoms to which they are attached.

In another aspect, provided herein are compounds of Formula (IIA), Formula (IIB), Formula (IIC), or Formula (IID):

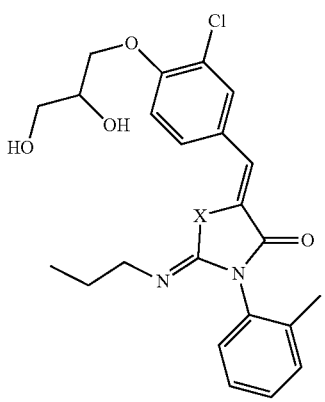

Formula (IIA)

Formula (IIB)
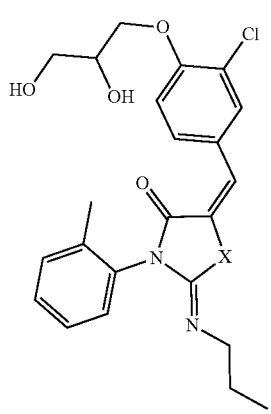
Formula (IIC)
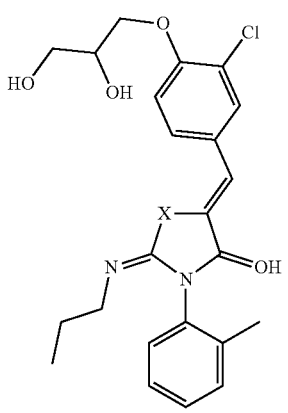
Formula (IID)
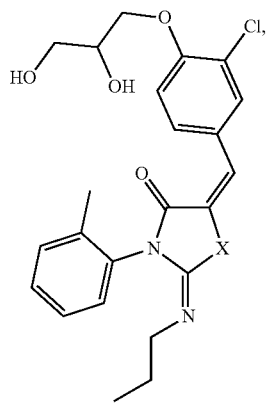
or a pharmaceutically acceptable salt, hydrate, or solvate thereof, wherein:
X is —O— or —S(O)—.
In another aspect, provided herein are compounds of Formula (IIIA), Formula (IIIB), Formula (IIIC), or Formula (IIID):
Formula (IIIA)
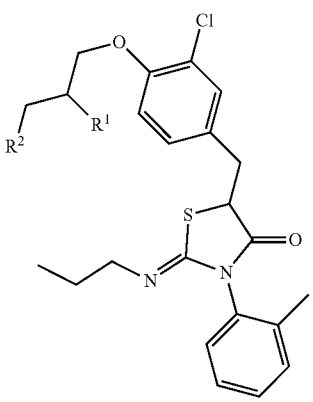
Formula (IIIB)
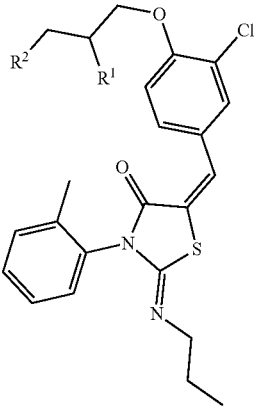
Formula (IIIC)
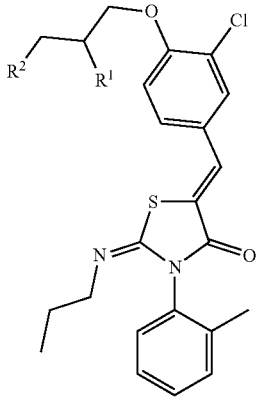
Formula (IIID)
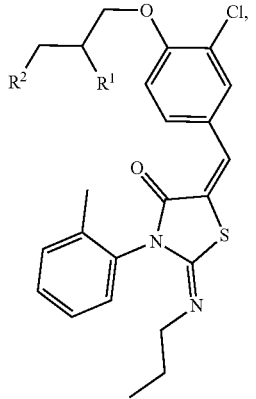

or a pharmaceutically acceptable salt, hydrate, or solvate thereof, wherein:
one of $R^1$ or $R^2$ is —OH and the other of $R^1$ or $R^2$ is =O.
In another aspect, provided herein are compounds of Formula (IVA), Formula (IVB), Formula (IVC), Formula (IVD), Formula (IVE), Formula (IVF), Formula (IVG), or Formula (IVH):
Formula (IVA)
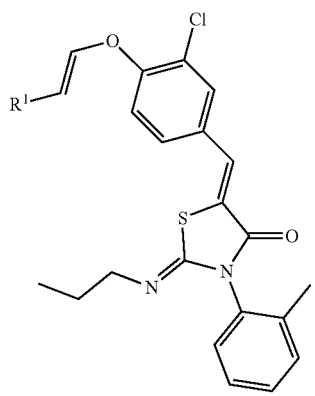
Formula (IVB)
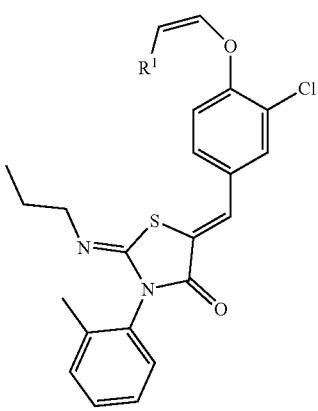
Formula (IVC)
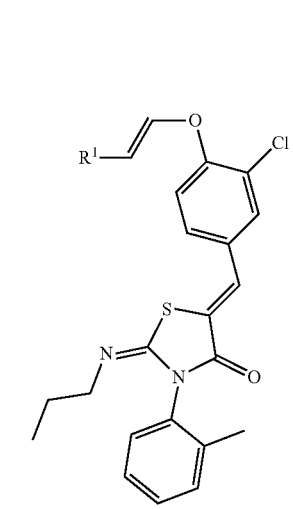
Formula (IVD)
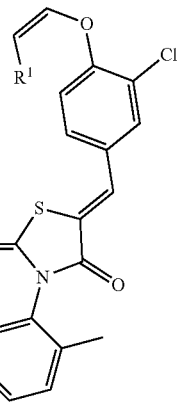
Formula (IVE)
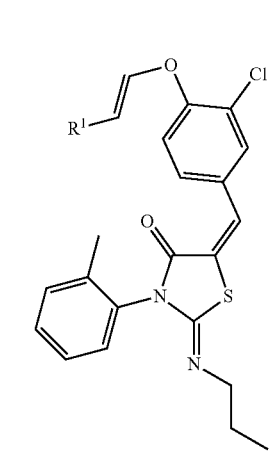
Formula (IVF)
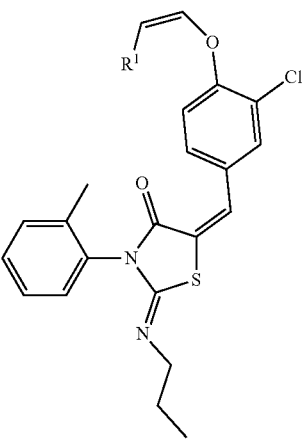

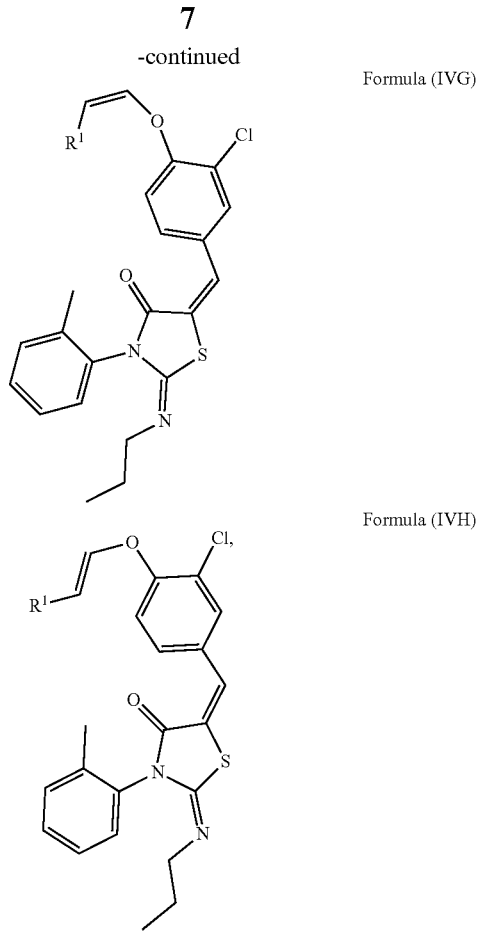

Formula (IVG)

Formula (IVH)

or a pharmaceutically acceptable salt, hydrate, or solvate thereof, wherein:
$R^1$ is —C(O)H or —C(O)OH.

In certain embodiments, provided herein are pharmaceutical compositions comprising at least one of Compound 1, 1A, 1B, 1C, 1D, 1E, 1F, a compound of Formula (I), (II), (III), or (IV), or a pharmaceutically acceptable salt, hydrate, or solvate thereof; and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, provided herein are pharmaceutical formulations comprising at least one of Compound 1, 1A, 1B, 1C, 1D, 1E, 1F, a compound of Formula (I), (II), (III), or (IV), or a pharmaceutically acceptable salt, hydrate, or solvate thereof; and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof; and a pharmaceutically acceptable carrier.

In certain embodiments, provided herein is a method of treating multiple sclerosis comprising administering to a patient in need thereof a therapeutically effective amount of the compounds described herein.

In certain embodiments, provided herein is a method of treating multiple sclerosis comprising administering to a patient in need thereof a therapeutically effective amount of the pharmaceutical compositions described herein.

In certain embodiments, provided herein is a method of treating multiple sclerosis comprising administering to a patient in need thereof a therapeutically effective amount of the pharmaceutical formulations described herein.

In certain embodiments, provided herein is a method of treating psoriasis comprising administering to a patient in need thereof a therapeutically effective amount of the compounds described herein.

In certain embodiments, provided herein is a method of treating psoriasis comprising administering to a patient in need thereof a therapeutically effective amount of the pharmaceutical compositions described herein.

In certain embodiments, provided herein is a method of treating psoriasis comprising administering to a patient in need thereof a therapeutically effective amount of the pharmaceutical formulations described herein.

In certain embodiments, provided herein is a method of treating multiple sclerosis comprising delivering the compounds described herein to a lymphocyte of a patient in need thereof.

In certain embodiments, provided herein is a method of treating psoriasis comprising delivering the compounds described herein to a lymphocyte of a patient in need thereof.

In certain embodiments, provided herein is a method of treating multiple sclerosis comprising delivering the compounds described herein to lymphoid tissue such as lymph nodes of a patient in need thereof.

In certain embodiments, provided herein is a method of treating psoriasis comprising delivering the compounds described herein to lymphoid tissue such as lymph nodes of a patient in need thereof.

The pharmaceutical compositions and formulations described herein may be administered by any route, such as those routes described in Section 4.4.

4 DETAILED DESCRIPTION

Provided herein are certain thiazolidinone and oxazolidinone compounds, such as Compound 1, Compounds 1A-1F, and compounds of Formulas (I), (II), (III), and (IV), pharmaceutical compositions comprising such compounds, pharmaceutical formulations comprising such compounds and a pharmaceutically acceptable excipient, and methods for treating diseases or disorders associated with an activated immune system, e.g., multiple sclerosis and psoriasis, comprising administering such compounds, compositions, and/or formulations to a subject in need thereof.

Also provided herein are pharmaceutical compositions comprising certain compounds such as Compound 1, Compounds 1A-1F, and compounds of Formulas (I), (II), (III), and (IV) in combination with Compound 11, and methods for treating diseases or disorders associated with an activated immune system, e.g., multiple sclerosis and psoriasis, comprising administering an effective amount of such compositions to a subject in need thereof.

Also provided herein are pharmaceutical formulations comprising certain compounds such as Compound 1, Compounds 1A-1F, and compounds of Formulas (I), (II), (III), and (IV) in combination with Compound 11 and a pharmaceutically acceptable excipient and methods for treating diseases or disorders associated with an activated immune system, e.g., multiple sclerosis and psoriasis, comprising administering an effective amount of such formulations to a subject in need thereof.

Specific thiazolidinone and oxazolidinone compounds such as Compound 1, Compounds 1A-1F, and compounds of Formula (I), (II), (III), and (IV) are provided in Section 4.2. Methods of synthesizing compounds of Formula (I), (II), (III), and (IV) are provided in Section 4.3. Pharmaceutical compositions and routes of administration of compounds such as Compound 1, Compounds 1A-1F, and compounds of Formula (I), (II), (III), and (IV) are provided in Section 4.4. Therapeutic uses of compounds such as Compound 1, Compounds 1A-1F, and compounds of Formula (I), (II), (III), and (IV) are provided in Section 4.5.

4.1 Definitions

It should be noted that if there is a discrepancy between a depicted structure and a name for that structure, the depicted structure is to be accorded more weight.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, the term "alkyl" refers to a linear or branched saturated hydrocarbon, wherein the alkyl may be substituted or unsubstituted. For example, $C_{1-6}$ alkyl refers to a linear saturated hydrocarbon of 1 to 6 carbon atoms or a branched saturated hydrocarbon of 3 to 6 carbon atoms. In certain embodiments, the alkyl is a linear saturated hydrocarbon that has 1 to 20 ($C_{1-20}$), 1 to 15 ($C_{1-15}$), 1 to 10 ($C_{1-10}$), or 1 to 6 ($C_{1-6}$) carbon atoms, or branched saturated hydrocarbon that has 3 to 20 ($C_{3-20}$), 3 to 15 ($C_{3-15}$), 3 to 10 ($C_{3-10}$), or 3 to 6 ($C_{3-6}$) carbon atoms. Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), hexyl (including all isomeric forms), heptyl (including all isomeric forms), and octyl (including all isomeric forms).

As used herein, the term "cycloalkyl" refers to a saturated, or partially saturated cyclic alkyl group of 3 to 10 carbon atoms having a single cyclic ring or multiple condensed or bridged rings which can be optionally substituted with 1 to 3 alkyl groups. In some embodiments, the cycloalkyl group has 4 to 6 ring members. Such cycloalkyl groups include, by way of example, single ring structures such as cyclobutyl, cyclopentyl, cyclohexyl, cycloheptyl, cyclooctyl, and the like. Examples of unsaturated cycloalkyl groups include cyclooctenyl, cycloheptenyl, cyclohexenyl, cyclopentenyl, and cyclobutenyl, among others. A cycloalkyl group can be substituted or unsubstituted.

As used herein a "Compound" or "Compounds" comprise Compound 1, Compounds 1A-1F, a compound of Formula (I), a compound of Formula (II), a compound of Formula (III), a compound of Formula (IV), a compound listed in Table 1, a compound listed in Table 2, a compound listed in Table 3, a compound listed in Table 4, or a compound listed in Table 5. Compound 11, Compound 12, and Compounds 12A-12D are not encompassed in the definition of a "Compound" or "Compounds."

As used herein, the term "aryl" refers to a monovalent monocyclic aromatic group and/or monovalent polycyclic aromatic group that contains at least one aromatic carbon ring, wherein the alkyl may be substituted or unsubstituted. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl).

As used herein, the term "hydrogen" (alone or in combination with another term(s)) means —H.

As used herein, the term "hydroxyl" (alone or in combination with another term(s)) means —OH.

As used herein, the term "substituent" means positional variables on the atoms of a core molecule that are known to those skilled in the art to be chemical moieties that are appropriate for substitution at a designated atom position, replacing one or more hydrogens on the designated atom with a selection from the indicated group, provided that the designated atom's normal valency under the existing circumstances is not exceeded, and that the substitution results in a stable compound. Combinations of substituents and/or variables are permissible only if such combinations result in stable compounds. It should also be noted that any carbon as well as heteroatom with unsatisfied valences as described or shown herein is assumed to have a sufficient number of hydrogen atom(s) to satisfy the valences described or shown. Illustrative examples of substituents are those found in the exemplary compounds and embodiments disclosed herein, as well as halogen (chloro, iodo, bromo, or fluoro), alkyl, hydroxyl, cycloalkyl, or aryl.

As used herein, and unless otherwise specified, the term "substituted" means a group substituted by one to four or more substituents, such as alkyl, alkenyl, alkynyl, cycloalkyl, halo, haloalkyl (e.g., trifluoromethyl), haloalkoxy (e.g., trifluoromethoxy), hydroxyl, alkoxy, cycloalkyloxy, heterocyclyloxy, oxo, alkanoyl, aryl, arylalkyl, heteroaryl, heteroarylalkyl, heterocyclyl, aryloxy, alkanoyloxy, amino, arylamino, arylalkylamino, cycloalkylamino, heterocyclylamino, mono and di-substituted amino (in which the one or two substituents on the amino group are selected from alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, cycloalkylthio, heterocyclylthio, alkylthiono, arylthiono, arylalkylthiono, alkylsulfonyl, arylsulfonyl, arylalkylsulfonyl, sulfonamido (e.g., $SO_2NH_2$), substituted sulfonamido, nitro, cyano, carboxy, carbamyl (e.g., $CONH_2$), substituted carbamyl (e.g., CONH alkyl, CONH aryl, CONH arylalkyl or instances where there are two substituents on nitrogen selected from alkyl or arylalkyl), alkoxycarbonyl, aryl, substituted aryl, guanidino, substituted or unsubstituted heterocyclylalkyl, substituted or unsubstituted heteroaryl.

In the event that a range of the number of atoms in a structure is indicated (e.g., a 1 to 20 ($C_{1-20}$), 1 to 15 ($C_{1-15}$), 1 to 10 ($C_{1-10}$), or 1 to 6 ($C_{1-6}$) carbon atoms, or branched saturated hydrocarbon that has 3 to 20 ($C_{3-20}$), 3 to 15 ($C_{3-15}$), etc.), it is specifically contemplated that any subrange or individual number of carbon atoms falling within the indicated range also can be used. Thus, for instance, the recitation of a range of 1 to 20 ($C_{1-20}$), 1 to 15 ($C_{1-15}$), 1 to 10 ($C_{1-10}$), or 1 to 6 ($C_{1-6}$) carbon atoms, or branched saturated hydrocarbon that has 3 to 20 ($C_{3-20}$), 3 to 15 ($C_{3-15}$), etc. as used with respect to any chemical group (e.g., alkyl, cycloalkyl, etc.) referenced herein encompasses and specifically describes 1, 2, 3, 4, 5, 6, 7, 8, 9, 10, 11, 12, 13, 14, 15, 16, 17, 18, 19, or 20 carbon atoms, as appropriate, as well as any sub-range thereof.

As used herein, the term "macrocycle" refers to a molecule having a chemical structure including a ring or a cycle formed by at least 9 covalently bonded atoms.

As used herein, the compound "(2Z,5Z)-5-(3-chloro-4-[(2R)-2,3-dihydroxypropoxy]benzylidene)-3-(2-methylphenyl)-2-(propylimino)-1,3-thiazolidin-4-one", the compound "(Z)-5-((Z)-3-chloro-4-((R)-2,3-dihydroxypropoxy)benzylidene)-2-(propylimino)-3-(o-tolyl)thiazolidin-4-one", or Compound 11 has the following structure:

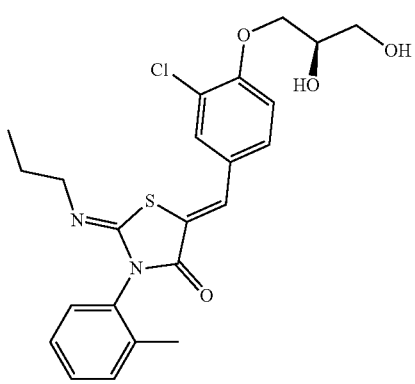 [SMILES: CCC/N=C1\S/C(=C\c2ccc(OC[C@H](O)CO)c(Cl)c2)C(=O)N1c1ccccc1C]

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of Compound 1, Compounds 1A-1F, the compounds of Formula (I), the compounds of Formula (II), the compounds of Formula (III), and the compounds of Formula (IV) include, but are not limited to metallic salts made from aluminum, calcium, lithium, magnesium, potassium, sodium, and zinc or organic salts made from lysine, N, N'-dibenzylethylenediamine, chloroprocaine, choline, diethanolamine, ethylenediamine, meglumine (N-methyl-glucamine), and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, oxalic, pamoic, pantothenic, phenylacetic, phosphoric, propionic, salicylic, stearic, succinic, sulfanilic, sulfuric, tartaric acid, naphthalene-1,5-disulfonic acid, ethan-1,2-disulfonic acid, ethanesulfonic acid, trifluoroacetic acid, 2-naphthalenesulfonic and p-toluenesulfonic acid. Suitable non-toxic acids also include, but are not limited to, ethanedisulfonic acid. Specific non-toxic acids include hydrochloric, hydrobromic, naphthalene-1,5-disulfonic, ethane-1,2-disulfonic, ethanesulfonic, p-toluenesulfonic, trifluoroacetic, and 2-naphthalenesulfonic acids. Examples of specific salts include hydrochloride, hydrobromide, napadisylate, 2-naphthalenesulfonate, edisylate salt, p-toluenesulfonate, trifluoroacetate, and ethanesulfonate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995), which is hereby incorporated by reference in its entirety.

As used herein, and unless otherwise specified, the term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid.

As used herein, and unless otherwise specified, the term "hydrate" means Compound 1, Compounds 1A-1F, a compound of Formula (I), (II), (III), or (IV) provided herein (see Section 4.2) or a salt thereof, that further includes a stoichiometric or non-stoichiometric amount of water bound by non-covalent intermolecular forces.

As used herein, and unless otherwise specified, the term "clathrate" means a Compound 1, Compounds 1A-1F, a compound of Formula (I), (II), (III), or (IV) provided herein (see Section 4.2), or a salt thereof, in the form of a crystal lattice that contains spaces (e.g., channels) that have a guest molecule (e.g., a solvent or water) trapped within or a crystal lattice wherein Compound 1, Compounds 1A-1F, or a compound of Formula (I), (II), (III), or (IV) receptor modulator is a guest molecule.

As used herein, and unless otherwise specified, the term "prodrug" means a compound that can hydrolyze, oxidize, or otherwise react under biological conditions (in vitro or in vivo) to provide an active compound, particularly Compound 1, Compounds 1A-1F, a compound of Formula (I), (II), (III), or (IV) provided herein (see Section 4.2). Examples of prodrugs include, but are not limited to, derivatives and metabolites of Compound 1, Compounds 1A-1F, a compound of Formula (I), (II), (III), or (IV) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh), each of which is hereby incorporated by reference in its entirety.

As used herein, and unless otherwise specified, the term "polymorph" refers to solid crystalline forms of a compound or complex thereof, particularly of Compound 1, Compounds 1A-1F, a compound of Formula (I), (II), (III), or (IV) provided herein (see Section 4.2). Different polymorphs of the same compound can exhibit different physical, chemical, and spectroscopic properties.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association:

2005; and *Handbook of Pharmaceutical Additives*, 3rd Edition, Ash and Ash Eds., Gower Publishing Company: 2007; *Pharmaceutical Preformulation and Formulation*, Gibson Ed., CRC Press LLC: Boca Raton, Fla., 2004, each of which is hereby incorporated by reference in its entirety.

As used herein, and unless otherwise specified, the term "composition" is intended to encompass a product comprising the specified ingredients in the specified amounts, as well as any product which results, directly or indirectly, from combination of the specified ingredients in the specified amounts.

Each structure depicted herein is meant to indicate the specific isomeric (e.g., enantiomeric, diastereomeric, and geometric (or conformational)) form drawn in the structure. Where not explicitly specified, any configuration of all isomeric (e.g., enantiomeric, diastereomeric, and geometric (or conformational)) forms of the structures are disclosed herein; for example, when not explicitly specified, the R, S, and racemate configurations for each asymmetric center are disclosed, both Z and E double bond isomers are disclosed, and both Z and E conformational isomers are disclosed. Where not explicitly indicated otherwise, a flat bond is intended to represent any configuration of all isomeric forms. Each structure depicted herein is meant to indicate the specific tautomeric form drawn in the structure.

As used herein, the symbol (±) indicates a racemic mixture of the stereocenter to which it specifically refers. If a flat bond is not referred to as (±) in the corresponding chemical name, that flat bond is intended to cover all configurations, as described above.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used here, the terms "treat," "treating," and "treatment" refer to an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

As used herein, and unless otherwise specified, the term "therapeutically effective amount" of a compound refers to an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human, in another embodiment a cell from any one of the foregoing animals.

In one embodiment, a subject or patient is a non-human animal, in another embodiment a non-human mammal. In another embodiment, a subject or patient is a human having or at risk for having a disease associated with an activated immune system. In certain embodiments, the disease or disorder can be treated and/or prevented with a selective S1P1 receptor agonist. In certain embodiments, the disease or disorder is selected from the group consisting of rejection of transplanted organs or tissue; graft-versus-host diseases brought about by transplantation; autoimmune syndromes including rheumatoid arthritis; systemic lupus erythematosus; Hashimoto's thyroiditis; lymphocytic thyroiditis; multiple sclerosis; myasthenia gravis; type I diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; coeliac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

4.2 Compounds

In a first aspect, provided herein is Compound 1: (5-(3-chloro-4-(2,3-dihydroxypropoxy)benzylidene)-3-(o-tolyl)thiazolidine-2,4-dione) or a pharmaceutically acceptable salt, hydrate, or solvate thereof.

In an embodiment of the first aspect, the compound is selected from the group consisting of the compounds in Table 1 or a pharmaceutically acceptable salt, hydrate, or solvate thereof:

TABLE 1

| Compounds 1A-1F | | |
|---|---|---|
| Compound No. | Compound Structure | Chemical Name* |
| 1A | | ±(Z)-5-(3-chloro-4-(2,3-dihydroxypropoxy)benzylidene)-3-(o-tolyl)thiazolidine-2,4-dione |
| 1B | | (R,Z)-5-(3-chloro-4-(2,3-dihydroxypropoxy)benzylidene)-3-(o-tolyl)thiazolidine-2,4-dione |
| 1C | | (S,Z)-5-(3-chloro-4-(2,3-dihydroxypropoxy)benzylidene)-3-(o-tolyl)thiazolidine-2,4-dione |

TABLE 1-continued

Compounds 1A-1F

| Compound No. | Compound Structure | Chemical Name* |
|---|---|---|
| 1D | 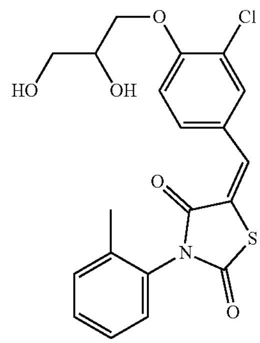 [SMILES: Cc1ccccc1N1C(=O)S/C(=C/c2ccc(OCC(O)CO)c(Cl)c2)C1=O] | ±(E)-5-(3-chloro-4-(2,3-dihydroxypropoxy)benzylidene)-3-(o-tolyl)thiazolidine-2,4-dione |
| 1E | 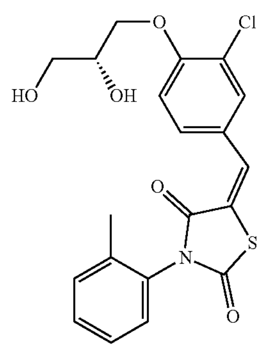 [SMILES: Cc1ccccc1N1C(=O)S/C(=C/c2ccc(OC[C@H](O)CO)c(Cl)c2)C1=O] | (R,E)-5-(3-chloro-4-(2,3-dihydroxypropoxy)benzylidene)-3-(o-tolyl)thiazolidine-2,4-dione |
| 1F | 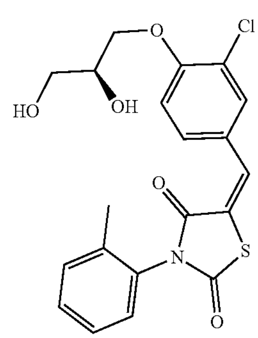 [SMILES: Cc1ccccc1N1C(=O)S/C(=C/c2ccc(OC[C@@H](O)CO)c(Cl)c2)C1=O] | (S,E)-5-(3-chloro-4-(2,3-dihydroxypropoxy)benzylidene)-3-(o-tolyl)thiazolidine-2,4-dione |

In a second aspect, provided herein are compounds of Formula (IA) and compounds of Formula (B). For ease of reference, the compounds of Formula (IA) and Formula (B) can be collectively referred to herein as the "compounds of Formula (I)" or simply, "Formula (I)."

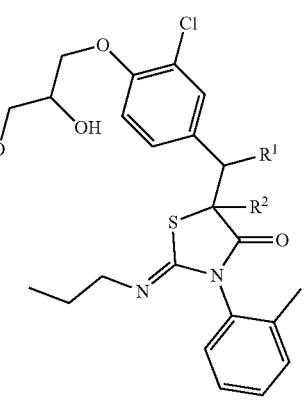

Formula (IA)

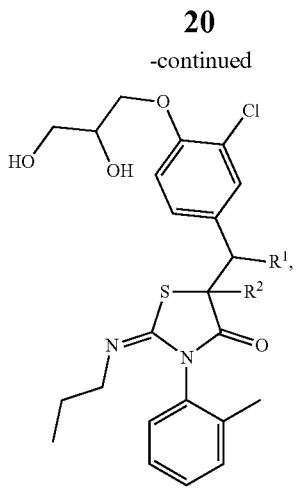

Formula (IB)

or a pharmaceutically acceptable salt, hydrate, or solvate thereof, wherein:
$R^1$ is =O or —OH; and
$R^2$ is —H; or
wherein $R^1$ and $R^2$ combine to form an epoxide ring with the carbon atoms to which they are attached.

In an embodiment, the compound of Formula (I) is: 5-((3-chloro-4-(2,3-dihydroxypropoxy)phenyl)(hydroxy)methyl)-2-(propylimino)-3-(o-tolyl)thiazolidin-4-one (Compound 2). In an embodiment, the compound of Formula (I) is: 5-(3-chloro-4-(2,3-dihydroxypropoxy)benzoyl)-2-(propylimino)-3-(o-tolyl)thiazolidin-4-one (Compound 3). In an embodiment, the compound of Formula (I) is: 2-(3-chloro-4-(2,3-dihydroxypropoxy)phenyl)-5-(propylimino)-6-(o-tolyl)-1-oxa-4-thia-6-azaspiro[2.4]heptan-7-one (Compound 4).

In an embodiment of the second aspect, the compounds of Formula (I) are those wherein the compound is selected from the group consisting of the compounds in Table 2 or a pharmaceutically acceptable salt, hydrate, or solvate thereof:

TABLE 2

Compounds of Formula (I)

| Compound No. | Compound Structure | Chemical Name* |
|---|---|---|
| 2A | 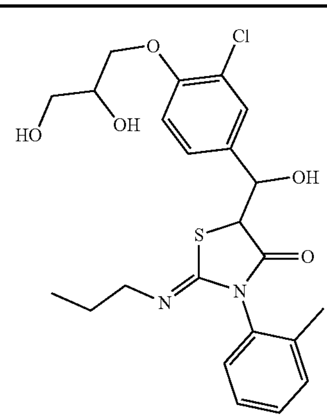 | (Z)-5-((3-chloro-4-((±)-2,3-dihydroxypropoxy)phenyl)(hydroxy)methyl)-2-(propylimino)-3-(o-tolyl)thiazolidin-4-one |

TABLE 2-continued
Compounds of Formula (I)
| Compound No. | Compound Structure | Chemical Name* |
|---|---|---|
| 2B | 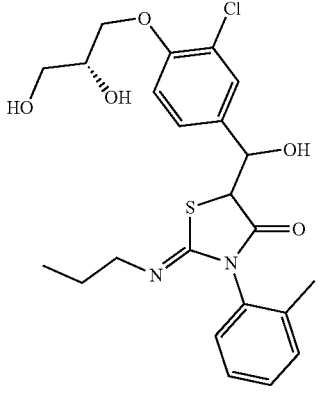 [SMILES: CCC/N=C1\SC(C(O)c2ccc(OC[C@H](O)CO)c(Cl)c2)C(=O)N1c1ccccc1C] | (Z)-5-((3-chloro-4-((R)-2,3-dihydroxypropoxy)phenyl)(hydroxy)methyl)-2-(propylimino)-3-(o-tolyl)thiazolidin-4-one |
| 2C | 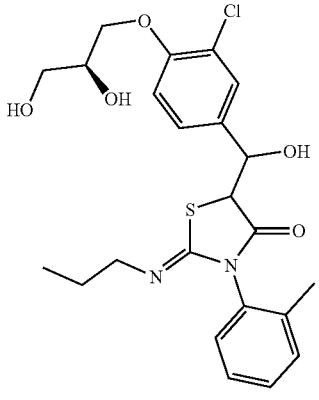 [SMILES: CCC/N=C1\SC(C(O)c2ccc(OC[C@@H](O)CO)c(Cl)c2)C(=O)N1c1ccccc1C] | (Z)-5-((3-chloro-4-((S)-2,3-dihydroxypropoxy)phenyl)(hydroxy)methyl)-2-(propylimino)-3-(o-tolyl)thiazolidin-4-one |
| 2D | 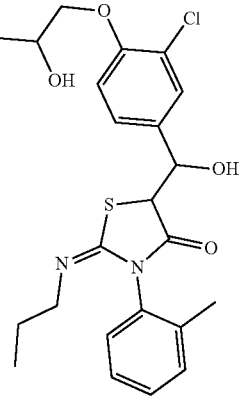 | (E)-5-((3-chloro-4-((±)-2,3-dihydroxypropoxy)phenyl)(hydroxy)methyl)-2-(propylimino)-3-(o-tolyl)thiazolidin-4-one |

TABLE 2-continued

Compounds of Formula (I)

| Compound No. | Compound Structure | Chemical Name* |
|---|---|---|
| 2E | 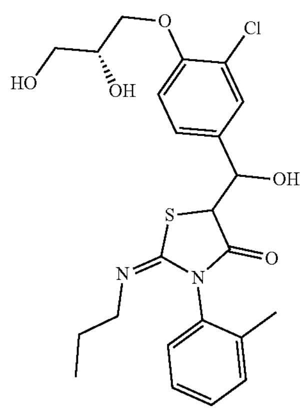 [SMILES: CCC/N=C1/SC(C(O)c2ccc(OC[C@H](O)CO)c(Cl)c2)C(=O)N1c1ccccc1C] | (E)-5-((3-chloro-4-((R)-2,3-dihydroxypropoxy)phenyl)(hydroxy)methyl)-2-(propylimino)-3-(o-tolyl)thiazolidin-4-one |
| 2F | 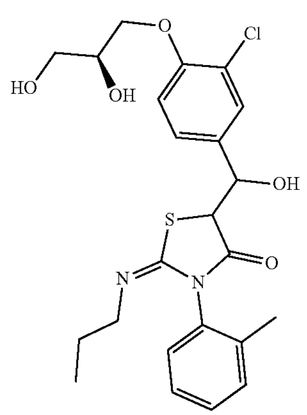 [SMILES: CCC/N=C1/SC(C(O)c2ccc(OC[C@@H](O)CO)c(Cl)c2)C(=O)N1c1ccccc1C] | (E)-5-((3-chloro-4-((S)-2,3-dihydroxypropoxy)phenyl)(hydroxy)methyl)-2-(propylimino)-3-(o-tolyl)thiazolidin-4-one |
| 3A | 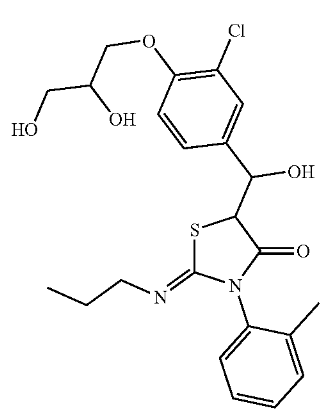 [SMILES: CCC/N=C1\SC(C(O)c2ccc(OCC(O)CO)c(Cl)c2)C(=O)N1c1ccccc1C] | (Z)-5-(3-chloro-4-((±)-2,3-dihydroxypropoxy)benzoyl)-2-(propylimino)-3-(o-tolyl)thiazolidin-4-one |

TABLE 2-continued

Compounds of Formula (I)

| Compound No. | Compound Structure | Chemical Name* |
|---|---|---|
| 3B | 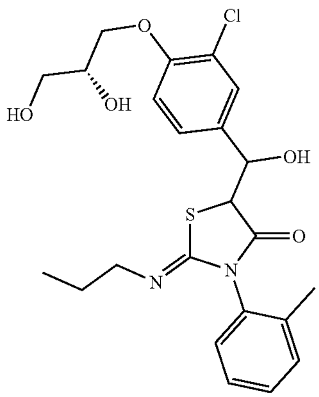 [SMILES: CCC/N=C1\SC(C(O)c2ccc(OC[C@H](O)CO)c(Cl)c2)C(=O)N1c1ccccc1C] | (Z)-5-(3-chloro-4-((R)-2,3-dihydroxypropoxy)benzoyl)-2-(propylimino)-3-(o-tolyl)thiazolidin-4-one |
| 3C | 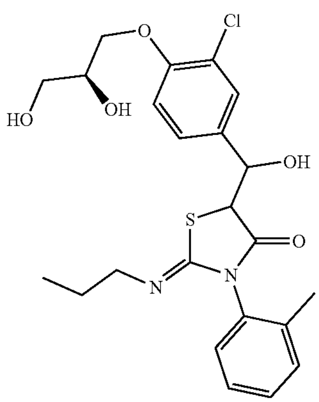 [SMILES: CCC/N=C1\SC(C(O)c2ccc(OC[C@@H](O)CO)c(Cl)c2)C(=O)N1c1ccccc1C] | (Z)-5-(3-chloro-4-((S)-2,3-dihydroxypropoxy)benzoyl)-2-(propylimino)-3-(o-tolyl)thiazolidin-4-one |
| 3D | 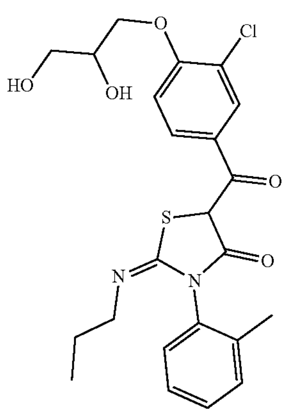 [SMILES: CCC/N=C1/SC(C(=O)c2ccc(OCC(O)CO)c(Cl)c2)C(=O)N1c1ccccc1C] | (E)-5-(3-chloro-4-((±)-2,3-dihydroxypropoxy)benzoyl)-2-(propylimino)-3-(o-tolyl)thiazolidin-4-one |

TABLE 2-continued

Compounds of Formula (I)

| Compound No. | Compound Structure | Chemical Name* |
|---|---|---|
| 3E | 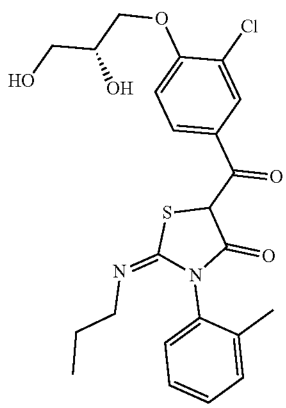 [SMILES: CCC/N=C1/SC(C(=O)c2ccc(OC[C@H](O)CO)c(Cl)c2)C(=O)N1c1ccccc1C] | (E)-5-(3-chloro-4-((R)-2,3-dihydroxypropoxy)benzoyl)-2-(propylimino)-3-(o-tolyl)thiazolidin-4-one |
| 3F | 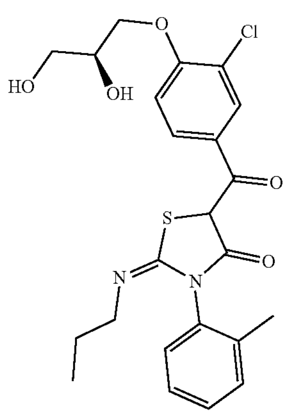 [SMILES: CCC/N=C1/SC(C(=O)c2ccc(OC[C@@H](O)CO)c(Cl)c2)C(=O)N1c1ccccc1C] | (E)-5-(3-chloro-4-((S)-2,3-dihydroxypropoxy)benzoyl)-2-(propylimino)-3-(o-tolyl)thiazolidin-4-one |
| 4A | 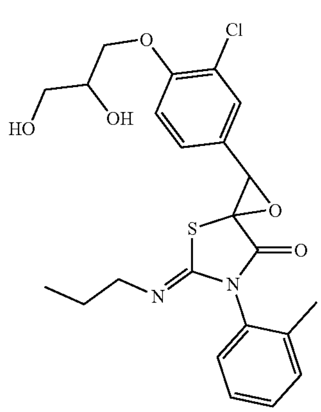 [SMILES: CCC/N=C1\SC2(OC2c2ccc(OCC(O)CO)c(Cl)c2)C(=O)N1c1ccccc1C] | (Z)-2-(3-chloro-4-((±)-2,3-dihydroxypropoxy)phenyl)-5-(propylimino)-6-(o-tolyl)-1-oxa-4-thia-6-azaspiro[2.4]heptan-7-one |

TABLE 2-continued
Compounds of Formula (I)
| Compound No. | Compound Structure | Chemical Name* |
|---|---|---|
| 4B | 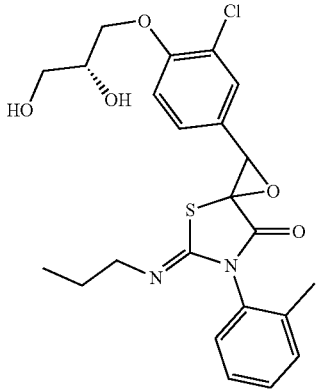 [SMILES: CCC/N=C1\SC2(OC2c2ccc(OC[C@H](O)CO)c(Cl)c2)C(=O)N1c1ccccc1C] | (Z)-2-(3-chloro-4-((R)-2,3-dihydroxypropoxy)phenyl)-5-(propylimino)-6-(o-tolyl)-1-oxa-4-thia-6-azaspiro[2.4]heptan-7-one |
| 4C | 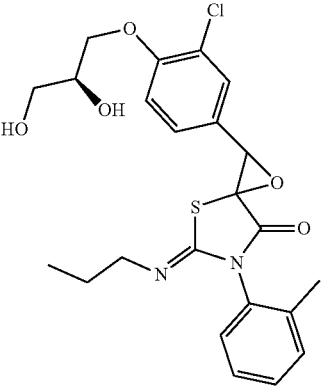 [SMILES: CCC/N=C1\SC2(OC2c2ccc(OC[C@@H](O)CO)c(Cl)c2)C(=O)N1c1ccccc1C] | (Z)-2-(3-chloro-4-((S)-2,3-dihydroxypropoxy)phenyl)-5-(propylimino)-6-(o-tolyl)-1-oxa-4-thia-6-azaspiro[2.4]heptan-7-one |
| 4D | 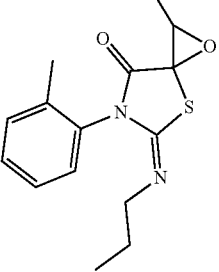 | (E)-2-(3-chloro-4-((±)-2,3-dihydroxypropoxy)phenyl)-5-(propylimino)-6-(o-tolyl)-1-oxa-4-thia-6-azaspiro[2.4]heptan-7-one |

TABLE 2-continued

Compounds of Formula (I)

| Compound No. | Compound Structure | Chemical Name* |
|---|---|---|
| 4E | 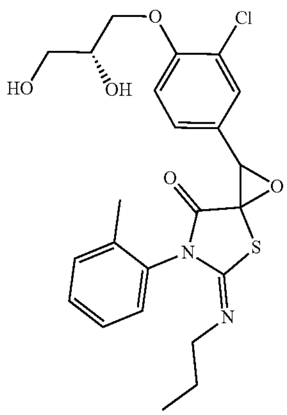 [SMILES: CCC/N=C1/SC2(OC2c2ccc(OC[C@H](O)CO)c(Cl)c2)C(=O)N1c1ccccc1C] | (E)-2-(3-chloro-4-((R)-2,3-dihydroxypropoxy)phenyl)-5-(propylimino)-6-(o-tolyl)-1-oxa-4-thia-6-azaspiro[2.4]heptan-7-one |
| 4F | 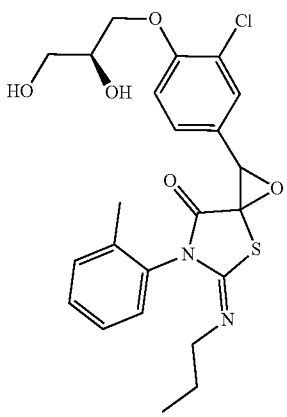 [SMILES: CCC/N=C1/SC2(OC2c2ccc(OC[C@@H](O)CO)c(Cl)c2)C(=O)N1c1ccccc1C] | (E)-2-(3-chloro-4-((S)-2,3-dihydroxypropoxy)phenyl)-5-(propylimino)-6-(o-tolyl)-1-oxa-4-thia-6-azaspiro[2.4]heptan-7-one |

*Chemical Names automatically generated with ChemDraw Professional, Version 15.1.

A person of ordinary skill in the art would recognize that the compounds shown in Table 2 may have additional chiral centers that are depicted as flat bonds. Specifically, Compounds 2A-2F include additional chiral centers at the carbon atom in the 5-position on the thiazolidine ring and the bridging carbon atom adjacent thereto. Additionally, Compounds 3A-3F include one additional chiral center at the carbon atom in the 5-position on the thiazolidine ring. Finally, Compounds 4A-4F include achirality around the epoxide ring. While the stereochemistry may not be shown for those chiral centers, the structures depicted herein are intended to indicate each of the possible stereochemical configurations of those chiral centers. In other words, where not specifically indicated, any chiral center in the compounds set forth in Table 2 can be in the R-configuration, S-configuration, or mixtures thereof, including racemic mixtures. Additionally, Compounds 3A-3F are shown in the keto form. Also disclosed herein are the enol forms of Compounds 3A-3F.

In a third aspect, provided herein are compounds of Formula (IIA), compounds of Formula (IIB), compounds of Formula (IIC), and compounds of Formula (IID). For ease of reference, the compounds of Formula (IIA), Formula (IIB), Formula (IIC), and Formula (IID) can be collectively referred to herein as the "compounds of Formula (II)" or simply, "Formula (II)."

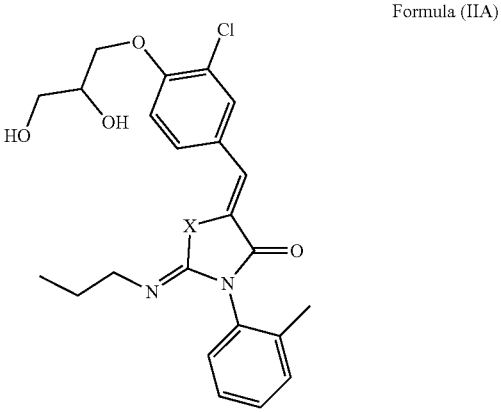

Formula (IIA)

Formula (IIB)

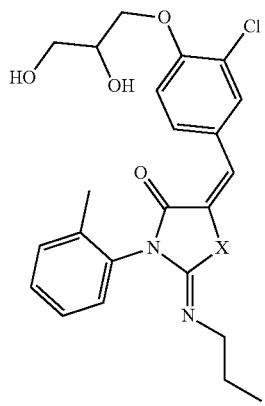

Formula (IIC)

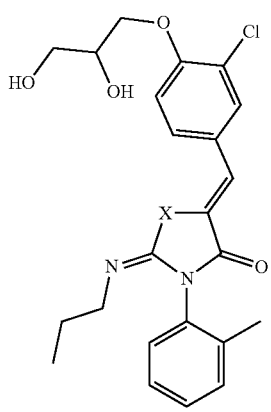

Formula (IID)

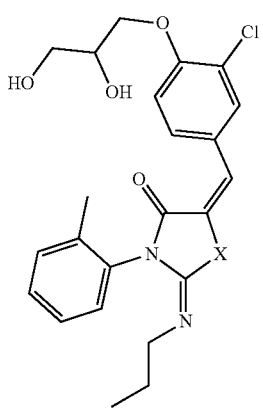

or a pharmaceutically acceptable salt, hydrate, or solvate thereof, wherein:

X is —O— or —S(O)—.

In an embodiment, the compound of Formula (II) is: 5-(3-chloro-4-(2,3-dihydroxypropoxy)benzylidene)-2-(propylimino)-3-(o-tolyl)thiazolidin-4-one 1-oxide (Compound 5). In an embodiment, the compound of Formula (II) is: 5-(3-chloro-4-(2,3-dihydroxypropoxy)benzylidene)-2-(propylimino)-3-(o-tolyl)oxazolidin-4-one (Compound 6).

In an embodiment of the third aspect, the compounds of Formula (II) are those wherein the compound is selected from the group consisting of the compounds in Table 3 or a pharmaceutically acceptable salt, hydrate, or solvate thereof:

TABLE 3

Compounds of Formula (II)

| Compound No. | Compound Structure | Chemical Name* |
|---|---|---|
| 5A | 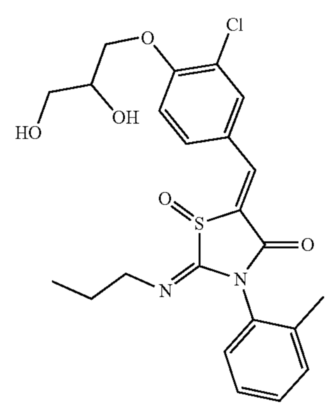 [SMILES: CCC/N=C1/N(c2ccccc2C)C(=O)/C(=C/c2ccc(OCC(O)CO)c(Cl)c2)S1=O] | (Z)-5-((Z)-3-chloro-4-((±)-2,3-dihydroxypropoxy)benzylidene)-2-(propylimino)-3-(o-tolyl)thiazolidin-4-one 1-oxide |

TABLE 3-continued

Compounds of Formula (II)

| Compound No. | Compound Structure | Chemical Name* |
|---|---|---|
| 5B | 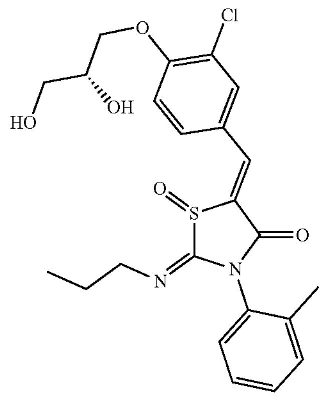 [SMILES: CCC/N=C1/N(c2ccccc2C)C(=O)/C(=C/c2ccc(OC[C@H](O)CO)c(Cl)c2)S1=O] | (Z)-5-((Z)-3-chloro-4-((R)-2,3-dihydroxypropoxy)benzylidene)-2-(propylimino)-3-(o-tolyl)thiazolidin-4-one 1-oxide |
| 5C | 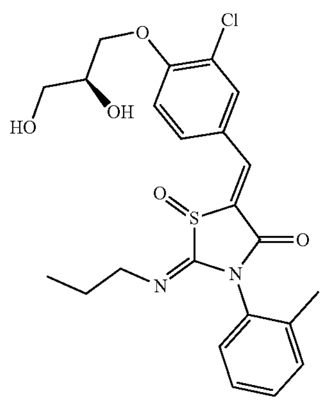 [SMILES: CCC/N=C1/N(c2ccccc2C)C(=O)/C(=C/c2ccc(OC[C@@H](O)CO)c(Cl)c2)S1=O] | (Z)-5-((Z)-3-chloro-4-((S)-2,3-dihydroxypropoxy)benzylidene)-2-(propylimino)-3-(o-tolyl)thiazolidin-4-one 1-oxide |
| 5D | 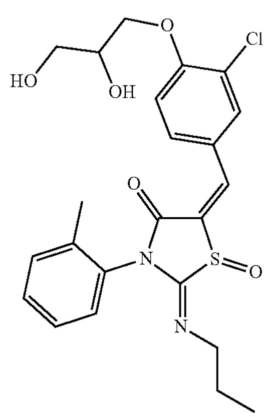 [SMILES: CCC/N=C1/N(c2ccccc2C)C(=O)/C(=C\c2ccc(OCC(O)CO)c(Cl)c2)S1=O] | (Z)-5-((E)-3-chloro-4-((±)-2,3-dihydroxypropoxy)benzylidene)-2-(propylimino)-3-(o-tolyl)thiazolidin-4-one 1-oxide |

TABLE 3-continued
Compounds of Formula (II)
| Compound No. | Compound Structure | Chemical Name* |
|---|---|---|
| 5E | 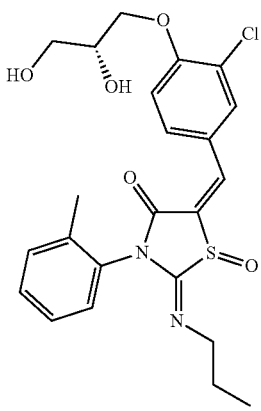 [SMILES: CCC/N=C1/N(c2ccccc2C)C(=O)/C(=C\c2ccc(OC[C@H](O)CO)c(Cl)c2)S1=O] | (Z)-5-((E)-3-chloro-4-((R)-2,3-dihydroxypropoxy)benzylidene)-2-(propylimino)-3-(o-tolyl)thiazolidin-4-one 1-oxide |
| 5F | 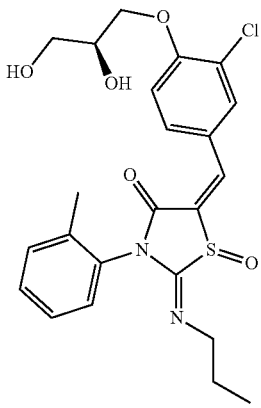 [SMILES: CCC/N=C1/N(c2ccccc2C)C(=O)/C(=C\c2ccc(OC[C@@H](O)CO)c(Cl)c2)S1=O] | (Z)-5-((E)-3-chloro-4-((S)-2,3-dihydroxypropoxy)benzylidene)-2-(propylimino)-3-(o-tolyl)thiazolidin-4-one 1-oxide |
| 5G | 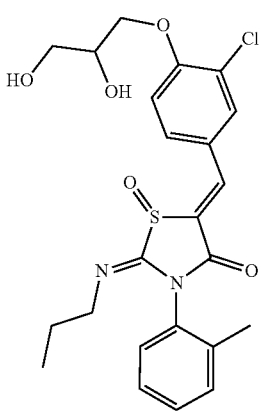 | (E)-5-((Z)-3-chloro-4-((±)-2,3-dihydroxypropoxy)benzylidene)-2-(propylimino)-3-(o-tolyl)thiazolidin-4-one 1-oxide |

TABLE 3-continued

Compounds of Formula (II)

| Compound No. | Compound Structure | Chemical Name* |
|---|---|---|
| 5H | 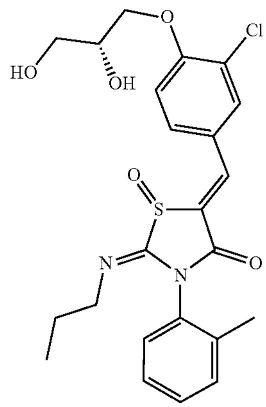 [SMILES: CCC/N=C1\N(c2ccccc2C)C(=O)/C(=C/c2ccc(OC[C@H](O)CO)c(Cl)c2)S1=O] | (E)-5-((Z)-3-chloro-4-((R)-2,3-dihydroxypropoxy)benzylidene)-2-(propylimino)-3-(o-tolyl)thiazolidin-4-one 1-oxide |
| 5I | 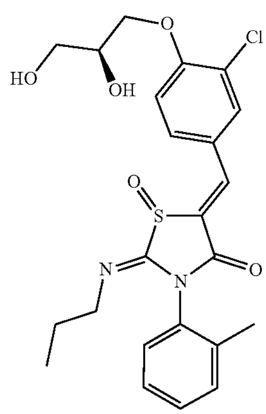 [SMILES: CCC/N=C1\N(c2ccccc2C)C(=O)/C(=C/c2ccc(OC[C@@H](O)CO)c(Cl)c2)S1=O] | (E)-5-((Z)-3-chloro-4-((S)-2,3-dihydroxypropoxy)benzylidene)-2-(propylimino)-3-(o-tolyl)thiazolidin-4-one 1-oxide |
| 5J | 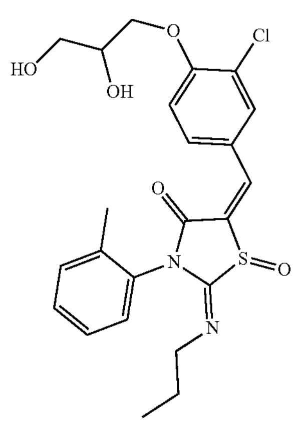 [SMILES: CCC/N=C1\N(c2ccccc2C)C(=O)/C(=C\c2ccc(OCC(O)CO)c(Cl)c2)S1=O] | (E)-5-((E)-3-chloro-4-((±)-2,3-dihydroxypropoxy)benzylidene)-2-(propylimino)-3-(o-tolyl)thiazolidin-4-one 1-oxide |

TABLE 3-continued
Compounds of Formula (II)
| Compound No. | Compound Structure | Chemical Name* |
|---|---|---|
| 5K | 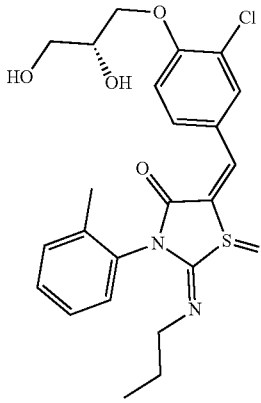 | (E)-5-((E)-3-chloro-4-((R)-2,3-dihydroxypropoxy)benzylidene)-2-(propylimino)-3-(o-tolyl)thiazolidin-4-one 1-oxide |
| 5L | 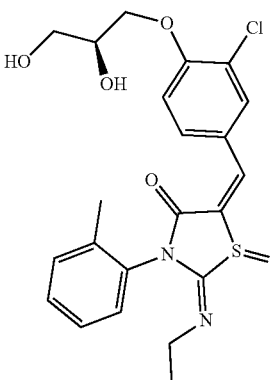 | (E)-5-((E)-3-chloro-4-((S)-2,3-dihydroxypropoxy)benzylidene)-2-(propylimino)-3-(o-tolyl)thiazolidin-4-one 1-oxide |
| 6A | 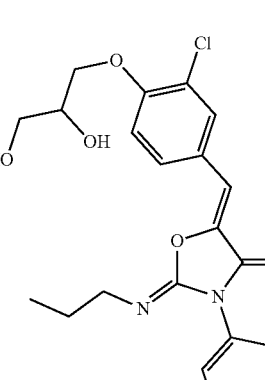 | (Z)-5-((Z)-3-chloro-4-((±)-2,3-dihydroxypropoxy)benzylidene)-2-(propylimino)-3-(o-tolyl)oxazolidin-4-one |

TABLE 3-continued

Compounds of Formula (II)

| Compound No. | Compound Structure | Chemical Name* |
|---|---|---|
| 6B | 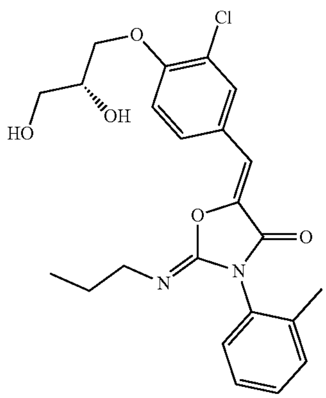 [SMILES: CCC/N=C1\O/C(=C\c2ccc(OC[C@H](O)CO)c(Cl)c2)C(=O)N1c1ccccc1C] | (Z)-5-((Z)-3-chloro-4-((R)-2,3-dihydroxypropoxy)benzylidene)-2-(propylimino)-3-(o-tolyl)oxazolidin-4-one |
| 6C | 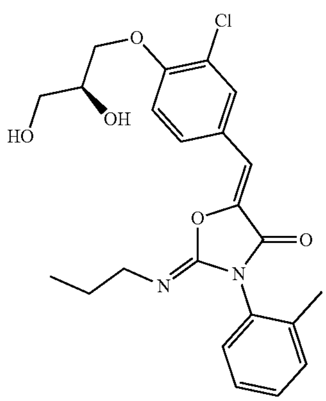 [SMILES: CCC/N=C1\O/C(=C\c2ccc(OC[C@@H](O)CO)c(Cl)c2)C(=O)N1c1ccccc1C] | (Z)-5-((Z)-3-chloro-4-((S)-2,3-dihydroxypropoxy)benzylidene)-2-(propylimino)-3-(o-tolyl)oxazolidin-4-one |
| 6D | 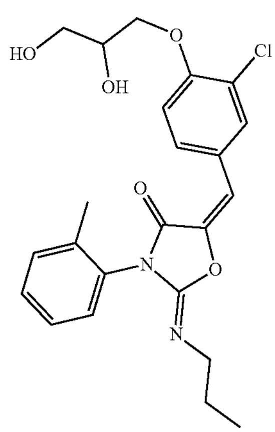 [SMILES: CCC/N=C1\O/C(=C/c2ccc(OCC(O)CO)c(Cl)c2)C(=O)N1c1ccccc1C] | (Z)-5-((E)-3-chloro-4-((±)-2,3-dihydroxypropoxy)benzylidene)-2-(propylimino)-3-(o-tolyl)oxazolidin-4-one |

TABLE 3-continued

Compounds of Formula (II)

| Compound No. | Compound Structure | Chemical Name* |
|---|---|---|
| 6E | 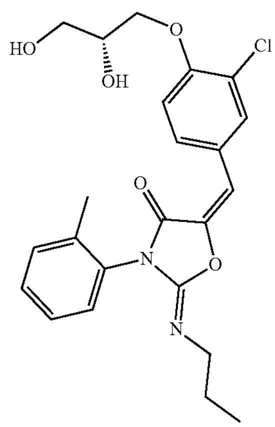 [SMILES: CCC/N=C1\O/C(=C/c2ccc(OC[C@H](O)CO)c(Cl)c2)C(=O)N1c1ccccc1C] | (Z)-5-((E)-3-chloro-4-((R)-2,3-dihydroxypropoxy)benzylidene)-2-(propylimino)-3-(o-tolyl)oxazolidin-4-one |
| 6F | 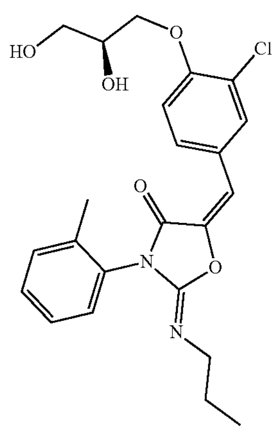 [SMILES: CCC/N=C1\O/C(=C/c2ccc(OC[C@@H](O)CO)c(Cl)c2)C(=O)N1c1ccccc1C] | (Z)-5-((E)-3-chloro-4-((S)-2,3-dihydroxypropoxy)benzylidene)-2-(propylimino)-3-(o-tolyl)oxazolidin-4-one |
| 6G | 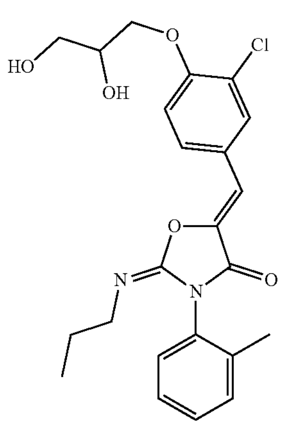 [SMILES: CCC/N=C1/O/C(=C\c2ccc(OCC(O)CO)c(Cl)c2)C(=O)N1c1ccccc1C] | (E)-5-((Z)-3-chloro-4-((±)-2,3-dihydroxypropoxy)benzylidene)-2-(propylimino)-3-(o-tolyl)oxazolidin-4-one |

TABLE 3-continued
Compounds of Formula (II)
| Compound No. | Compound Structure | Chemical Name* |
|---|---|---|
| 6H | 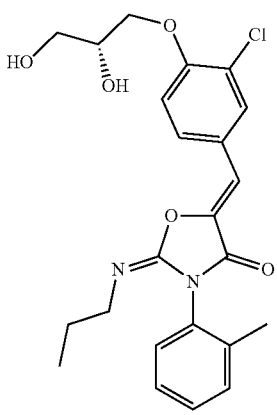 [SMILES: CCC/N=C1/O/C(=C\c2ccc(OC[C@H](O)CO)c(Cl)c2)C(=O)N1c1ccccc1C] | (E)-5-((Z)-3-chloro-4-((R)-2,3-dihydroxypropoxy)benzylidene)-2-(propylimino)-3-(o-tolyl)oxazolidin-4-one |
| 6I | 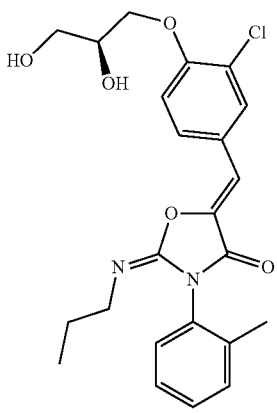 [SMILES: CCC/N=C1/O/C(=C\c2ccc(OC[C@@H](O)CO)c(Cl)c2)C(=O)N1c1ccccc1C] | (E)-5-((Z)-3-chloro-4-((S)-2,3-dihydroxypropoxy)benzylidene)-2-(propylimino)-3-(o-tolyl)oxazolidin-4-one |
| 6J | 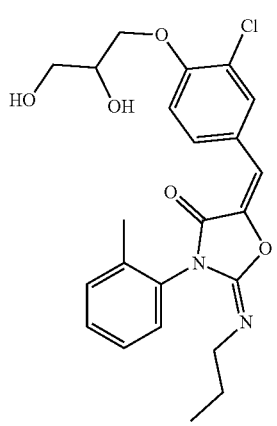 [SMILES: CCC/N=C1/O/C(=C/c2ccc(OCC(O)CO)c(Cl)c2)C(=O)N1c1ccccc1C] | (E)-5-((E)-3-chloro-4-((±)-2,3-dihydroxypropoxy)benzylidene)-2-(propylimino)-3-(o-tolyl)oxazolidin-4-one |

TABLE 3-continued

Compounds of Formula (II)

| Compound No. | Compound Structure | Chemical Name* |
|---|---|---|
| 6K | 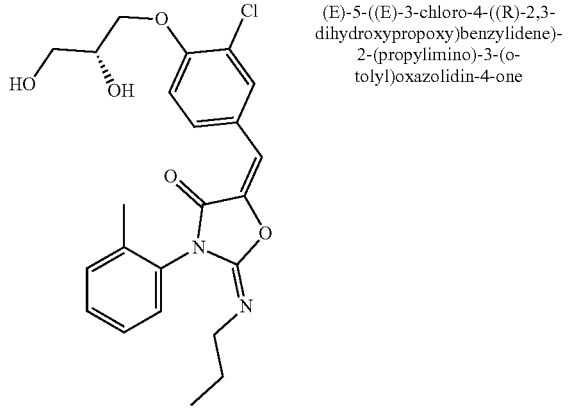 | (E)-5-((E)-3-chloro-4-((R)-2,3-dihydroxypropoxy)benzylidene)-2-(propylimino)-3-(o-tolyl)oxazolidin-4-one |
| 6L | 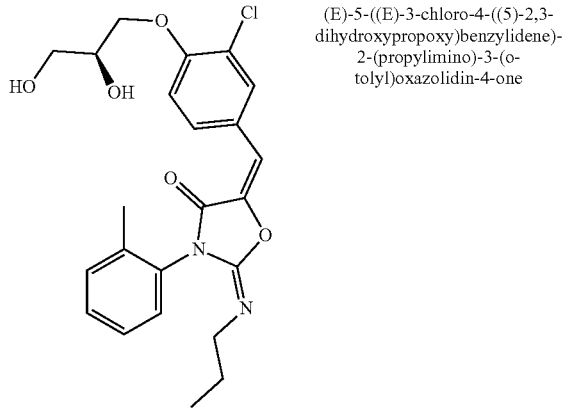 | (E)-5-((E)-3-chloro-4-((S)-2,3-dihydroxypropoxy)benzylidene)-2-(propylimino)-3-(o-tolyl)oxazolidin-4-one |

*Chemical Names automatically generated with ChemDraw Professional, Version 15.1.

A person of ordinary skill in the art would recognize that the compounds shown in Table 3 may have additional chiral centers that are depicted as flat bonds. Specifically, Compounds 5A-5L include an additional chiral center on the sulfur atom in the thiazolidine ring. While the stereochemistry may not be shown for those chiral centers, the structures depicted herein are intended to indicate each of the possible stereochemical configurations of those chiral centers. In other words, where not specifically indicated, any chiral center in the compounds set forth in Table 2 can be in the R-configuration, S-configuration, or mixtures thereof, including racemic mixtures.

In a fourth aspect, provided herein are compounds of Formula (IIIA), compounds of Formula (IIIB), compounds of Formula (IIIC), and compounds of Formula (IID). For ease of reference, the compounds of Formula (IIIA), Formula (IIIB), Formula (IIIC), and Formula (IIID) can be collectively referred to herein as the "compounds of Formula (III)" or simply, "Formula (III)."

Formula (IIIA)

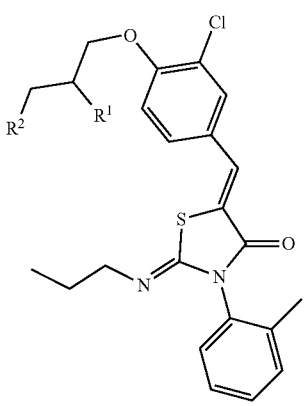

Formula (IIIB)

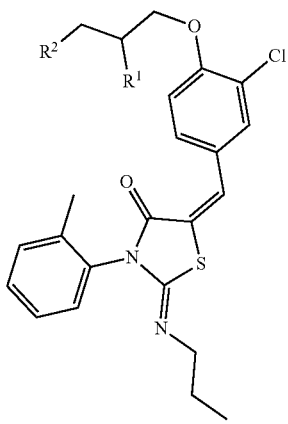

Formula (IIIC)

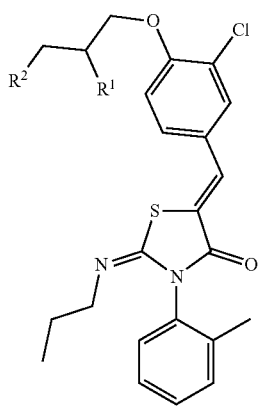

Formula (IIID)

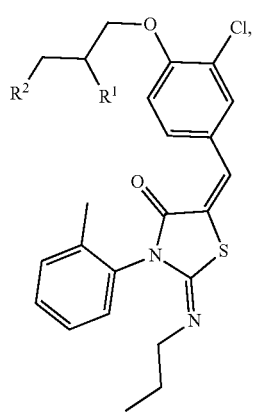

or a pharmaceutically acceptable salt, hydrate, or solvate thereof, wherein:

one of $R^1$ or $R^2$ is —OH and the other of $R^1$ or $R^2$ is =O.

In one embodiment, the compound of Formula (III) is: 5-(3-chloro-4-(3-hydroxy-2-oxopropoxy)benzylidene)-2-(propylimino)-3-(o-tolyl)thiazolidin-4-one (Compound 7).

In one embodiment, the compound of Formula (III) is: 3-(2-chloro-4-((4-oxo-2-(propylimino)-3-(o-tolyl)thiazolidin-5-ylidene)methyl)phenoxy)-2-hydroxypropanal (Compound 8).

In an embodiment of the fourth aspect, the compounds of Formula (III) are those wherein the compound is selected from the group consisting of the compounds in Table 4 or a pharmaceutically acceptable salt, hydrate, or solvate thereof:

TABLE 4

| Compounds of Formula (III) | | |
|---|---|---|
| Compound No. | Compound Structure | Chemical Name* |
| 7A |  | (Z)-5-((Z)-3-chloro-4-(3-hydroxy-2-oxopropoxy)benzylidene)-2-(propylimino)-3-(o-tolyl)thiazolidin-4-one |

TABLE 4-continued
| | | |
|---|---|---|
| 7B | 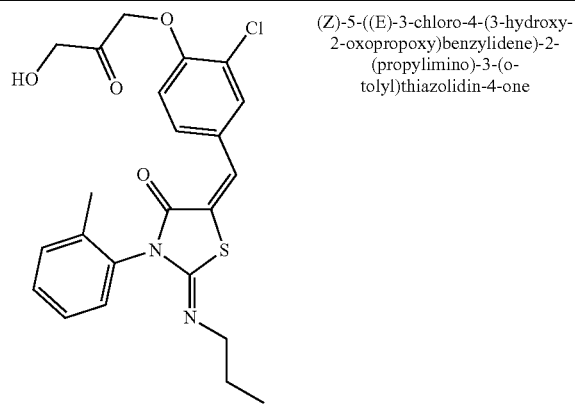 | (Z)-5-((E)-3-chloro-4-(3-hydroxy-2-oxopropoxy)benzylidene)-2-(propylimino)-3-(o-tolyl)thiazolidin-4-one |
| 7C | 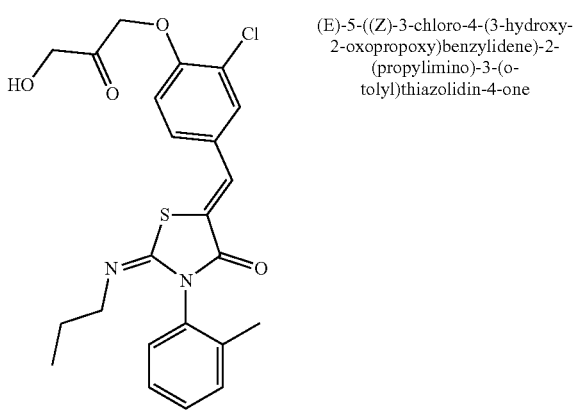 | (E)-5-((Z)-3-chloro-4-(3-hydroxy-2-oxopropoxy)benzylidene)-2-(propylimino)-3-(o-tolyl)thiazolidin-4-one |
| 7D | 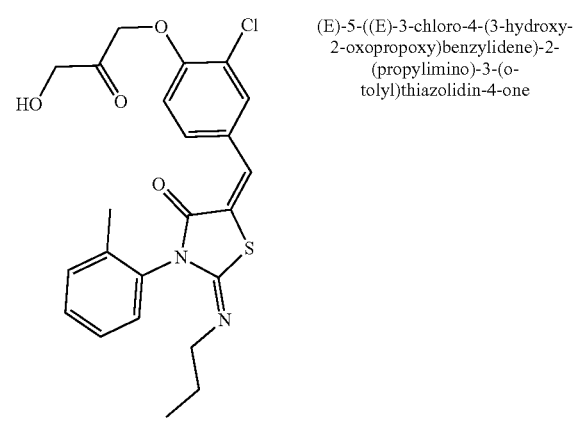 | (E)-5-((E)-3-chloro-4-(3-hydroxy-2-oxopropoxy)benzylidene)-2-(propylimino)-3-(o-tolyl)thiazolidin-4-one |
| 8A | 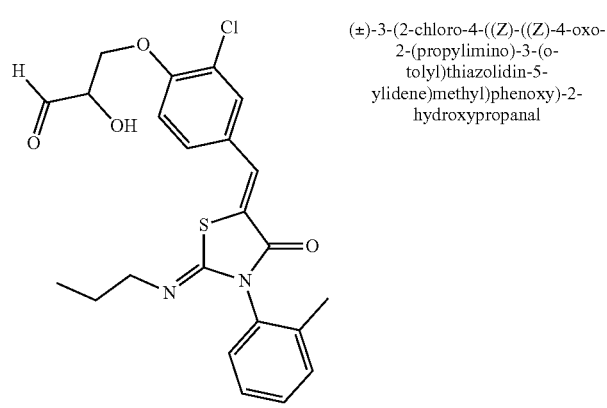 | (±)-3-(2-chloro-4-((Z)-((Z)-4-oxo-2-(propylimino)-3-(o-tolyl)thiazolidin-5-ylidene)methyl)phenoxy)-2-hydroxypropanal |

TABLE 4-continued

| | | |
|---|---|---|
| 8B | 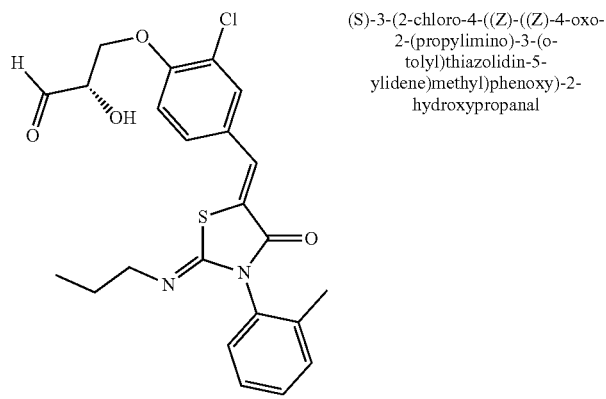 | (S)-3-(2-chloro-4-((Z)-((Z)-4-oxo-2-(propylimino)-3-(o-tolyl)thiazolidin-5-ylidene)methyl)phenoxy)-2-hydroxypropanal |
| 8C | 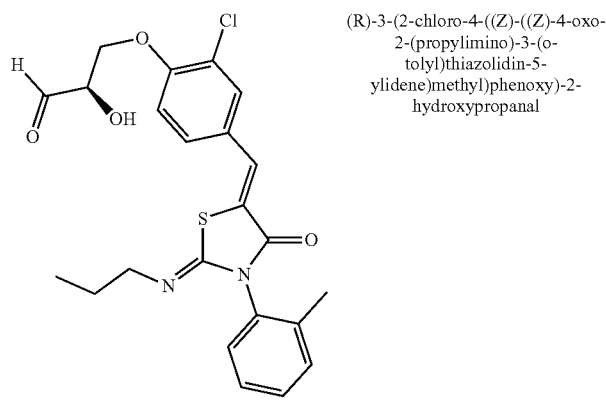 | (R)-3-(2-chloro-4-((Z)-((Z)-4-oxo-2-(propylimino)-3-(o-tolyl)thiazolidin-5-ylidene)methyl)phenoxy)-2-hydroxypropanal |
| 8D | 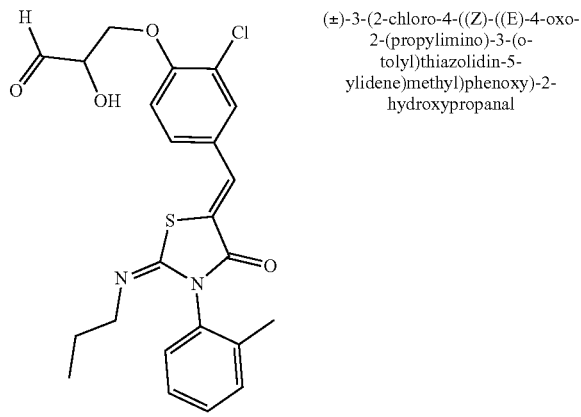 | (±)-3-(2-chloro-4-((Z)-((E)-4-oxo-2-(propylimino)-3-(o-tolyl)thiazolidin-5-ylidene)methyl)phenoxy)-2-hydroxypropanal |
| 8E | 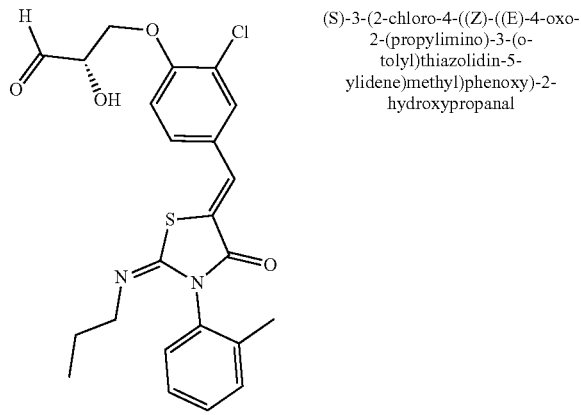 | (S)-3-(2-chloro-4-((Z)-((E)-4-oxo-2-(propylimino)-3-(o-tolyl)thiazolidin-5-ylidene)methyl)phenoxy)-2-hydroxypropanal |

TABLE 4-continued
| | | |
|---|---|---|
| 8F | 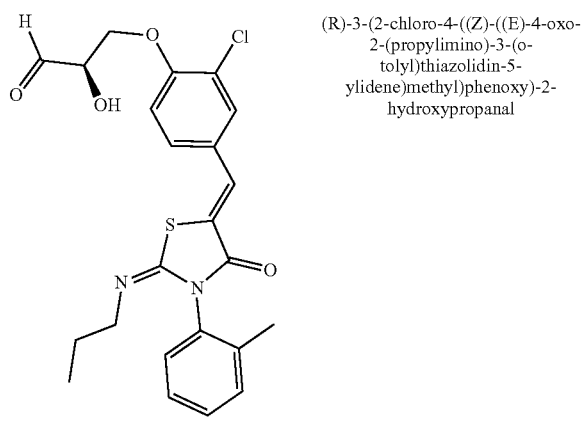 | (R)-3-(2-chloro-4-((Z)-((E)-4-oxo-2-(propylimino)-3-(o-tolyl)thiazolidin-5-ylidene)methyl)phenoxy)-2-hydroxypropanal |
| 8G | 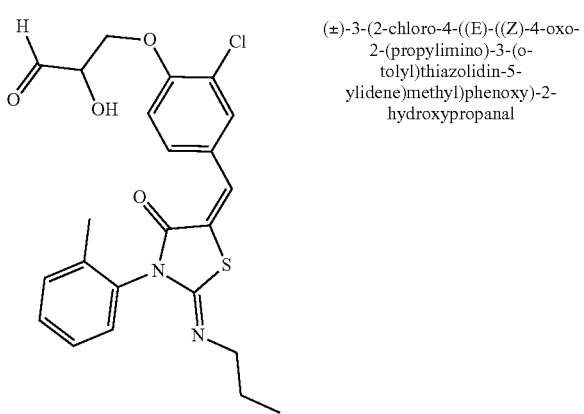 | (±)-3-(2-chloro-4-((E)-((Z)-4-oxo-2-(propylimino)-3-(o-tolyl)thiazolidin-5-ylidene)methyl)phenoxy)-2-hydroxypropanal |
| 8H | 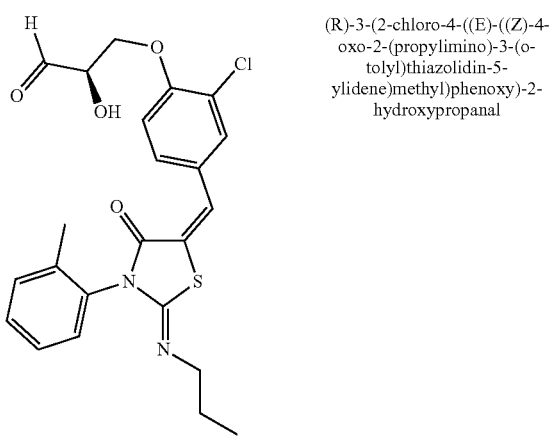 | (R)-3-(2-chloro-4-((E)-((Z)-4-oxo-2-(propylimino)-3-(o-tolyl)thiazolidin-5-ylidene)methyl)phenoxy)-2-hydroxypropanal |

| | | |
|---|---|---|
| 8I | 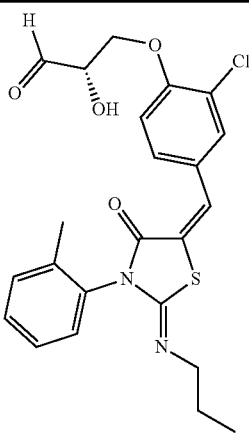 | (S)-3-(2-chloro-4-((E)-((Z)-4-oxo-2-(propylimino)-3-(o-tolyl)thiazolidin-5-ylidene)methyl)phenoxy)-2-hydroxypropanal |
| 8J | 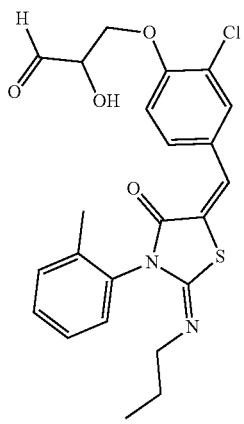 [SMILES: CCC/N=C1/S/C(=C/c2ccc(OCC(O)C=O)c(Cl)c2)C(=O)N1c1ccccc1C] | (±)-3-(2-chloro-4-((E)-((E)-4-oxo-2-(propylimino)-3-(o-tolyl)thiazolidin-5-ylidene)methyl)phenoxy)-2-hydroxypropanal |
| 8K | 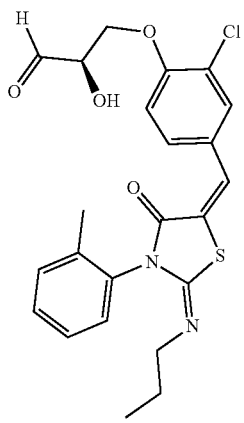 [SMILES: CCC/N=C1/S/C(=C/c2ccc(OC[C@@H](O)C=O)c(Cl)c2)C(=O)N1c1ccccc1C] | (R)-3-(2-chloro-4-((E)-((E)-4-oxo-2-(propylimino)-3-(o-tolyl)thiazolidin-5-ylidene)methyl)phenoxy)-2-hydroxypropanal |

TABLE 4-continued

| | | |
|---|---|---|
| 8L | 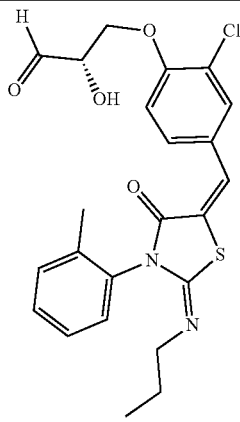 | (S)-3-(2-chloro-4-((E)-((E)-4-oxo-2-(propylimino)-3-(o-tolyl)thiazolidin-5-ylidene)methyl)phenoxy)-2-hydroxypropanal |

*Chemical Names automatically generated with ChemDraw Professional, Version 15.1.

In a fifth aspect, provided herein are compounds of Formula (IVA), compounds of Formula (IVB), compounds of Formula (IVC), compounds of Formula (IVD), compounds of Formula (IVE), compounds of Formula (IVF), compounds of Formula (IVG), and compounds of Formula (IVH). For ease of reference, the compounds of Formula (IVA), Formula (IVB), Formula (IVC), Formula (IVD), Formula (IVE), Formula (IVF), Formula (IVG), Formula (IVH) can be collectively referred to herein as the "compounds of Formula (IV)" or simply, "Formula (IV)."

Formula (IVA)

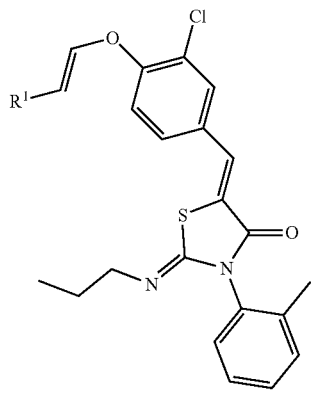

Formula (IVB)

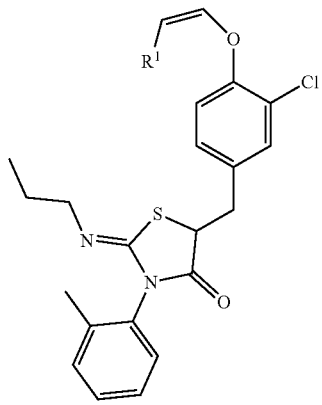

Formula (IVC)

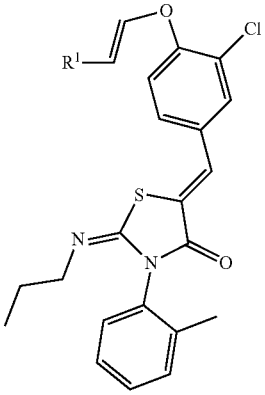

Formula (IVD)

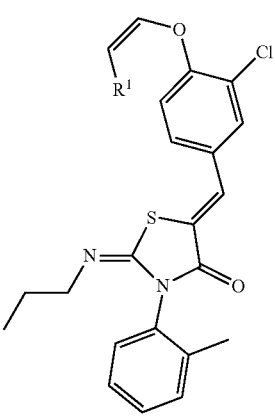

-continued

Formula (IVE)

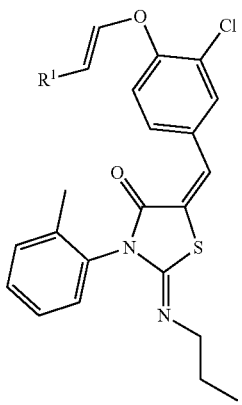

Formula (IVG)

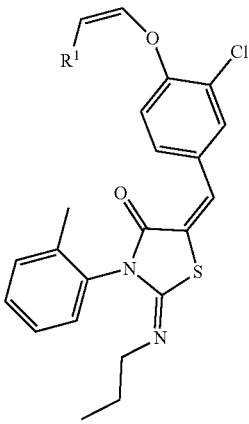

Formula (IVH)

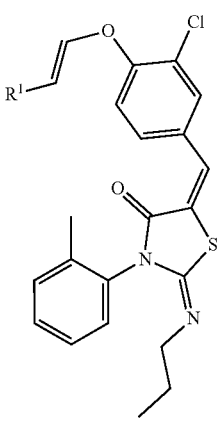

Formula (IVF)

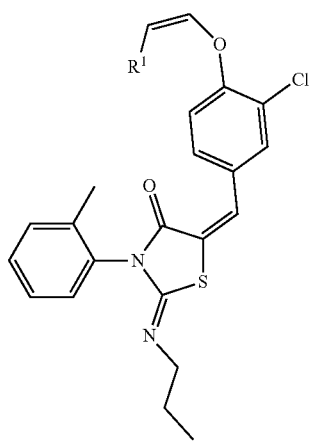

or a pharmaceutically acceptable salt, hydrate, or solvate thereof, wherein:
R$^1$ is —C(O)H or —C(O)OH.

In one embodiment, the compound of Formula (IV) is: 3-(2-chloro-4-((4-oxo-2-(propylimino)-3-(o-tolyl)thiazolidin-5-ylidene)methyl)phenoxy)acrylaldehyde (Compound 9). In one embodiment, the compound of Formula (IV) is: 3-(2-chloro-4-((4-oxo-2-(propylimino)-3-(o-tolyl)thiazolidin-5-ylidene)methyl)phenoxy)acrylic acid (Compound 10).

In an embodiment of the fifth aspect, the compounds of Formula (IV) are those wherein the compound is selected from the group consisting of the compounds in Table 5 or a pharmaceutically acceptable salt, hydrate, or solvate thereof:

TABLE 5

| | Compounds of Formula (IV) | |
|---|---|---|
| Compound No. | Compound Structure | Chemical Name* |
| 9A | | (E)-3-(2-chloro-4-((Z)-((Z)-4-oxo-2-(propylimino)-3-(o-tolyl)thiazolidin-5-ylidene)methyl)phenoxy) acrylaldehyde |
| 9B | | (Z)-3-(2-chloro-4-((Z)-((Z)-4-oxo-2-(propylimino)-3-(o-tolyl)thiazolidin-5-ylidene)methyl)phenoxy) acrylaldehyde |
| 9C | | (E)-3-(2-chloro-4-((Z)-((E)-4-oxo-2-(propylimino)-3-(o-tolyl)thiazolidin-5-ylidene)methyl)phenoxy) acrylaldehyde |

TABLE 5-continued
Compounds of Formula (IV)
| Compound No. | Compound Structure | Chemical Name* |
|---|---|---|
| 9D | 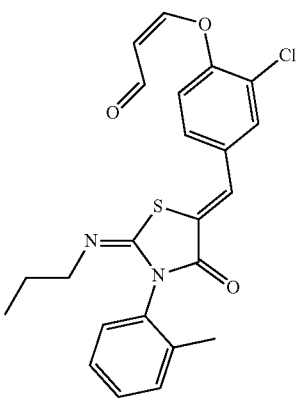 [SMILES: CCC/N=C1/S/C(=C\c2ccc(O/C=C\C=O)c(Cl)c2)C(=O)N1c1ccccc1C] | (Z)-3-(2-chloro-4-((Z)-((E)-4-oxo-2-(propylimino)-3-(o-tolyl)thiazolidin-5-ylidene)methyl)phenoxy)acrylaldehyde |
| 9E | 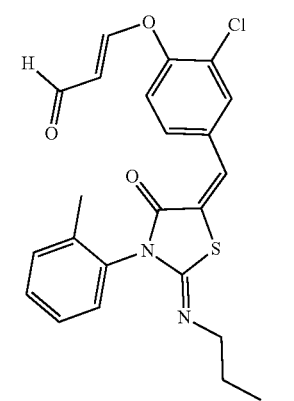 [SMILES: CCC/N=C1\S/C(=C/c2ccc(O/C=C/C=O)c(Cl)c2)C(=O)N1c1ccccc1C] | (E)-3-(2-chloro-4-((E)-((Z)-4-oxo-2-(propylimino)-3-(o-tolyl)thiazolidin-5-ylidene)methyl)phenoxy)acrylaldehyde |
| 9F | 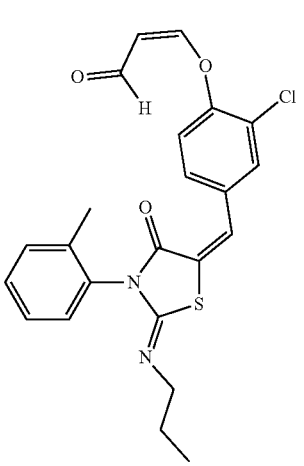 [SMILES: CCC/N=C1\S/C(=C/c2ccc(O/C=C\C=O)c(Cl)c2)C(=O)N1c1ccccc1C] | (Z)-3-(2-chloro-4-((E)-((Z)-4-oxo-2-(propylimino)-3-(o-tolyl)thiazolidin-5-ylidene)methyl)phenoxy)acrylaldehyde |

TABLE 5-continued
Compounds of Formula (IV)
| Compound No. | Compound Structure | Chemical Name* |
|---|---|---|
| 9G | 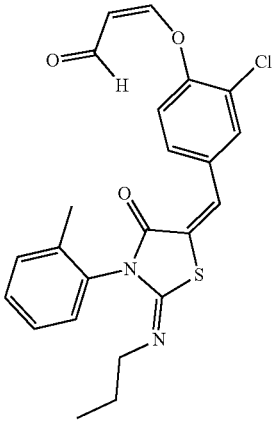 [SMILES: CCC/N=C1/S/C(=C/c2ccc(O/C=C\C=O)c(Cl)c2)C(=O)N1c1ccccc1C] | (Z)-3-(2-chloro-4-((E)-((E)-4-oxo-2-(propylimino)-3-(o-tolyl)thiazolidin-5-ylidene)methyl)phenoxy)acrylaldehyde |
| 9H | 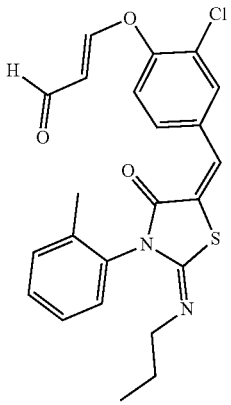 [SMILES: CCC/N=C1/S/C(=C/c2ccc(O/C=C/C=O)c(Cl)c2)C(=O)N1c1ccccc1C] | (E)-3-(2-chloro-4-((E)-((E)-4-oxo-2-(propylimino)-3-(o-tolyl)thiazolidin-5-ylidene)methyl)phenoxy)acrylaldehyde |
| 10A | 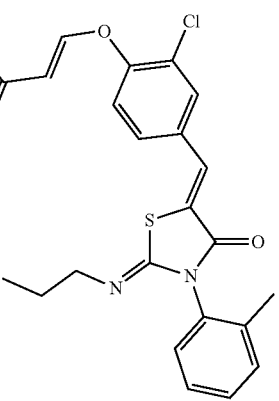 | (E)-3-(2-chloro-44(Z)-((Z)-4-oxo-2-(propylimino)-3-(o-tolyl)thiazolidin-5-ylidene)methyl)phenoxy)acrylic acid |

TABLE 5-continued

Compounds of Formula (IV)

| Compound No. | Compound Structure | Chemical Name* |
|---|---|---|
| 10B | 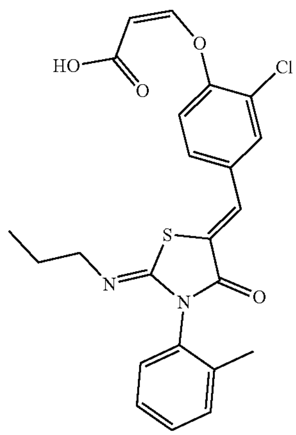 [SMILES: CCC/N=C1\S/C(=C\c2ccc(O/C=C\C(=O)O)c(Cl)c2)C(=O)N1c1ccccc1C] | (Z)-3-(2-chloro-4-((Z)-((Z)-4-oxo-2-(propylimino)-3-(o-tolyl)thiazolidin-5-ylidene)methyl)phenoxy)acrylic acid |
| 10C | 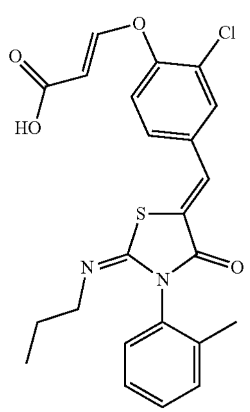 [SMILES: CCC/N=C1/S/C(=C\c2ccc(O/C=C/C(=O)O)c(Cl)c2)C(=O)N1c1ccccc1C] | (E)-3-(2-chloro-4-((-((-4-oxo-2-(propylimino)-3-(o-tolyl)thiazolidin-5-ylidene)methyl)phenoxy)acrylic acid |
| 10D | 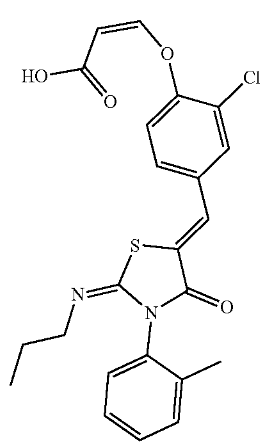 [SMILES: CCC/N=C1/S/C(=C\c2ccc(O/C=C\C(=O)O)c(Cl)c2)C(=O)N1c1ccccc1C] | (Z)-3-(2-chloro-4-((Z)-((E)-4-oxo-2-(propylimino)-3-(o-tolyl)thiazolidin-5-ylidene)methyl)phenoxy)acrylic acid |

TABLE 5-continued

Compounds of Formula (IV)

| Compound No. | Compound Structure | Chemical Name* |
|---|---|---|
| 10E | 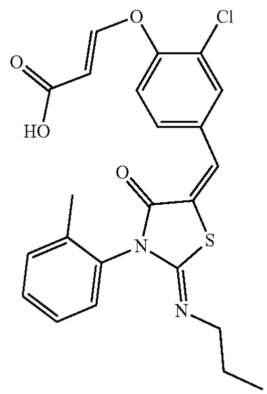 [SMILES: CCC/N=C1\S/C(=C/c2ccc(O/C=C/C(=O)O)c(Cl)c2)C(=O)N1c1ccccc1C] | (E)-3-(2-chloro-4-((E)-((Z)-4-oxo-2-(propylimino)-3-(o-tolyl)thiazolidin-5-ylidene)methyl)phenoxy)acrylic acid |
| 10F | 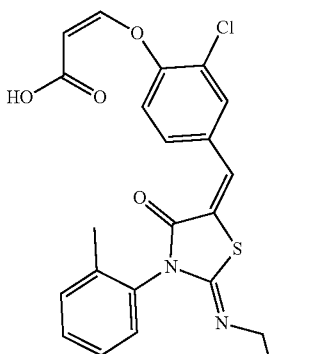 | (Z)-3-(2-chloro-4-((E)-((Z)-4-oxo-2-(propylimino)-3-(o-tolyl)thiazolidin-5-ylidene)methyl)phenoxy)acrylic acid |
| 10G | 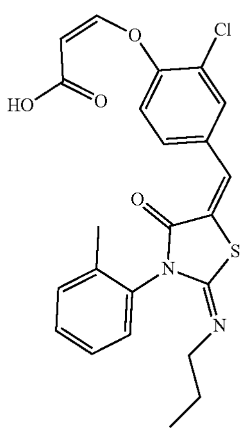 [SMILES: CCC/N=C1/S/C(=C/c2ccc(O/C=C\C(=O)O)c(Cl)c2)C(=O)N1c1ccccc1C] | (Z)-3-(2-chloro-4-((E)-((E)-4-oxo-2-(propylimino)-3-(o-tolyl)thiazolidin-5-ylidene)methyl)phenoxy)acrylic acid |

TABLE 5-continued

Compounds of Formula (IV)

| Compound No. | Compound Structure | Chemical Name* |
|---|---|---|
| 10H | 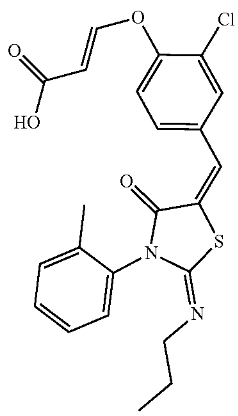 [SMILES: CCC/N=C1/S/C(=C/c2ccc(O/C=C/C(=O)O)c(Cl)c2)C(=O)N1c1ccccc1C] | (E)-3-(2-chloro-4-((E)-((E)-4-oxo-2-(propylimino)-3-(o-tolyl)thiazolidin-5-ylidene)methyl)phenoxy)acrylic acid |

*Chemical Names automatically generated with ChemDraw Professional, Version 15.1.

For the purposes of this disclosure, Table 1, Table 2, Table 3, Table 4, and Table 5 serve to define that a particular structure is associated with a particular name. Whenever a particular name is recited in this disclosure or the claims, the chemical structure associated with that particular name shall be the structure identified in Table 1, Table 2, Table 3, Table 4, and Table 5.

In a particular embodiment, the compound is selected from the group consisting of
(5-(3-chloro-4-(2,3-dihydroxypropoxy)benzylidene)-3-(o-tolyl)thiazolidine-2,4-dione) (Compound 1);
±(Z)-5-(3-chloro-4-(2,3-dihydroxypropoxy)benzylidene)-3-(o-tolyl)thiazolidine-2,4-dione (Compound 1A);
(R,Z)-5-(3-chloro-4-(2,3-dihydroxypropoxy)benzylidene)-3-(o-tolyl)thiazolidine-2,4-dione (Compound 1B);
(S,Z)-5-(3-chloro-4-(2,3-dihydroxypropoxy)benzylidene)-3-(o-tolyl)thiazolidine-2,4-dione (Compound 1C);
±(E)-5-(3-chloro-4-(2,3-dihydroxypropoxy)benzylidene)-3-(o-tolyl)thiazolidine-2,4-dione (Compound 1D);
(R,E)-5-(3-chloro-4-(2,3-dihydroxypropoxy)benzylidene)-3-(o-tolyl)thiazolidine-2,4-dione (Compound 1E); and
(S,E)-5-(3-chloro-4-(2,3-dihydroxypropoxy)benzylidene)-3-(o-tolyl)thiazolidine-2,4-dione (Compound 1F);
or a pharmaceutically acceptable salt, hydrate, or solvate thereof.

In a particular embodiment, the compound is (R,Z)-5-(3-chloro-4-(2,3-dihydroxypropoxy)benzylidene)-3-(o-tolyl)thiazolidine-2,4-dione (Compound 1B) or a pharmaceutically acceptable salt, hydrate, or solvate thereof.

In a particular embodiment, the compounds of Formula (I) are selected from the group consisting of:
5-((3-chloro-4-(2,3-dihydroxypropoxy)phenyl)(hydroxy)methyl)-2-(propylimino)-3-(o-tolyl)thiazolidin-4-one (Compound 2);
(Z)-5-((3-chloro-4-((±)-2,3-dihydroxypropoxy)phenyl)(hydroxy)methyl)-2-(propylimino)-3-(o-tolyl)thiazolidin-4-one (Compound 2A);
(Z)-5-((3-chloro-4-((R)-2,3-dihydroxypropoxy)phenyl)(hydroxy)methyl)-2-(propylimino)-3-(o-tolyl)thiazolidin-4-one (Compound 2B);
(Z)-5-((3-chloro-4-((S)-2,3-dihydroxypropoxy)phenyl)(hydroxy)methyl)-2-(propylimino)-3-(o-tolyl)thiazolidin-4-one (Compound 2C);
(E)-5-((3-chloro-4-((±)-2,3-dihydroxypropoxy)phenyl)(hydroxy)methyl)-2-(propylimino)-3-(o-tolyl)thiazolidin-4-one (Compound 2D);
(E)-5-((3-chloro-4-((R)-2,3-dihydroxypropoxy)phenyl)(hydroxy)methyl)-2-(propylimino)-3-(o-tolyl)thiazolidin-4-one (Compound 2E);
(E)-5-((3-chloro-4-((S)-2,3-dihydroxypropoxy)phenyl)(hydroxy)methyl)-2-(propylimino)-3-(o-tolyl)thiazolidin-4-one (Compound 2F);
5-(3-chloro-4-(2,3-dihydroxypropoxy)benzoyl)-2-(propylimino)-3-(o-tolyl)thiazolidin-4-one (Compound 3);
(Z)-5-(3-chloro-4-((±)-2,3-dihydroxypropoxy)benzoyl)-2-(propylimino)-3-(o-tolyl)thiazolidin-4-one (Compound 3A);
(Z)-5-(3-chloro-4-((R)-2,3-dihydroxypropoxy)benzoyl)-2-(propylimino)-3-(o-tolyl)thiazolidin-4-one (Compound 3B);
(Z)-5-(3-chloro-4-((S)-2,3-dihydroxypropoxy)benzoyl)-2-(propylimino)-3-(o-tolyl)thiazolidin-4-one (Compound 3C);
(E)-5-(3-chloro-4-((±)-2,3-dihydroxypropoxy)benzoyl)-2-(propylimino)-3-(o-tolyl)thiazolidin-4-one (Compound 3D);
(E)-5-(3-chloro-4-((R)-2,3-dihydroxypropoxy)benzoyl)-2-(propylimino)-3-(o-tolyl)thiazolidin-4-one (Compound 3E);
(E)-5-(3-chloro-4-((S)-2,3-dihydroxypropoxy)benzoyl)-2-(propylimino)-3-(o-tolyl)thiazolidin-4-one (Compound 3F);
2-(3-chloro-4-(2,3-dihydroxypropoxy)phenyl)-5-(propylimino)-6-(o-tolyl)-1-oxa-4-thia-6-azaspiro[2.4]heptan-7-one (Compound 4);
(Z)-2-(3-chloro-4-((±)-2,3-dihydroxypropoxy)phenyl)-5-(propylimino)-6-(o-tolyl)-1-oxa-4-thia-6-azaspiro[2.4]heptan-7-one (Compound 4A);
(Z)-2-(3-chloro-4-((R)-2,3-dihydroxypropoxy)phenyl)-5-(propylimino)-6-(o-tolyl)-1-oxa-4-thia-6-azaspiro[2.4]heptan-7-one (Compound 4B);
(Z)-2-(3-chloro-4-((S)-2,3-dihydroxypropoxy)phenyl)-5-(propylimino)-6-(o-tolyl)-1-oxa-4-thia-6-azaspiro[2.4]heptan-7-one (Compound 4C);

(E)-2-(3-chloro-4-((±)-2,3-dihydroxypropoxy)phenyl)-5-(propylimino)-6-(o-tolyl)-1-oxa-4-thia-6-azaspiro[2.4]heptan-7-one (Compound 4D);

(E)-2-(3-chloro-4-((R)-2,3-dihydroxypropoxy)phenyl)-5-(propylimino)-6-(o-tolyl)-1-oxa-4-thia-6-azaspiro[2.4]heptan-7-one (Compound 4E); and (E)-2-(3-chloro-4-((S)-2,3-dihydroxypropoxy)phenyl)-5-(propylimino)-6-(o-tolyl)-1-oxa-4-thia-6-azaspiro[2.4]heptan-7-one (Compound 4F);

or a pharmaceutically acceptable salt, hydrate, or solvate thereof.

In a particular embodiment, the compounds of Formula (I) are selected from the group consisting of:

(Z)-5-((3-chloro-4-((R)-2,3-dihydroxypropoxy)phenyl)(hydroxy)methyl)-2-(propylimino)-3-(o-tolyl)thiazolidin-4-one (Compound 2B);

(Z)-5-(3-chloro-4-((R)-2,3-dihydroxypropoxy)benzoyl)-2-(propylimino)-3-(o-tolyl)thiazolidin-4-one (Compound 3B); and (Z)-2-(3-chloro-4-((R)-2,3-dihydroxypropoxy)phenyl)-5-(propylimino)-6-(o-tolyl)-1-oxa-4-thia-6-azaspiro[2.4]heptan-7-one (Compound 4B);

or a pharmaceutically acceptable salt, hydrate, or solvate thereof.

In a particular embodiment, the compounds of Formula (II) are selected from the group consisting of:

5-(3-chloro-4-(2,3-dihydroxypropoxy)benzylidene)-2-(propylimino)-3-(o-tolyl)thiazolidin-4-one 1-oxide (Compound 5);

(Z)-5-((Z)-3-chloro-4-((±)-2,3-dihydroxypropoxy)benzylidene)-2-(propylimino)-3-(o-tolyl)thiazolidin-4-one 1-oxide (Compound 5A);

(Z)-5-((Z)-3-chloro-4-((R)-2,3-dihydroxypropoxy)benzylidene)-2-(propylimino)-3-(o-tolyl)thiazolidin-4-one 1-oxide (Compound 5B);

Z)-5-((Z)-3-chloro-4-((S)-2,3-dihydroxypropoxy)benzylidene)-2-(propylimino)-3-(o-tolyl)thiazolidin-4-one 1-oxide (Compound 5C);

(Z)-5-((E)-3-chloro-4-((±)-2,3-dihydroxypropoxy)benzylidene)-2-(propylimino)-3-(o-tolyl)thiazolidin-4-one 1-oxide (Compound 5D);

(Z)-5-((E)-3-chloro-4-((R)-2,3-dihydroxypropoxy)benzylidene)-2-(propylimino)-3-(o-tolyl)thiazolidin-4-one 1-oxide (Compound 5E);

(Z)-5-((E)-3-chloro-4-((S)-2,3-dihydroxypropoxy)benzylidene)-2-(propylimino)-3-(o-tolyl)thiazolidin-4-one 1-oxide (Compound 5F);

(E)-5-((Z)-3-chloro-4-((±)-2,3-dihydroxypropoxy)benzylidene)-2-(propylimino)-3-(o-tolyl)thiazolidin-4-one 1-oxide (Compound 5G);

(E)-5-((Z)-3-chloro-4-((R)-2,3-dihydroxypropoxy)benzylidene)-2-(propylimino)-3-(o-tolyl)thiazolidin-4-one 1-oxide (Compound 5H);

(E)-5-((Z)-3-chloro-4-((S)-2,3-dihydroxypropoxy)benzylidene)-2-(propylimino)-3-(o-tolyl)thiazolidin-4-one 1-oxide (Compound 5I);

(E)-5-((E)-3-chloro-4-((±)-2,3-dihydroxypropoxy)benzylidene)-2-(propylimino)-3-(o-tolyl)thiazolidin-4-one 1-oxide (Compound 5J);

(E)-5-((E)-3-chloro-4-((R)-2,3-dihydroxypropoxy)benzylidene)-2-(propylimino)-3-(o-tolyl)thiazolidin-4-one 1-oxide (Compound 5K);

(E)-5-((E)-3-chloro-4-((S)-2,3-dihydroxypropoxy)benzylidene)-2-(propylimino)-3-(o-tolyl)thiazolidin-4-one 1-oxide (Compound 5L);

5-(3-chloro-4-(2,3-dihydroxypropoxy)benzylidene)-2-(propylimino)-3-(o-tolyl)oxazolidin-4-one (Compound 6);

Z)-5-((Z)-3-chloro-4-((±)-2,3-dihydroxypropoxy)benzylidene)-2-(propylimino)-3-(o-tolyl)oxazolidin-4-one (Compound 6A);

(Z)-5-((Z)-3-chloro-4-((R)-2,3-dihydroxypropoxy)benzylidene)-2-(propylimino)-3-(o-tolyl)oxazolidin-4-one (Compound 6B);

(Z)-5-((Z)-3-chloro-4-((S)-2,3-dihydroxypropoxy)benzylidene)-2-(propylimino)-3-(o-tolyl)oxazolidin-4-one (Compound 6C);

(Z)-5-((E)-3-chloro-4-((±)-2,3-dihydroxypropoxy)benzylidene)-2-(propylimino)-3-(o-tolyl)oxazolidin-4-one (Compound 6D);

(Z)-5-((E)-3-chloro-4-((R)-2,3-dihydroxypropoxy)benzylidene)-2-(propylimino)-3-(o-tolyl)oxazolidin-4-one (Compound 6E);

(Z)-5-((E)-3-chloro-4-((S)-2,3-dihydroxypropoxy)benzylidene)-2-(propylimino)-3-(o-tolyl)oxazolidin-4-one (Compound 6F);

(E)-5-((Z)-3-chloro-4-((±)-2,3-dihydroxypropoxy)benzylidene)-2-(propylimino)-3-(o-tolyl)oxazolidin-4-one (Compound 6G);

(E)-5-((Z)-3-chloro-4-((R)-2,3-dihydroxypropoxy)benzylidene)-2-(propylimino)-3-(o-tolyl)oxazolidin-4-one (Compound 6H);

(E)-5-((Z)-3-chloro-4-((S)-2,3-dihydroxypropoxy)benzylidene)-2-(propylimino)-3-(o-tolyl)oxazolidin-4-one (Compound 6I);

(E)-5-((E)-3-chloro-4-((±)-2,3-dihydroxypropoxy)benzylidene)-2-(propylimino)-3-(o-tolyl)oxazolidin-4-one (Compound 6J);

(E)-5-((E)-3-chloro-4-((R)-2,3-dihydroxypropoxy)benzylidene)-2-(propylimino)-3-(o-tolyl)oxazolidin-4-one (Compound 6K);

(E)-5-((E)-3-chloro-4-((S)-2,3-dihydroxypropoxy)benzylidene)-2-(propylimino)-3-(o-tolyl)oxazolidin-4-one (Compound 6L);

or a pharmaceutically acceptable salt, hydrate, or solvate thereof.

In a particular embodiment, the compounds of Formula (II) are selected from the group consisting of:

(Z)-5-((Z)-3-chloro-4-((R)-2,3-dihydroxypropoxy)benzylidene)-2-(propylimino)-3-(o-tolyl)thiazolidin-4-one 1-oxide (Compound 5B); and (Z)-5-((Z)-3-chloro-4-((R)-2,3-dihydroxypropoxy)benzylidene)-2-(propylimino)-3-(o-tolyl)oxazolidin-4-one (Compound 6B);

or a pharmaceutically acceptable salt, hydrate, or solvate thereof.

In a particular embodiment, the compounds of Formula (III) are selected from the group consisting of:

5-(3-chloro-4-(3-hydroxy-2-oxopropoxy)benzylidene)-2-(propylimino)-3-(o-tolyl)thiazolidin-4-one (Compound 7);

(Z)-5-((Z)-3-chloro-4-(3-hydroxy-2-oxopropoxy)benzylidene)-2-(propylimino)-3-(o-tolyl)thiazolidin-4-one (Compound 7A);

(Z)-5-((E)-3-chloro-4-(3-hydroxy-2-oxopropoxy)benzylidene)-2-(propylimino)-3-(o-tolyl)thiazolidin-4-one (Compound 7B);

(E)-5-((Z)-3-chloro-4-(3-hydroxy-2-oxopropoxy)benzylidene)-2-(propylimino)-3-(o-tolyl)thiazolidin-4-one (Compound 7C);

(E)-5-((E)-3-chloro-4-(3-hydroxy-2-oxopropoxy)benzylidene)-2-(propylimino)-3-(o-tolyl)thiazolidin-4-one (Compound 7D);

3-(2-chloro-4-((4-oxo-2-(propylimino)-3-(o-tolyl)thiazolidin-5-ylidene)methyl)phenoxy)-2-hydroxypropanal (Compound 8);

(±)-3-(2-chloro-4-((Z)—((Z)-4-oxo-2-(propylimino)-3-(o-tolyl)thiazolidin-5-ylidene)methyl)phenoxy)-2-hydroxypropanal (Compound 8A);

(S)-3-(2-chloro-4-((Z)—((Z)-4-oxo-2-(propylimino)-3-(o-tolyl)thiazolidin-5-ylidene)methyl)phenoxy)-2-hydroxypropanal (Compound 8B);

(R)-3-(2-chloro-4-((Z)—((Z)-4-oxo-2-(propylimino)-3-(o-tolyl)thiazolidin-5-ylidene)methyl)phenoxy)-2-hydroxypropanal (Compound 8C);

(±)-3-(2-chloro-4-((Z)—((E)-4-oxo-2-(propylimino)-3-(o-tolyl)thiazolidin-5-ylidene)methyl)phenoxy)-2-hydroxypropanal (Compound 8D);

(S)-3-(2-chloro-4-((Z)—((E)-4-oxo-2-(propylimino)-3-(o-tolyl)thiazolidin-5-ylidene)methyl)phenoxy)-2-hydroxypropanal (Compound 8E);

(R)-3-(2-chloro-4-((Z)—((E)-4-oxo-2-(propylimino)-3-(o-tolyl)thiazolidin-5-ylidene)methyl)phenoxy)-2-hydroxypropanal (Compound 8F);

(±)-3-(2-chloro-4-((E)-((Z)-4-oxo-2-(propylimino)-3-(o-tolyl)thiazolidin-5-ylidene)methyl)phenoxy)-2-hydroxypropanal (Compound 8G);

(R)-3-(2-chloro-4-((E)-((Z)-4-oxo-2-(propylimino)-3-(o-tolyl)thiazolidin-5-ylidene)methyl)phenoxy)-2-hydroxypropanal (Compound 8H);

(S)-3-(2-chloro-4-((E)-((Z)-4-oxo-2-(propylimino)-3-(o-tolyl)thiazolidin-5-ylidene)methyl)phenoxy)-2-hydroxypropanal (Compound 8I);

(±)-3-(2-chloro-4-((E)-((E)-4-oxo-2-(propylimino)-3-(o-tolyl)thiazolidin-5-ylidene)methyl)phenoxy)-2-hydroxypropanal (Compound 8J);

(R)-3-(2-chloro-4-((E)-((E)-4-oxo-2-(propylimino)-3-(o-tolyl)thiazolidin-5-ylidene)methyl)phenoxy)-2-hydroxypropanal (Compound 8K);

(S)-3-(2-chloro-4-((E)-((E)-4-oxo-2-(propylimino)-3-(o-tolyl)thiazolidin-5-ylidene)methyl)phenoxy)-2-hydroxypropanal (Compound 8L);

or a pharmaceutically acceptable salt, hydrate, or solvate thereof.

In a particular embodiment, the compounds of Formula (III) are selected from the group consisting of:

(Z)-5-((Z)-3-chloro-4-(3-hydroxy-2-oxopropoxy)benzylidene)-2-(propylimino)-3-(o-tolyl)thiazolidin-4-one (Compound 7A); and (S)-3-(2-chloro-4-((Z)—((Z)-4-oxo-2-(propylimino)-3-(o-tolyl)thiazolidin-5-ylidene)methyl)phenoxy)-2-hydroxypropanal (Compound 8B);

or a pharmaceutically acceptable salt, hydrate, or solvate thereof.

In a particular embodiment, the compounds of Formula (IV) are selected from the group consisting of:

3-(2-chloro-4-((4-oxo-2-(propylimino)-3-(o-tolyl)thiazolidin-5-ylidene)methyl)phenoxy)acrylaldehyde (Compound 9);

(E)-3-(2-chloro-4-((Z)—((Z)-4-oxo-2-(propylimino)-3-(o-tolyl)thiazolidin-5-ylidene)methyl)phenoxy)acrylaldehyde (Compound 9A);

(Z)-3-(2-chloro-4-((Z)—((Z)-4-oxo-2-(propylimino)-3-(o-tolyl)thiazolidin-5-ylidene)methyl)phenoxy)acrylaldehyde (Compound 9B);

(E)-3-(2-chloro-4-((Z)—((E)-4-oxo-2-(propylimino)-3-(o-tolyl)thiazolidin-5-ylidene)methyl)phenoxy)acrylaldehyde (Compound 9C);

(Z)-3-(2-chloro-4-((Z)—((E)-4-oxo-2-(propylimino)-3-(o-tolyl)thiazolidin-5-ylidene)methyl)phenoxy)acrylaldehyde (Compound 9D);

(E)-3-(2-chloro-4-((E)-(Z)-4-oxo-2-(propylimino)-3-(o-tolyl)thiazolidin-5-ylidene)methyl)phenoxy)acrylaldehyde (Compound 9E);

Z)-3-(2-chloro-4-((E)-((Z)-4-oxo-2-(propylimino)-3-(o-tolyl)thiazolidin-5-ylidene)methyl)phenoxy)acrylaldehyde (Compound 9F);

(Z)-3-(2-chloro-4-((E)-((E)-4-oxo-2-(propylimino)-3-(o-tolyl)thiazolidin-5-ylidene)methyl)phenoxy)acrylaldehyde (Compound 9G);

(E)-3-(2-chloro-4-((E)-((E)-4-oxo-2-(propylimino)-3-(o-tolyl)thiazolidin-5-ylidene)methyl)phenoxy)acrylaldehyde (Compound 9H);

3-(2-chloro-4-((4-oxo-2-(propylimino)-3-(o-tolyl)thiazolidin-5-ylidene)methyl)phenoxy)acrylic acid (Compound 10);

(E)-3-(2-chloro-4-((Z)—((Z)-4-oxo-2-(propylimino)-3-(o-tolyl)thiazolidin-5-ylidene)methyl)phenoxy)acrylic acid (Compound 10A);

(Z)-3-(2-chloro-4-((Z)—((Z)-4-oxo-2-(propylimino)-3-(o-tolyl)thiazolidin-5-ylidene)methyl)phenoxy)acrylic acid (Compound 10B);

(E)-3-(2-chloro-4-((Z)—((E)-4-oxo-2-(propylimino)-3-(o-tolyl)thiazolidin-5-ylidene)methyl)phenoxy)acrylic acid (Compound 10C);

(Z)-3-(2-chloro-4-((Z)—((E)-4-oxo-2-(propylimino)-3-(o-tolyl)thiazolidin-5-ylidene)methyl)phenoxy)acrylic acid (Compound 10D);

(E)-3-(2-chloro-4-((E)-((Z)-4-oxo-2-(propylimino)-3-(o-tolyl)thiazolidin-5-ylidene)methyl)phenoxy)acrylic acid (Compound 10E);

(Z)-3-(2-chloro-4-((E)-((Z)-4-oxo-2-(propylimino)-3-(o-tolyl)thiazolidin-5-ylidene)methyl)phenoxy)acrylic acid (Compound 10F);

(Z)-3-(2-chloro-4-((E)-((E)-4-oxo-2-(propylimino)-3-(o-tolyl)thiazolidin-5-ylidene)methyl)phenoxy)acrylic acid (Compound 10G);

(E)-3-(2-chloro-4-((E)-((E)-4-oxo-2-(propylimino)-3-(o-tolyl)thiazolidin-5-ylidene)methyl)phenoxy)acrylic acid (Compound 10H);

or a pharmaceutically acceptable salt, hydrate, or solvate thereof.

In a particular embodiment, the compounds of Formula (IV) are selected from the group consisting of:

(E)-3-(2-chloro-4-((Z)—((Z)-4-oxo-2-(propylimino)-3-(o-tolyl)thiazolidin-5-ylidene)methyl)phenoxy)acrylaldehyde (Compound 9A); and (E)-3-(2-chloro-4-((Z)—((Z)-4-oxo-2-(propylimino)-3-(o-tolyl)thiazolidin-5-ylidene)methyl)phenoxy)acrylic acid (Compound 10A);

or a pharmaceutically acceptable salt, hydrate, or solvate thereof.

4.3 Methods of Synthesizing Compounds

The following represent exemplary methods of synthesizing various compounds disclosed herein. Although particular stereochemical configurations may be depicted below, a person of ordinary skill in the art would appreciate that the compounds disclosed herein can be made as mixes of diastereomers and subsequently separated by, e.g., achiral high performance liquid chromatography (HPLC), or that that compounds disclosed herein can be made as enantiomers and subsequently separated by, e.g., chiral HPLC or supercritical fluid chromatography (SFC).

4.3.1 Compound 1

The compound of Formula (I) described herein may be synthesized using conventional methods known to those of ordinary skill in the art and commercially available materials. For example, Compound 1B described herein can be prepared as outlined in Scheme 1 shown below. It should be noted that one skilled in the art can modify the procedures set forth in the illustrative schemes and examples to arrive at the desired product.

As shown in Scheme 1, Compound A and Compound B can be reacted to form thiazolidine-2,4-dione C. Compound C can be reacted with Compound D under Knoevenagel conditions, such as acetic acid/sodium acetate, to form Compound 1B.

Scheme 1

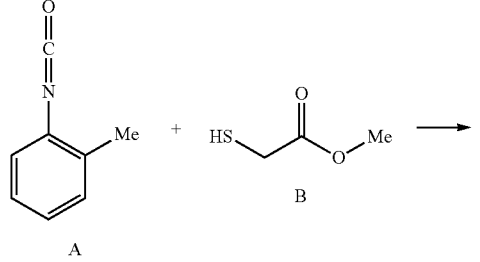

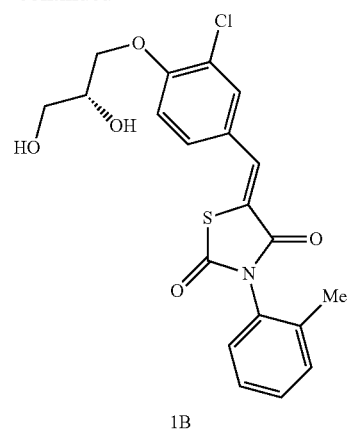

1B

4.3.2 Compounds of Formula (I)

The compounds of Formula (I) described herein may be synthesized using conventional methods known to those of ordinary skill in the art and commercially available materials. For example, particular compounds of Formula (I) described herein can be prepared as outlined in Schemes 2-4 shown below. It should be noted that one skilled in the art can modify the procedures set forth in the illustrative schemes and examples to arrive at the desired product.

As shown in Scheme 2, Compounds E and D can be reacted under aldol conditions to yield Compound 2B.

Scheme 2

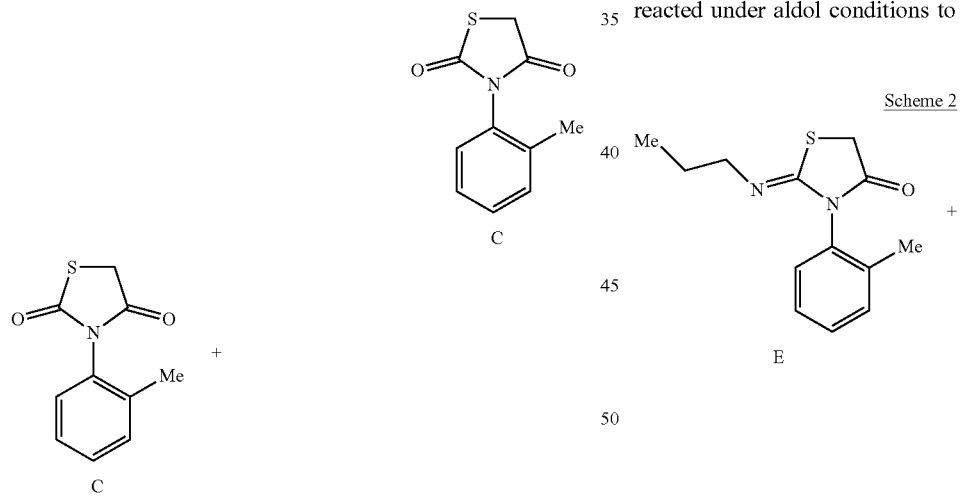

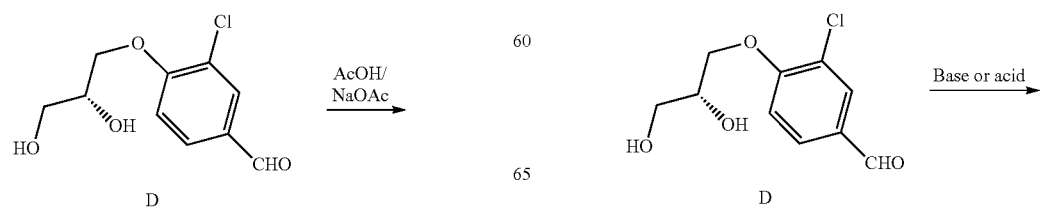

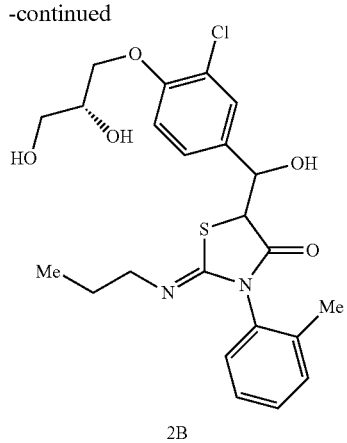
2B
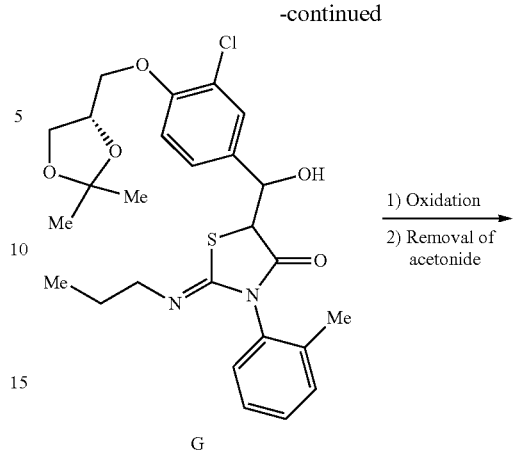
G
As shown in Scheme 3, Compound E and Compound F (acetonide protected Compound D) can be reacted under aldol conditions to yield Compound G. The benzylic alcohol of Compound G can be oxidized, followed by removal of the acetonide group, to yield Compound 3B.
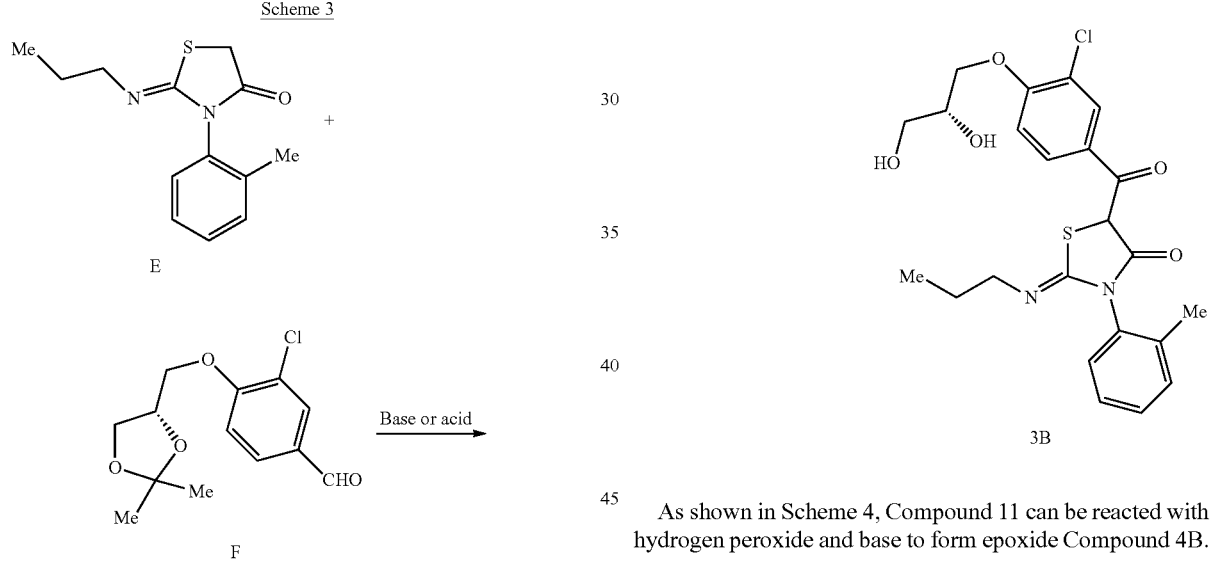
3B
As shown in Scheme 4, Compound 11 can be reacted with hydrogen peroxide and base to form epoxide Compound 4B.
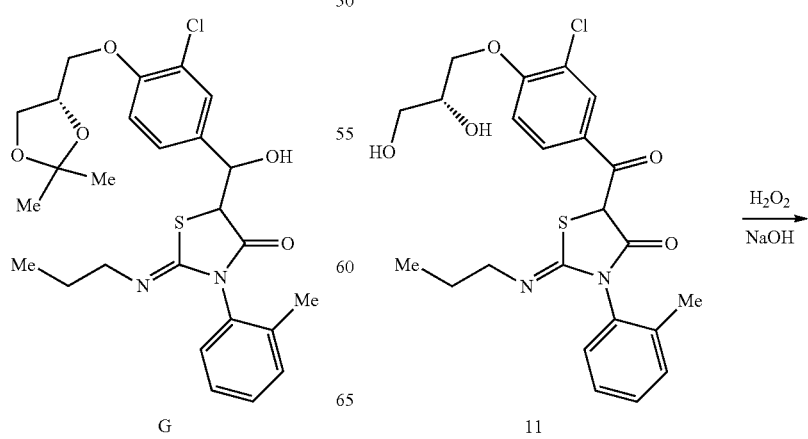

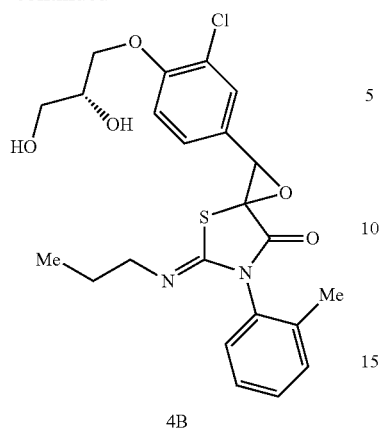

4B

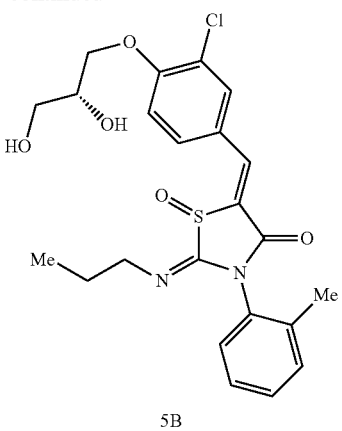

5B

4.3.3 Compounds of Formula (II)

The compounds of Formula (II) described herein may be synthesized using conventional methods known to those of ordinary skill in the art and commercially available materials. For example, particular compounds of Formula (II) described herein can be prepared as outlined in Schemes 5-6 shown below. It should be noted that one skilled in the art can modify the procedures set forth in the illustrative schemes and examples to arrive at the desired product.

As shown in Scheme 5, Compound 11 can oxidized, e.g., with m-chloroperbenzoic acid or oxygen, to form sulfoxide Compound 5B.

As shown in Scheme 6, the mixed urea Compound I can be reacted with bromoacetyl bromide Compound J in the presence of base to form Compound K. Compound K can be reacted with aldehyde D under Knoevenagel conditions, such as acetic acid/sodium acetate, to form Compound 6B.

Scheme 6

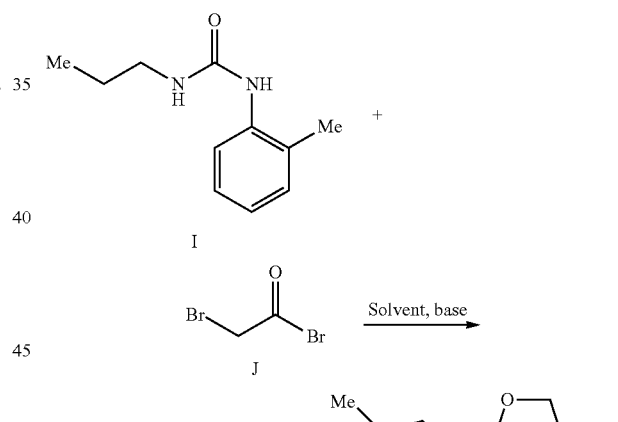

Scheme 5

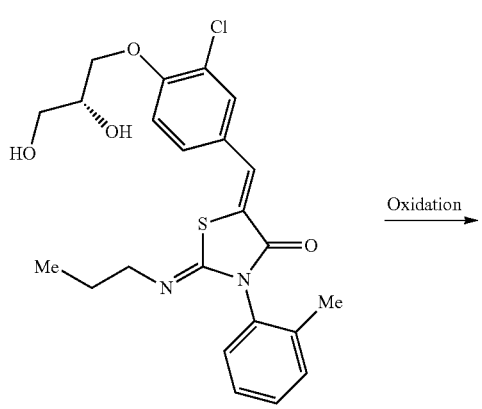

11

-continued

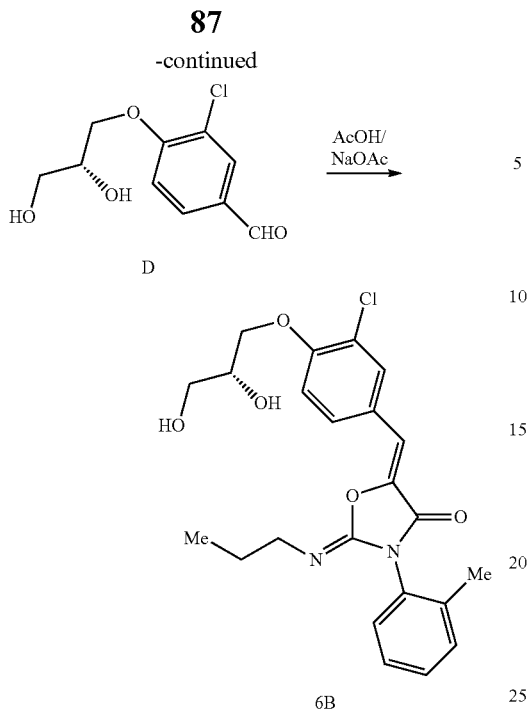

D

6B

4.3.4 Compounds of Formula (III)

The compounds of Formula (III) described herein may be synthesized using conventional methods known to those of ordinary skill in the art and commercially available materials. For example, particular compounds of Formula (III) described herein can be prepared as outlined in Schemes 7-8 shown below. It should be noted that one skilled in the art can modify the procedures set forth in the illustrative schemes and examples to arrive at the desired product.

As shown in Scheme 7, the primary alcohol of the Compound (±)-11 can be protected via reaction with acetic anhydride, followed by oxidation of the secondary alcohol with Dess Martin periodinane. Subsequent removal of the primary acetate with methanolic sodium hydroxide can yield compound 7A.

-continued

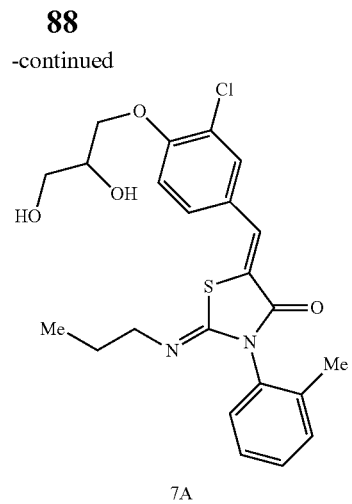

7A

As shown in Scheme 8, the known Compound 11 can be reacted with Bobbit's reagent (Compound M) to yield the aldehyde Compound 8B.

Scheme 8

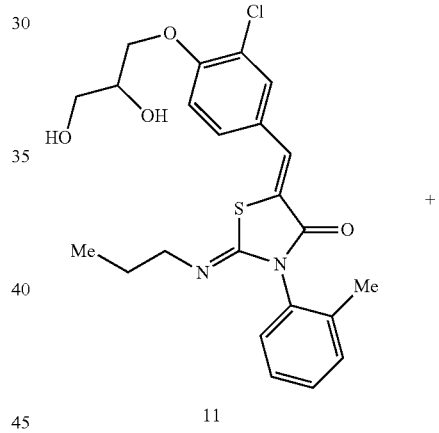

11

Scheme 7

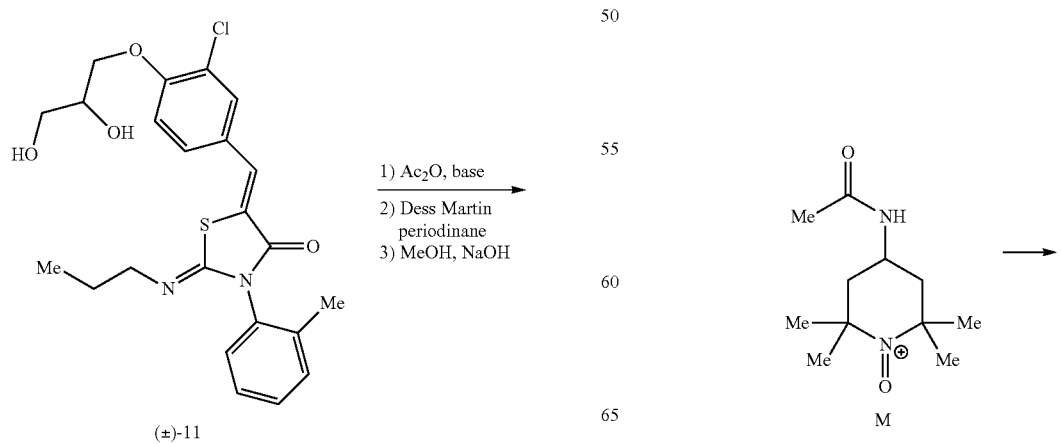

(±)-11

M

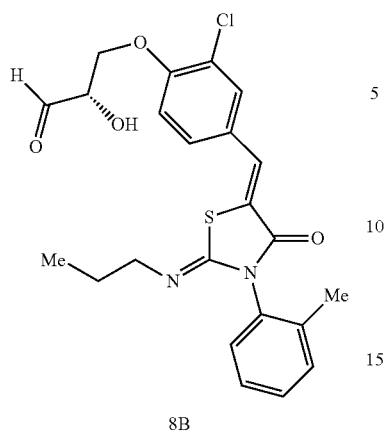

8B

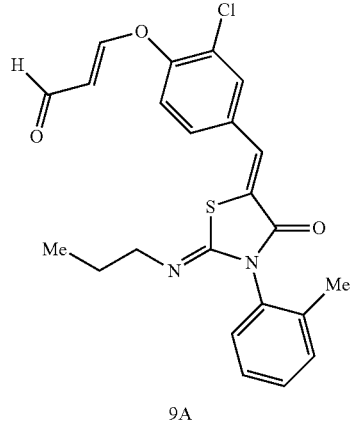

9A

As shown in Scheme 10, Compound 9A can be treated with an oxidant, for example, silver (I) oxide, to yield Compound 10.

Scheme 10

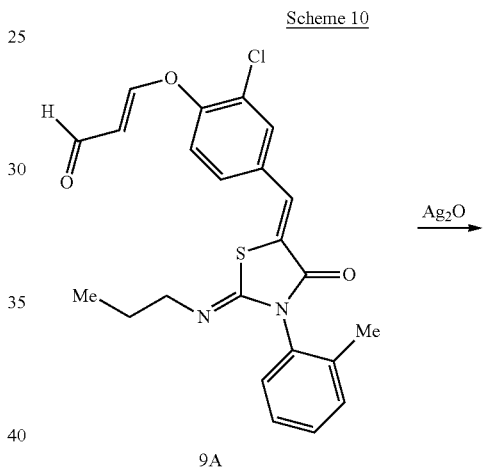

4.3.5 Compounds of Formula (IV)

The compounds of Formula (IV) described herein may be synthesized using conventional methods known to those of ordinary skill in the art and commercially available materials. For example, particular compounds of Formula (IV) described herein can be prepared as outlined in Schemes 9-10 shown below. It should be noted that one skilled in the art can modify the procedures set forth in the illustrative schemes and examples to arrive at the desired product.

As shown in Scheme 9, Compound 8 can be treated with methanesulfonyl chloride and pyridine to yield Compound 9A.

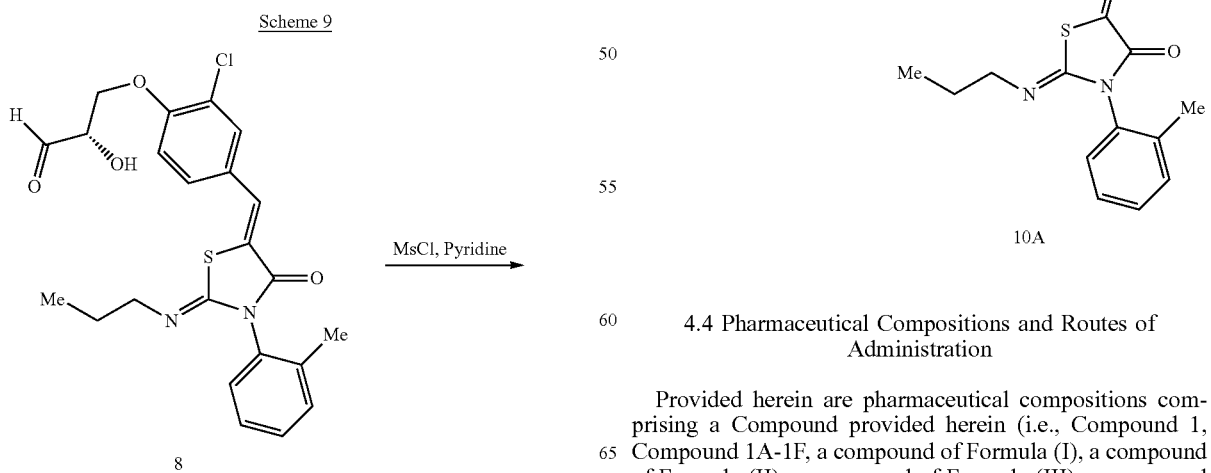

4.4 Pharmaceutical Compositions and Routes of Administration

Provided herein are pharmaceutical compositions comprising a Compound provided herein (i.e., Compound 1, Compound 1A-1F, a compound of Formula (I), a compound of Formula (II), a compound of Formula (III), a compound of Formula (IV), a compound listed in Table 1, a compound listed in Table 2, a compound listed in Table 3, a compound listed in Table 4, or a compound listed in Table 5), including a pharmaceutically acceptable salt, solvate, or hydrate thereof. In one embodiment, the Compound is an active pharmaceutical ingredient.

In one embodiment, provided herein are pharmaceutical formulations comprising a Compound or a pharmaceutically acceptable salt, solvate, or hydrate thereof in combination with a pharmaceutically acceptable vehicle, carrier, diluent, or excipient, or a mixture thereof. In one embodiment, the Compound is an active pharmaceutical ingredient.

In one embodiment, a pharmaceutical composition comprises any combination of Compounds, or a pharmaceutically acceptable salt, solvate, or hydrate thereof. In one embodiment, at least one compound of the combination of Compounds is an active pharmaceutical ingredient.

In one embodiment, a pharmaceutical formulation comprises any combination of Compounds, as active ingredients, or a pharmaceutically acceptable salt, solvate, or hydrate thereof in combination with a pharmaceutically acceptable vehicle, carrier, diluent, or excipient, or a mixture thereof. In one embodiment, at least one compound of the combination of Compounds is an active pharmaceutical ingredient.

Provided herein are pharmaceutical compositions comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or thereof.

In one embodiment, a pharmaceutical formulation comprises a Compound or a pharmaceutically acceptable salt, solvate, or hydrate thereof and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or thereof in combination with a pharmaceutically acceptable vehicle, carrier, diluent, or excipient, or a mixture thereof.

Provided herein are pharmaceutical compositions comprising any combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or thereof.

In one embodiment, a pharmaceutical formulation comprises any combination of Compounds or a pharmaceutically acceptable salt, solvate, or hydrate thereof and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or thereof in combination with a pharmaceutically acceptable vehicle, carrier, diluent, or excipient, or a mixture thereof.

In certain embodiments, the Compound or combination of Compounds is in the form of a hydrochloride salt, hydrobromide salt, napadisylate salt, 2-naphthalenesulfonate salt, edisylate salt, p-toluenesulfonate salt, trifluoroacetate salt, or ethanesulfonate salt. In certain embodiments, the Compound is in the form of a hydrochloride salt, hydrobromide salt, napadisylate salt, 2-naphthalenesulfonate salt, or edisylate salt. In certain embodiments, the Compound is in the form of a free base.

In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrobromide salt, napadisylate salt, 2-naphthalenesulfonate salt, edisylate salt, p-toluenesulfonate salt, trifluoroacetate salt, or ethanesulfonate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a free base.

In certain embodiments, a pharmaceutical formulations provided herein further comprise a pharmaceutically acceptable carrier.

4.4.1 Additional Active Pharmaceutical Ingredients (APIs)

In certain embodiments, the compositions or formulations described herein can be combined with one or more additional active pharmaceutical ingredients. In certain embodiments, the additional active can be selected from the group comprising or consisting of immunosuppressants, corticosteroids, nonsteroidal anti-inflammatory drugs, cytotoxic drugs, adhesion molecule inhibitors, cytokines, cytokine inhibitors, cytokine receptor antagonists and recombinant cytokine receptors.

In certain embodiments, the additional active can be an immunosuppressant agent. In certain embodiments, the additional active can be selected from the group consisting of cyclosporin, daclizumab, basiliximab, everolimus, tacrolimus (FK506), azathiopirene, leflunomide, and 15-deoxyspergualin.

In certain embodiments, the additional active can be selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl) ethyl methyl (2E)but-2-ene-1,4-dioate, or a pharmaceutically acceptable salt thereof.

In certain embodiments, the additional active pharmaceutical ingredient can be administered simultaneously, separately, or sequentially with the Compounds, pharmaceutical compostions, and pharmaceutical formulations disclosed herein. In certain embodiments, the additional active pharmaceutical ingredient can be administered simultaneously, with the Compounds, pharmaceutical compostions, and pharmaceutical formulations disclosed herein. In certain embodiments, the additional active pharmaceutical ingredient can be administered simultaneously in the same dosage form. In certain embodiments, the additional active pharmaceutical ingredient can be administered simultaneously in the separate dosage forms. In certain embodiments, the additional active pharmaceutical ingredient can be administered separately with Compounds, pharmaceutical compostions, and pharmaceutical formulations disclosed herein.

4.4.2 Oral Administration

The pharmaceutical compositions provided herein may be administered orally, for example in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, the pharmaceutically acceptable carrier or excipient is selected from the group consisting of lactose (e.g., as lactose monohydrate); microcrystalline cellulose; non-basic polymers (e.g., homopolymers of cross-linked N-vinyl-2-pyrrolidone (crospovidone), hypromellose (hydroxypropylmethyl cellulose), and ethyl cellulose); waxes; colloidal silicon dioxide; stearic acid; hydrogenated vegetable oil; mineral oil; polyethylene glycol (e.g., polyethylene glycol 4000-6000); glyceryl palmitostearate; and glyceryl behenate. In another embodiment, the pharmaceutically acceptable carrier or excipient is microcrystalline cellulose.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1% to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN®20), polyoxyethylene sorbitan monooleate 80 (TWEEN®80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets. In one embodiment, the pharmaceutical composition is in the form of a tablet. In another embodiment, the pharmaceutical composition is in the form of a film-coated tablet.

4.4.3 Parenteral Administration

The pharmaceutical compositions provided herein can be administered parenterally, for example, by injection, infusion, or implantation techniques, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/ vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

4.4.4 Dosing Regimens

In certain embodiments, a dose of the Compound, combination of Compounds, Compound 11, Compound+Compound 11, and/or combination of Compounds+Compound 11 in the pharmaceutical composition is between about 0.1 mg and about 1000 mg per day. In certain embodiments, the dose is between about 0.1 mg and about 500 mg per day. In certain embodiments, the dose is between about 0.5 mg and about 500 mg per day. In certain embodiments, the dose is between about 0.1 mg and about 200 mg per day. In certain embodiments, the dose is between about 0.1 mg and about 100 mg per day. In certain embodiments, the dose is between about 0.1 mg and about 50 mg per day. In certain embodiments, the dose is between about 0.1 mg and about 30 mg per day. In certain embodiments, the dose is between about 0.1 mg and about 20 mg per day. In certain embodiments, the dose is between about 0.5 mg and about 20 mg per day. In certain embodiments, the dose is between about 1 mg and about 20 mg per day. In certain embodiments, the dose is between about 1 mg and about 15 mg per day. In certain embodiments, the dose is between about 1 mg and about 10 mg per day. In certain embodiments, the dose is between about 1 mg and about 5 mg per day. In certain embodiments, the dose is between about 1 mg and about 500 mg per day. In certain embodiments, the dose is between about 5 mg and about 200 mg per day.

In certain embodiments, a maintenance dose of the Compound, combination of Compounds, Compound 11, Compound+Compound 11, and/or combination of Compounds+ Compound 11 in the pharmaceutical composition is between about 0.1 mg and about 20 mg orally once daily. In certain embodiments, the maintenance dose is between about 0.5 mg and about 20 mg orally once daily. In certain embodiments, the maintenance dose is between about 0.1 mg and about 15 mg orally once daily. In certain embodiments, the maintenance dose is between about 0.5 mg and about 15 mg orally once daily. In certain embodiments, the maintenance dose is between about 0.1 mg and about 10 mg orally once daily. In certain embodiments, the maintenance dose is between about 0.5 mg and about 10 mg orally once daily. In certain embodiments, the maintenance dose is between about 0.1 mg and about 5 mg orally once daily. In certain embodiments, the maintenance dose is between about 0.5 mg and about 5 mg orally once daily.

In certain embodiments, a maintenance dose of the Compound, combination of Compounds, Compound 11, Compound+Compound 11, and/or combination of Compounds+ Compound 11 in the pharmaceutical composition is about 10 mg or about 20 mg orally once daily. In certain embodiments, the maintenance dose is about 20 mg orally once daily. In certain embodiments, the maintenance dose is 20 mg once daily. In certain embodiments, the maintenance dose is 20 mg administered as a monotherapy.

In certain embodiments, the Compound, combination of Compounds, Compound 11, Compound+Compound 11, and/or combination of Compounds+Compound 11 can be administered orally once daily a dose of about 10 mg for 7 days followed by about 20 mg on day 8.

In certain embodiments, the dosing regimen can comprise administration of: about 2 mg of the Compound, combination of Compounds, Compound 11, Compound+Compound 11, and/or combination of Compounds+Compound 11 on days 1 and 2; about 3 mg on days 3 and 4; about 4 mg on days 5 and 6; about 5 mg of the on day 7; about 6 mg on day 8; about 7 mg of on day 9; about 8 mg on day 10; and about 9 mg on day 11; followed by: (a) a maintenance dose of about 10 mg of the Compound, combination of Compounds, Compound 11, Compound+Compound 11, and/or combination of Compounds+Compound 11 administered orally once daily from day 12 onwards; or (b) about 10 mg administered orally once daily for 2, 3 or 4 days (i.e., on days 12 and 13; days 12, 13, and 14; or days 12, 13, 14, and 15), or for 3 days (i.e., on days 12, 13, and 14), followed by a maintenance dose of about 20 mg administered orally once daily (i.e., from the day following the day of the last administration of the about 10 mg dose onwards).

In certain embodiments, the dosing regimen can comprise administration of: about 2 mg of the Compound, combination of Compounds, Compound 11, Compound+Compound 11, and/or combination of Compounds+Compound 11 on days 1 and 2; about 3 mg on days 3 and 4; about 4 mg on days 5 and 6; about 5 mg on day 7; about 6 mg on day 8; about 7 mg on day 9; about 8 mg on day 10; and about 9 mg on day 11; followed by about 10 mg of the Compound, combination of Compounds, Compound 11, Compound+ Compound 11, and/or combination of Compounds+Compound 11 administered orally once daily for 2, 3 or 4 days; followed by the maintenance dose of about 20 mg administered orally once daily.

In certain embodiments, about 10 mg of the Compound, combination of Compounds, Compound 11, Compound+ Compound 11, and/or combination of Compounds+Compound 11 can be administered orally once daily on days 12, 13, and 14; followed by a maintenance dose of 20 mg administered orally once daily from day 15 onwards.

In certain embodiments, the dosing regimen can comprise administration of: about 2 mg of the Compound, combination of Compounds, Compound 11, Compound+Compound 11, and/or combination of Compounds+Compound 11 on days 1 and 2; about 3 mg on days 3 and 4; about 4 mg on days 5 and 6; about 5 mg on day 7; about 6 mg on day 8; about 7 mg day 9; about 8 mg on day 10; and about 9 mg on day 11; followed by the maintenance dose of about 10 mg of the Compound, combination of Compounds, Compound 11, Compound+Compound 11, and/or combination of Compounds+Compound 11 administered orally once daily from day 12 onwards.

For clarity reasons, it is noted that the doses referred to herein i) refer to the amount of the Compounds or Compound 11 in their free form. In case that for example a pharmaceutically acceptable salt of the Compounds and/or Compound 11 is used, the amounts given above will need to be adapted accordingly.

4.5 Methods of Treatment

Provided herein are methods for treating a subject suffering from or at risk of a disease or disorder associated with an activated immune system, or a disease or disorder that can be treated and/or prevented with a selective S1P1 receptor agonist, wherein the method comprises administering to said subject a therapeutically effective amount of a Compound (i.e., Compound 1, Compound 1A-1F, a compound of Formula (I), a compound of Formula (II), a compound of Formula (III), a compound of Formula (IV), a compound listed in Table 1, a compound listed in Table 2, a compound listed in Table 3, or a compound listed in Table 4), or a pharmaceutically acceptable salt, hydrate, or solvate thereof.

In certain embodiments, the method for treating a subject suffering from or at risk of having a disease or disorder associated with an activated immune system, or a disease or disorder can be treated and/or prevented with a selective S1P1 receptor agonist comprises administering to said subject a therapeutically effective amount any combination of Compounds, or a pharmaceutically acceptable salt, hydrate, or solvates thereof.

In certain embodiments, the method for treating a subject suffering from or at risk having of a disease or disorder associated with an activated immune system, or a disease or disorder that can be treated and/or prevented with a selective S1P1 receptor agonist comprises administering to said subject a therapeutically effective amount of a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk having of a disease or disorder associated with an activated immune system, or a disease or disorder that can be treated and/or prevented with a selective S1P1 receptor agonist comprises administering to said subject a therapeutically effective amount of any combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk having of a disease or disorder associated with an activated immune system, or a disease or disorder that can be treated and/or prevented with a selective S1P1 receptor agonist comprises administering to said subject a therapeutically effective amount of a pharmaceutical composition comprising a Compound or a pharmaceutically acceptable salt, solvate, or hydrate thereof.

In certain embodiments, the method for treating a subject suffering from or at risk of having a disease or disorder associated with an activated immune system, or a disease or disorder can be treated and/or prevented with a selective S1P1 receptor agonist comprises administering to said subject a therapeutically effective amount of a pharmaceutical formulation comprising a Compound or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having a disease or disorder associated with an activated immune system, or a disease or disorder that can be treated and/or prevented with a selective S1P1 receptor agonist comprises administering to said subject a therapeutically effective amount of a pharmaceutical composition comprising a combination of Compounds, or a pharmaceutically acceptable salt, hydrate, or solvate thereof.

In certain embodiments, the method for treating a subject suffering from or at risk of having a disease or disorder associated with an activated immune system, or a disease or disorder that can be treated and/or prevented with a selective S1P1 receptor agonist comprises administering to said subject a therapeutically effective amount of a pharmaceutical formulation comprising any combination of Compounds, or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having a disease or disorder associated with an activated immune system, or a disease or disorder can be treated and/or prevented with a selective S1P1 receptor agonist comprises administering to said subject a therapeutically effective amount of a pharmaceutical composition comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having a disease or disorder associated with an activated immune system, or a disease or disorder can be treated and/or prevented with a selective S1P1 receptor agonist comprises administering to said subject a therapeutically effective amount of a pharmaceutical formulation comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the method for treating a subject suffering from or at risk of having a disease or disorder associated with an activated immune system, or a disease or disorder that can be treated and/or prevented with a selective S1P1 receptor agonist comprises administering to said subject a therapeutically effective amount of a pharmaceutical composition comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having a disease or disorder associated with an activated immune system, or a disease or disorder that can be treated and/or prevented with a selective S1P1 receptor agonist comprises administering to said subject a therapeutically effective amount of a pharmaceutical formulation comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the Compound or any combination of Compounds in the pharmaceutical compositions and/or pharmaceutical formulations is in the form of a of hydrochloride salt, hydrobromide salt, napadisylate salt, 2-naphthalenesulfonate salt, edisylate salt, p-toluenesulfonate salt, trifluoroacetate salt, or ethanesulfonate salt. In certain embodiments, the combination of Compounds is in the form of a hydrochloride salt, hydrobromide salt, napadisylate salt, 2-naphthalenesulfonate salt, or edisylate salt. In certain embodiments, the Compound is in the form of a free base.

In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a free base. The Compounds described herein may be administered by any route, such as those routes described in Section 4.4.

In certain embodiments, the disease or disorder associated with an activated immune system, or a disease or disorder that can be treated and/or prevented with a selective S1P1 receptor agonist is selected from the group consisting of rejection of transplanted organs or tissue; graft-versus-host diseases brought about by transplantation; autoimmune syndromes including rheumatoid arthritis; systemic lupus erythematosus; Hashimoto's thyroiditis; lymphocytic thyroiditis; multiple sclerosis; myasthenia gravis; type I diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; coeliac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

In certain embodiments, the disease or disorder is selected from the group consisting of rejection of transplanted organs such as kidney, liver, heart, lung, pancreas, cornea, and skin; graft-versus-host disease, e.g., brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; type I diabetes; post-infectious autoimmune diseases including rheumatic fever and post-infectious glomerulonephritis; solid cancers; and tumor metastasis.

In certain embodiments, the disease or disorder is selected from the group consisting of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; post-infectious autoimmune diseases including rheumatic fever and post-infectious glomerulonephritis; and metastasis of carcinoma.

In certain embodiments, the disease or disorder is selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

In certain embodiments, the disease or disorder is selected from multiple sclerosis and psoriasis.

In certain embodiments, the disease or disorder is selected from multiple sclerosis and psoriasis.

In certain embodiments, the disease or disorder is moderate to severe chronic plaque psoriasis.

In certain embodiments, the disease multiple sclerosis.

In certain embodiments, the disease is selected from relapsing multiple sclerosis and relapsing-remitting multiple sclerosis.

In certain embodiments, the disease is relapsing multiple sclerosis.

In certain embodiments, the disease is relapsing-remitting multiple sclerosis.

Provided herein are methods for treating a subject suffering from or at risk for having a disease or disorder associated with sphingosine 1-phosphate, In certain embodiments, the method for treating a subject suffering from or at risk of having a disease or disorder associated with disease or disorder associated with sphingosine 1-phosphate comprises administering to said subject a therapeutically effective amount any combination of a Compound, or a pharmaceutically acceptable salt, hydrate, or solvate thereof.

Provided herein are methods for treating a subject suffering from or at risk for having a disease or disorder associated with sphingosine 1-phosphate, In certain embodiments, the method for treating a subject suffering from or at risk of having a disease or disorder associated with disease or disorder associated with sphingosine 1-phosphate comprises administering to said subject a therapeutically effective amount any combination of Compounds, or a pharmaceutically acceptable salt, hydrate, or solvate thereof.

In certain embodiments, the method for treating a subject suffering from or at risk having of a disease or disorder associated with sphingosine 1-phosphate comprises administering to said subject a therapeutically effective amount of a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk having of a disease or disorder associated with sphingosine 1-phosphate comprises administering to said subject a therapeutically effective amount of any combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk having of a disease or disorder associated with sphingosine 1-phosphate comprises administering to said subject a therapeutically effective amount of a pharmaceutical composition comprising a Compound or a pharmaceutically acceptable salt, solvate, or hydrate thereof.

In certain embodiments, the method for treating a subject suffering from or at risk of having a disease or disorder associated with sphingosine 1-phosphate comprises administering to said subject a therapeutically effective amount of a pharmaceutical formulation comprising a Compound or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having a disease or disorder associated with sphingosine 1-phosphate comprises administering to said subject a therapeutically effective amount of a pharmaceutical composition comprising a combination of Compounds, or a pharmaceutically acceptable salt, hydrate, or solvate thereof.

In certain embodiments, the method for treating a subject suffering from or at risk of having a disease or disorder associated with sphingosine 1-phosphate comprises administering to said subject a therapeutically effective amount of a pharmaceutical formulation comprising any combination of Compounds, or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having disease or disorder associated with sphingosine 1-phosphate comprises administering to said subject a therapeutically effective amount of a pharmaceutical composition comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having a disease or disorder associated with sphingosine 1-phosphate comprises administering to said subject a therapeutically effective amount of a pharmaceutical formulation comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the method for treating a subject suffering from or at risk of having disease or disorder associated with sphingosine 1-phosphate comprises administering to said subject a therapeutically effective amount of a pharmaceutical composition comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having a disease or disorder associated with sphingosine 1-phosphate comprises administering to said subject a therapeutically effective amount of a pharmaceutical formulation comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the Compound or any combination of Compounds in the pharmaceutical compositions and/or pharmaceutical formulations is in the form of a of hydrochloride salt, hydrobromide salt, napadisylate salt, 2-naphthalenesulfonate salt, edisylate salt, p-toluenesulfonate salt, trifluoroacetate salt, or ethanesulfonate salt. In certain embodiments, the combination of Compounds is in the form of a hydrochloride salt, hydrobromide salt, napadisylate salt, 2-naphthalenesulfonate salt, or edisylate salt. In certain embodiments, the Compound is in the form of a free base.

In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a free base. The Compounds described herein may be administered by any route, such as those routes described in Section 4.4.

In certain embodiments, the disease or disorder associated with sphingosine 1-phosphate is multiple sclerosis, relapseremitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, or Graves' disease.

Provided herein are methods for treating a subject suffering from or at risk of having multiple sclerosis, wherein the method comprises administering to said subject a therapeutically effective amount of a Compound (i.e., Compound 1, Compound 1A-1F, a compound of Formula (I), a compound of Formula (II), a compound of Formula (III), a compound of Formula (IV), a compound listed in Table 1, a compound listed in Table 2, a compound listed in Table 3, or a compound listed in Table 4), or a pharmaceutically acceptable salt, hydrate, or solvate thereof.

In certain embodiments, the method for treating a subject suffering from or at risk of having multiple sclerosis comprises administering to said subject a therapeutically effective amount any combination of Compounds, or a pharmaceutically acceptable salt, hydrate, or solvates thereof.

In certain embodiments, the method for treating a subject suffering from or at risk of having multiple sclerosis comprises administering to said subject a therapeutically effective amount of a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having multiple sclerosis comprises administering to said subject a therapeutically effective amount of any combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having multiple sclerosis comprises administering to said subject a therapeutically effective amount of a pharmaceutical composition comprising a Compound or a pharmaceutically acceptable salt, solvate, or hydrate thereof.

In certain embodiments, the method for treating a subject suffering from or at risk of having multiple sclerosis comprises administering to said subject a therapeutically effective amount of a pharmaceutical formulation comprising a Compound or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having multiple sclerosis comprises administering to said subject a therapeutically effective amount of a pharmaceutical composition comprising a combination of Compounds, or a pharmaceutically acceptable salt, hydrate, or solvate thereof.

In certain embodiments, the method for treating a subject suffering from or at risk of having multiple sclerosis comprises administering to said subject a therapeutically effective amount of a pharmaceutical formulation comprising any combination of Compounds, or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having multiple sclerosis comprises administering to said subject a therapeutically effective amount of a pharmaceutical composition comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having multiple sclerosis comprises administering to said subject a therapeutically effective amount of a pharmaceutical formulation comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the method for treating a subject suffering from or at risk of having multiple sclerosis comprises administering to said subject a therapeutically effective amount of a pharmaceutical composition comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having multiple sclerosis comprises administering to said subject a therapeutically effective amount of a pharmaceutical formulation comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the Compound or any combination of Compounds in the pharmaceutical compositions and/or pharmaceutical formulations is in the form of a of hydrochloride salt, hydrobromide salt, napadisylate salt, 2-naphthalenesulfonate salt, edisylate salt, p-toluenesulfonate salt, trifluoroacetate salt, or ethanesulfonate salt. In certain embodiments, the combination of Compounds is in the form of a hydrochloride salt, hydrobromide salt, napadisylate salt, 2-naphthalenesulfonate salt, or edisylate salt. In certain embodiments, the Compound is in the form of a free base.

In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a free base.

The Compounds described herein may be administered by any route, such as those routes described in Section 4.4.

Provided herein are methods for treating a subject suffering from or at risk of having psoriasis, wherein the method comprises administering to said subject a therapeutically effective amount of a Compound (i.e., Compound 1, Compound 1A-1F, a compound of Formula (I), a compound of Formula (II), a compound of Formula (III), a compound of Formula (IV), a compound listed in Table 1, a compound listed in Table 2, a compound listed in Table 3, or a compound listed in Table 4), or a pharmaceutically acceptable salt, hydrate, or solvate thereof.

In certain embodiments, the method for treating a subject suffering from or at risk of having psoriasis comprises administering to said subject a therapeutically effective amount any combination of Compounds, or a pharmaceutically acceptable salt, hydrate, or solvates thereof.

In certain embodiments, the method for treating a subject suffering from or at risk of having psoriasis comprises administering to said subject a therapeutically effective amount of a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having psoriasis comprises administering to said subject a therapeutically effective amount of any combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having psoriasis comprises administering to said subject a therapeutically effective amount of a pharmaceutical composition comprising a Compound or a pharmaceutically acceptable salt, solvate, or hydrate thereof.

In certain embodiments, the method for treating a subject suffering from or at risk of having psoriasis comprises administering to said subject a therapeutically effective amount of a pharmaceutical formulation comprising a Compound or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having psoriasis comprises administering to said subject a therapeutically effective amount of a pharmaceutical composition comprising a combination of Compounds, or a pharmaceutically acceptable salt, hydrate, or solvate thereof.

In certain embodiments, the method for treating a subject suffering from or at risk of having psoriasis comprises administering to said subject a therapeutically effective amount of a pharmaceutical formulation comprising any combination of Compounds, or a pharmaceutically acceptable salt, solvate, or hydrate thereof in combination with a pharmaceutically acceptable vehicle, carrier, diluent, or excipient, or a mixture thereof.

In certain embodiments, the method for treating a subject suffering from or at risk of having psoriasis comprises administering to said subject a therapeutically effective amount of a pharmaceutical composition comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having psoriasis comprises administering to said subject a therapeutically effective amount of a pharmaceutical formulation comprising a Compound, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the method for treating a subject suffering from or at risk of having psoriasis comprises administering to said subject a therapeutically effective amount of a pharmaceutical composition comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof.

In certain embodiments, the method for treating a subject suffering from or at risk of having psoriasis comprises administering to said subject a therapeutically effective amount of a pharmaceutical formulation comprising a combination of Compounds, or a pharmaceutically acceptable salt, hydrate, or solvate thereof, and (Z)-5-((Z)-3-chloro-4-((R)-2,3-dihydroxypropoxy)benzylidene)-2-(propylimino)-3-(o-tolyl)thiazolidin-4-one (Compound 11), or a pharmaceutically acceptable salt, hydrate, or solvate thereof in combination with a pharmaceutically acceptable vehicle, carrier, diluent, or excipient, or a mixture thereof.

In certain embodiments, the Compound or any combination of Compounds in the pharmaceutical compositions and/or pharmaceutical formulations is in the form of a of hydrochloride salt, hydrobromide salt, napadisylate salt, 2-naphthalenesulfonate salt, edisylate salt, p-toluenesulfonate salt, trifluoroacetate salt, or ethanesulfonate salt. In certain embodiments, the combination of Compounds is in the form of a hydrochloride salt, hydrobromide salt, napadisylate salt, 2-naphthalenesulfonate salt, or edisylate salt. In certain embodiments, the Compound is in the form of a free base.

In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a hydrochloride salt, hydrobromide salt, napadisylate salt, 2-naphthalenesulfonate salt, or edisylate salt. In certain embodiments, (Z)-5-((Z)-3-chloro-4-((R)-2,3-dihydroxypropoxy)benzylidene)-2-(propylimino)-3-(o-tolyl)thiazolidin-4-one (Compound 11) is in the form of a free base.

The Compounds described herein may be administered by any route, such as those routes described in Section 4.4.

In certain embodiments, the pharmaceutical compositions and formulations disclosed herein comprise a Compound, or a pharmaceutically acceptable salt, hydrate, or solvate thereof, and at least one of Compound 12A, Compound 12B, Compound 12C, and Compound 12D or a pharmaceutically acceptable salt, hydrate, or solvate thereof:

Compound 12A

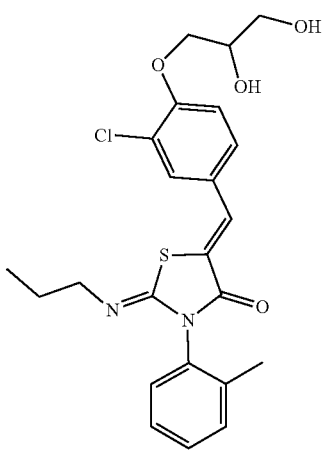

Compound 12B

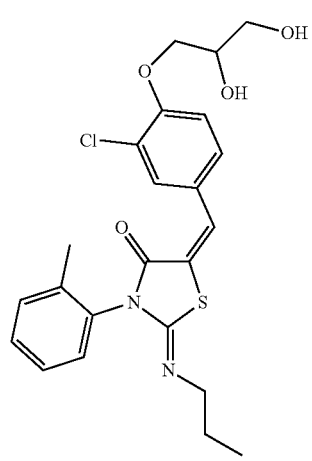

Compound 12C

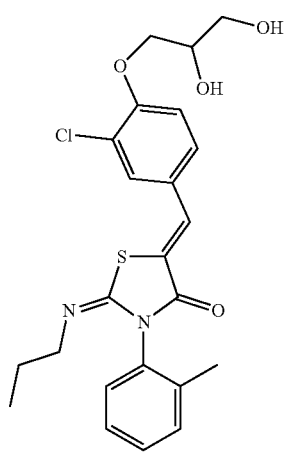

Compound 12D

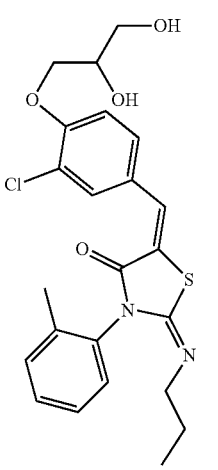

In certain embodiments, the pharmaceutical compositions and formulations disclosed herein comprise any combination of Compounds, or a pharmaceutically acceptable salt, hydrate, or solvate thereof, and at least one of Compound 12A, Compound 12B, Compound 12C, and Compound 12D, or a pharmaceutically acceptable salt, hydrate, or solvate thereof.

In certain embodiments, any of Compound 12A, Compound 12B, Compound 12C, and Compound 12D can have an R configuration, an S configuration, or mixtures thereof.

In certain embodiments, any of Compound 12A, Compound 12B, Compound 12C, and Compound 12D is in the form of a hydrobromide salt, napadisylate salt, 2-naphthalenesulfonate salt, edisylate salt, p-toluenesulfonate salt, trifluoroacetate salt, or ethanesulfonate salt. In certain embodiments, any of Compound 12A, Compound 12B, Compound 12C, and Compound 12D is in the form of a hydrochloride salt, hydrobromide salt, napadisylate salt, 2-naphthalenesulfonate salt, or edisylate salt. In certain embodiments, any of Compound 12A, Compound 12B, Compound 12C, and Compound 12D is in the form of a free base.

In certain embodiments, the pharmaceutical compositions and formulations disclosed herein comprise a Compound, or a pharmaceutically acceptable salt, hydrate, or solvate thereof, and 5-(3-chloro-4-(2,3-dihydroxypropoxy)benzylidene)-2-(propylimino)-3-(o-tolyl)thiazolidin-4-one (Compound 12), or a pharmaceutically acceptable salt, hydrate, or solvate thereof.

In certain embodiments, the pharmaceutical compositions and formulations disclosed herein comprise any combination of Compounds, or a pharmaceutically acceptable salt, hydrate, or solvate thereof, and 5-(3-chloro-4-(2,3-dihydroxypropoxy)benzylidene)-2-(propylimino)-3-(o-tolyl)thiazolidin-4-one (Compound 12), or a pharmaceutically acceptable salt, hydrate, or solvate thereof.

In certain embodiments, Compound 12 can have an R configuration, an S configuration, or mixtures thereof.

In certain embodiments, any of Compound 12 is in the form of a hydrobromide salt, napadisylate salt, 2-naphthalenesulfonate salt, edisylate salt, p-toluenesulfonate salt, trifluoroacetate salt, or ethanesulfonate salt. In certain embodiments, any of Compound 12 is in the form of a hydrochloride salt, hydrobromide salt, napadisylate salt, 2-naphthalenesulfonate salt, or edisylate salt. In certain embodiments, any of Compound 12 is in the form of a free base.

The compounds, compositions, methods, and uses disclosed herein are not to be limited in scope by the specific embodiments described herein. For example, all disclosed compounds can be in their free base form, or a pharmaceutically acceptable salt, hydrate, solvate, clathrate, prodrug, or polymorph thereof. Indeed, various modifications of the compounds, compositions, methods, and uses in addition to those described will become apparent to those skilled in the art from the foregoing description. Such modifications are intended to fall within the scope of the appended claims.

Various publications, patents and patent applications are cited herein, the disclosures of which are incorporated by reference in their entities.

5 EXAMPLES

5.1 Example 1: Synthesis of (R,Z)-5-(3-chloro-4-(2,3-dihydroxypropoxy)benzylidene)-3-(o-tolyl)thiazolidine-2,4-dione (Compound 1)

Step 1: Synthesis of 3-(o-tolyl)thiazolidine-2,4-dione (Compound 1.1)

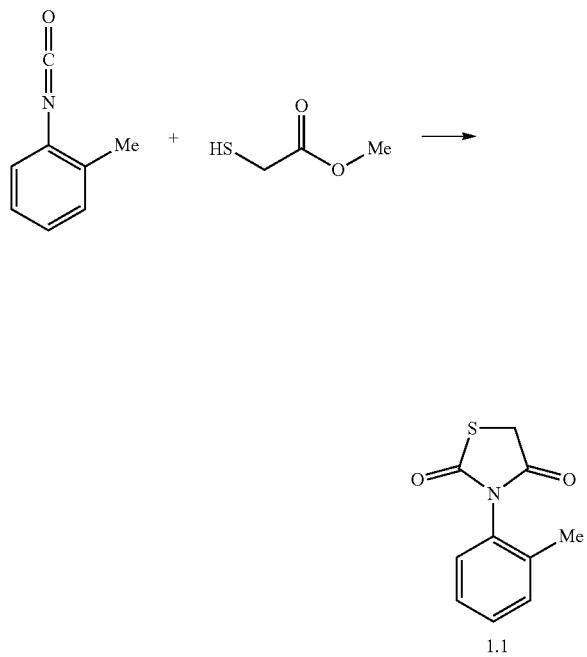

To a solution of ethyl 2-mercaptoacetate (902 mg, 7.52 mmol) in xylene (20 mL) at room temperature was added 1-isocyanato-2-methylbenzene (1.0 g, 7.52 mmol) and sodium (10 mg, 0.32 mmol). Reaction mixture was heated to 130° C. for 48 h. The reaction mixture was quenched with 1M aq. HCl and extracted with $CH_2Cl_2$. The combined organic fractions were dried ($MgSO_4$) concentrated in vacuo and loaded onto a 24 g $SiO_2$ ISCO column eluted with EtOAc/Hexane (0 to 30%). The pure fractions were combined and concentrated to afford Compound 1.1 (1.1 g, 70% yield) as a light yellow solid. $^1$H-NMR (500 MHz; $CDCl_3$): δ 7.42-7.28 (m, 3H), 7.12 (d, J=7.8 Hz, 1H), 4.18-4.10 (m, 3H), 2.19 (s, 3H). LRMS (ESI): m/z calc. for $C_{10}H_9NO_2S$ [M+H]$^+$: 207.04; found 208.06.

Step 2: (R,Z)-5-(3-chloro-4-(2,3-dihydroxypropoxy)benzylidene)-3-(o-tolyl)thiazolidine-2,4-dione (Compound 1B)

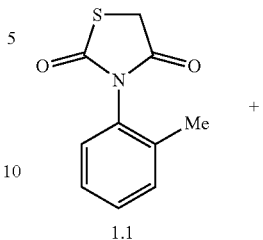

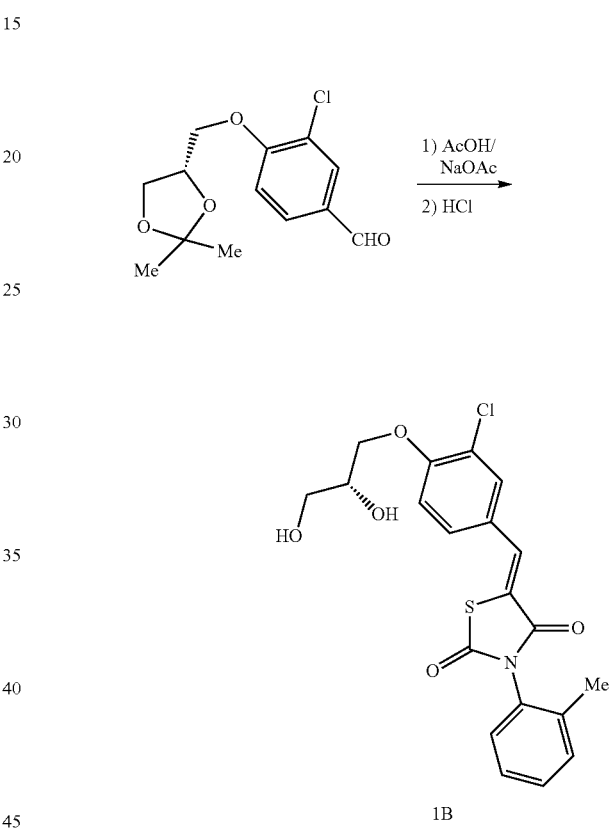

A reaction vial was charged with Compound 1.1 (100 mg, 0.483 mmol) and AcOH (2 mL). (S)-3-chloro-4-((2,2-dimethyl-1,3-dioxolan-4-yl)methoxy)benzaldehyde (143 mg, 0.53 mmol) was added. The reaction mixture was heated to 120° C. for 16 h. The resulting solution was loaded directly onto a 150 g C18 Aq Isco column and eluted with ACN/$H_2O$ containing 0.05% AcOH (0 to 100% ACN). The fractions containing product were combined and lyophilized to afford Compound 1, 14 mg, 7% yield, as a white solid. $^1$H-NMR (300 MHz; DMSO-$d_6$): δ 7.99 (s, 1H), 7.83 (d, J=2.0 Hz, 1H), 7.64 (dd, J=8.7, 2.0 Hz, 1H), 7.42 (d, J=9.8 Hz, 4H), 5.06 (d, J=4.5 Hz, 1H), 4.78-4.69 (m, 1H), 4.26-4.03 (m, 3H), 3.94-3.81 (m, 1H), 3.56-3.44 (m, 2H). $^{13}$C-NMR (75 MHz; DMSO-$d_6$): δ166.7, 165.3, 156.3, 136.4, 132.7, 131.3, 130.6, 130.3, 129.4, 127.5, 126.8, 122.7, 120.1, 114.9, 71.2, 70.2, 62.9, 17.4 LRMS (ESI): m/z calc. for $C_{20}H_{18}ClNO_5S$ [M+H]$^+$: 419.06; found 420.0. HRMS (ESI): m/z calc. for $C_{20}H_{18}ClNO_5S$ [M+Na]$^+$: 442.0594; found 442.0492.

5.2 Example 2: Synthesis of (Z)-2-(3-chloro-4-((R)-2,3-dihydroxypropoxy)phenyl)-5-(propylimino)-6-(o-tolyl)-1-oxa-4-thia-6-azaspiro[2.4]heptan-7-one (Compound 4B)

5.3 Example 3: Synthesis of (Z)-5-((Z)-3-chloro-4-((R)-2,3-dihydroxypropoxy)benzylidene)-2-(propylimino)-3-(o-tolyl)thiazolidin-4-one 1-oxide (Compound 5B)

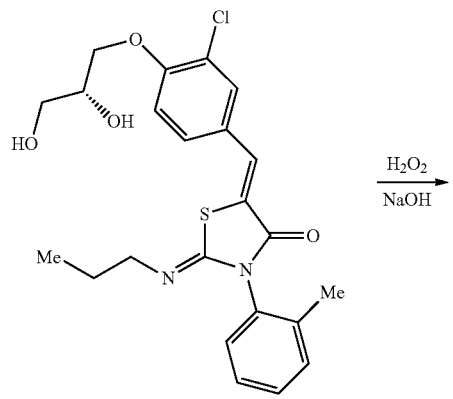

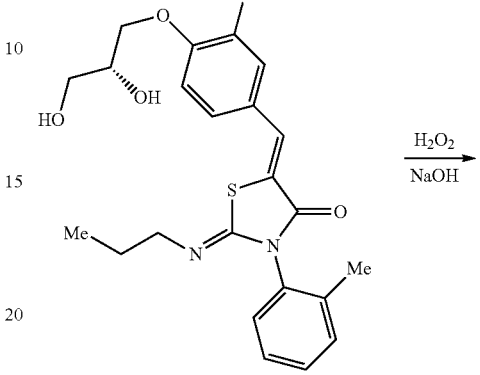

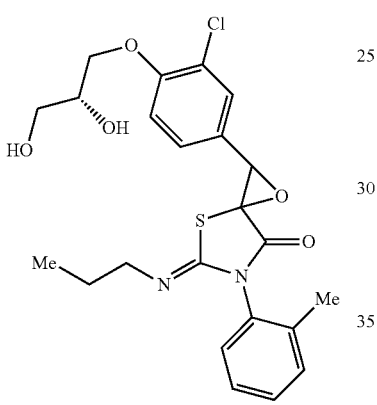

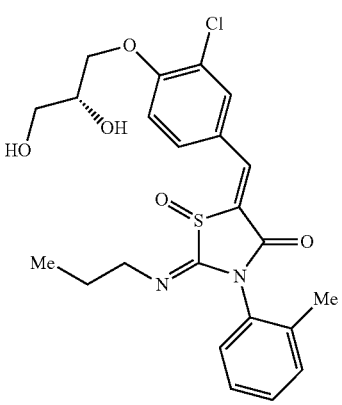

A vial was charged with Compound 11 (200 mg, 0.43 mmol) and Acetone/MeOH (3:1) (4 mL). The solution was cooled to 0° C., then 1M aq. NaOH (0.1 mL, 1.0 mmol) was added. After stirring for 5 minutes, 36% $H_2O_2$ (2.8 mL, 1.3 mmol) was added dropwise over 1 h. The reaction was stirred at 0° C. for 5 h, then stored at −20° C. overnight (18 hours). The reaction was concentrated in vacuo. The residue was taken up in DMF loaded directly onto a 150 g C18 Aq Isco column and eluted with ACN/$H_2O$ containing 0.05% AcOH (0 to 100%). The fractions containing product were combined and lyophilized to afford the product Compound 4, 60 mg, 20% yield, as a white fluffy solid. $^1$H-NMR (300 MHz; DMSO-$d_6$): δ 7.42 (d, J=1.2 Hz, 1H), 7.21 (t, J=8.8 Hz, 1H), 7.18-7.11 (m, 3H), 7.07-7.02 (m, 1H), 6.79 (d, J=7.4 Hz, 1H), 4.98 (d, J=5.1 Hz, 1H), 4.87 (s, 1H), 4.68 (t, J=5.4 Hz, 1H), 4.09-3.91 (m, 2H), 3.91-3.76 (m, 3H), 3.51-3.43 (m, 2H), 2.52 (t, J=1.7 Hz, 1H), 1.77 (sextet, J=7.3 Hz, 2H), 1.19 (t, J=7.1 Hz, 1H), 0.97 (q, J=8.6 Hz, 3H). $^{13}$C NMR (75 MHz; DMSO-$d_6$): δ 168.3, 155.2, 149.5, 146.6, 131.1, 129.6, 128.6, 127.2, 126.1, 125.7, 125.4, 122.0, 119.9, 114.3, 74.2, 70.9, 70.2, 63.0, 61.8, 45.0, 20.7, 17.8, 11.6. LRMS (ESI): m/z calc. for $C_{23}H_{25}ClN_2O_5S$ [M+H]$^+$: 477.12; found 477.31. HRMS (ESI): m/z calc. for $C_{23}H_{25}ClN_2O_5S$ [M+Na]$^+$: 499.1173; found 499.1069.

A reaction vial was charged with Compound 11 (50 mg, 0.11 mmol) and Acetone/MeOH (3:1) (2 mL). The solution was cooled to 0° C., then 1 M Aq NaOH (0.03 mL, 0.3 mmol) was added. After stirring for 5 minutes, 36% $H_2O_2$ (0.7 mL, 0.32 mmol) was added dropwise over 1 h. The reaction was stirred at 0° C. for 5 h, then an additional 36% $H_2O_2$ (0.7 mL, 0.32 mmol) was added all at once. The reaction mixture was stored at −20° C. overnight (18 hours). The reaction was concentrated in vacuo. The residue was taken up in DMF loaded directly onto a 150 g C18 Aq Isco column and eluted with ACN/$H_2O$ containing 0.05% AcOH (0 to 100%). The fractions containing product were combined and lyophilized to afford the product Compound 5, 10 mg, 20% yield, as a white fluffy solid. $^1$H-NMR (500 MHz; CDCl$_3$): δ 7.68 (d, J=2.2 Hz, 1H), 7.47 (dd, J=8.7, 2.2 Hz, 1H), 7.22 (t, J=7.3 Hz, 1H), 7.10-7.07 (m, 1H), 6.92 (d, J=8.7 Hz, 1H), 6.79 (d, J=7.5 Hz, 1H), 4.34-4.30 (m, 2H), 4.18-4.10 (m, 4H), 3.90-3.81 (m, 2H), 3.66 (t, J=4.8 Hz, 1H), 2.21 (s, 1H), 2.15 (s, 3H), 1.87 (sextet, J=7.6 Hz, 2H), 1.59 (s, 2H), 1.28 (t, J=7.0 Hz, 2H), 1.04 (q, J=7.0 Hz, 4H). $^{13}$C NMR (75 MHz; DMSO-$d_6$): δ 161.1, 155.0, 146.4, 146.2, 135.0, 131.3, 130.2, 128.9, 128.6, 127.5, 125.8, 124.8, 121.8, 120.5, 114.2, 113.3, 71.0, 70.25, 70.14, 62.9, 46.0, 29.5, 20.4, 17.8. LRMS (ESI): m/z calc. for $C_{23}H_{25}ClN_2OS$ [M+H]$^+$: 477.12; found 477.27. HRMS (ESI): m/z calc. for $C_{23}H_{25}ClN_2O_5S$ [M+Na]$^+$: 499.1173; found 499.1058.

5.4 Example 4: Synthesis of (Z)-5-((Z)-3-chloro-4-(3-hydroxy-2-oxopropoxy)benzylidene)-2-(propylimino)-3-(o-tolyl)thiazolidin-4-one (Compound 7A)

Step 1: Synthesis of (Z)-5-((Z)-4-((S)-3-((tert-butyldimethylsilyl)oxy)-2-hydroxypropoxy)-3-chlorobenzylidene)-2-(propylimino)-3-(o-tolyl)thiazolidin-4-one (Compound 7.1)

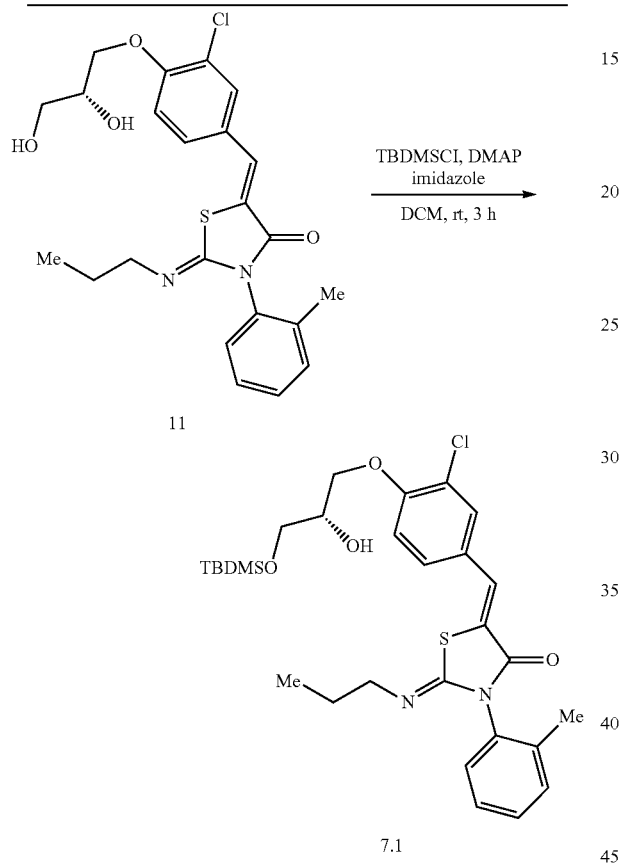

Step 2: Synthesis of (Z)-5-((Z)-4-(3-((tert-butyldimethylsilyl)oxy)-2,2-dihydroxypropoxy)-3-chlorobenzylidene)-2-(propylimino)-3-(o-tolyl)thiazolidin-4-one (Compound 7.2-hydrate)

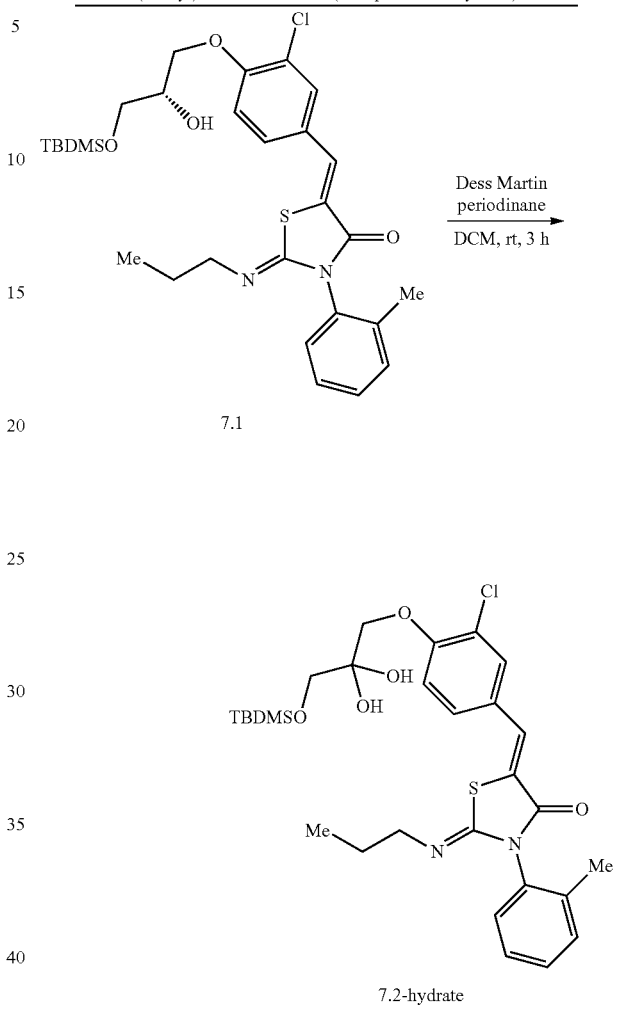

To a solution of Compound 11 (16.8 mg, 0.0365 mmol) and imidazole (5 mg, 0.073 mmol), DMAP (4.5 mg, 0.0365 mmol) in anhydrous DCM (2 mL) was added TBDMS-Cl (11 mg, 0.073 mmol). The resulting solution was stirred at room temperature. The reaction completed after 3 h by LC/MS. The reaction was quenched by addition of water. The combined organic phase was separated and dried (Na$_2$SO$_4$) and concentrated in vacuo. The residue was loaded onto a 12 g SiO$_2$ ISCO column and eluted with EtOAc in hexanes (0-50%). Combined fractions were concentrated to afford (Z)-5-((Z)-4-((S)-3-((tert-butyldimethylsilyl)oxy)-2-hydroxypropoxy)-3-chlorobenzylidene)-2-(propylimino)-3-(o-tolyl)thiazolidin-4-one (Compound 7.1), 20.1 mg, 96% yield, as a white solid. $^1$H-NMR (500 MHz; CDCl$_3$): δ 7.69 (s, 1H), 7.63 (d, J=1.9 Hz, 1H), 7.48 (dd, J=8.5, 1.9 Hz, 1H), 7.37-7.32 (m, 3H), 7.28 (s, 1H), 7.20 (d, J=7.4 Hz, 1H), 7.07 (d, J=8.6 Hz, 1H), 4.18-4.11 (m, 3H), 3.87 (d, J=3.9 Hz, 2H), 3.44-3.36 (m, 2H), 2.59 (d, J=5.4 Hz, 1H), 2.21 (s, 3H), 1.67-1.58 (m, 1H), 0.94 (d, J=7.7 Hz, 13H), 0.11 (d, J=4.1 Hz, 6H). LRMS (ESI): m/z calc. for $C_{29}H_{39}ClN_2O_4SSi$ [M+H]$^+$: 575.21; found 575.2.

To a solution of (Z)-5-((Z)-4-((S)-3-((tert-butyldimethylsilyl)oxy)-2-hydroxypropoxy)-3-chlorobenzylidene)-2-(propylimino)-3-(o-tolyl)thiazolidin-4-one (Compound 7.1; 30 mg, 0.0522 mmol) in DCM (3 mL) was added Dess-Martin reagent (0.3 M in DCM, 0.26 mL, 0.0782 mmol). After string at room temperature for 3 h, the reaction was quenched by addition of water, and extracted with DCM. The combined organic fractions were dried (MgSO$_4$) and concentrated in vacuo. The residue was loaded onto a 12 g SiO$_2$ ISCO column and eluted with EtOAc in hexanes (5-50%) The combined fractions were concentrated to afford (Z)-5-((Z)-4-(3-((tert-butyldimethylsilyl)oxy)-2,2-dihydroxypropoxy)-3-chlorobenzylidene)-2-(propylimino)-3-(o-tolyl)thiazolidin-4-one (Compound 7.2-hydrate), 24.2 mg, 81% yield, as a white solid. $^1$H-NMR (500 MHz; CDCl$_3$): δ 7.68-7.66 (m, 2H), 7.68-7.66 (m, 2H), 7.46 (dd, J=8.5, 2.0 Hz, 1H), 7.46 (dd, J=8.5, 2.0 Hz, 1H), 7.37-7.28 (m, 2H), 7.20 (d, J=7.4 Hz, 1H), 7.20 (d, J=7.4 Hz, 1H), 6.87 (d, J=8.6 Hz, 1H), 6.87 (d, J=8.6 Hz, 1H), 5.02 (s, 2H), 4.54 (s, 2H), 3.44-3.36 (m, 2H), 2.21 (s, 3H), 1.63 (td, J=7.1, 2.2 Hz, 2H), 1.55 (s, 1H), 0.98 (s, 9H), 0.93 (t, J=7.4 Hz, 3H), 0.16 (s, 6H). LRMS (ESI): m/z calc. for $C_{29}H_{39}ClN_2O_5SSi$ [M+H]$^+$: 592.2; found 592.2.

Step 3: Synthesis of (Z)-5-((Z)-3-chloro-4-(3-hydroxy-2-oxopropoxy)benzylidene)-2-(propylimino)-3-(o-tolyl)thiazolidin-4-one (Compound 7)

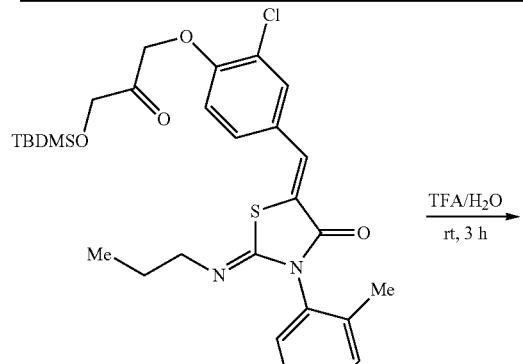

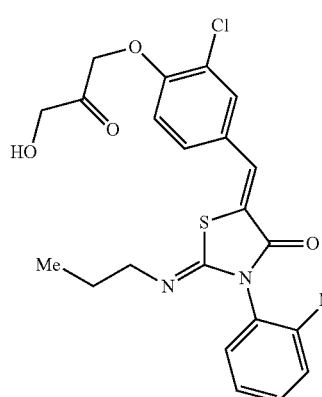

7-hydrate

A solution of (Z)-5-((Z)-4-(3-((tert-butyldimethylsilyl)oxy)-2-oxopropoxy)-3-chlorobenzylidene)-2-(propylimino)-3-(o-tolyl)thiazolidin-4-one (Compound 7.2; 38 mg, 0.0663 mmol) in TFA (0.9 mL) and water (0.1 mL) was stirred at room temperature for 1 h. The reaction was quenched by addition of saturated aqueous NaHCO$_3$ and extracted with EtOAc. The combined organic fractions were dried (MgSO$_4$ and concentrated in vacuo. The residue was loaded onto a 12 g SiO$_2$ ISCO column and eluted with EtOAc in hexanes (eluent: 5% to 60% EtOAc in hexanes) which was further purified by reverse phase pHPLC (Gemini 5 mm, C18 110A, 30×150 mm, eluent: 20-95% ACN in water AcOH 0.05%) to afford Compound 7 (as a mixture of ketone and hydrate) 24 mg, 80% yield as a white fluffy solid.

$^1$H-NMR (300 MHz; CDCl$_3$): δ 7.72-7.64 (m, 2H), 7.53-7.44 (m, 1H), 7.42-7.31 (m, 3H), 7.20 (t, J=6.7 Hz, 1H), 6.98-6.96 (m, 1H), 4.81-4.79 (m, 2H), 4.76-4.71 (m, 2H), 3.50-3.34 (m, 2H), 3.00 (t, J=5.0 Hz, 1H), 2.19 (d, J=0.8 Hz, 3H), 1.72-1.58 (m, 3H), 0.97-0.90 (m, 3H). $^{13}$C NMR (75 MHz; CDCl$_3$): δ 206.1, 166.0, 153.5, 146.7, 136.2, 134.4, 131.8, 131.1, 129.9, 129.5, 129.3, 128.6, 127.8, 127.1, 124.0, 121.5, 113.3, 111.4, 72.1, 67.1, 55.5, 23.7, 17.7, 11.8. LRMS (ESI): m/z calc. for C$_{23}$H$_{23}$ClN$_2$O$_4$S [M+H]$^+$: 459.11; found 459.1. HRMS (ESI): m/z calc. for C$_{23}$H$_{25}$ClN$_2$O$_5$S [M+H]$^+$: 477.1173; found 477.1257.

5.5 Example 5: Synthesis of (E)-3-(2-chloro-4-((Z)—((Z)-4-oxo-2-(propylimino)-3-(o-tolyl)thiazolidin-5-ylidene)methyl)phenoxy)acrylic Acid (Compound 10A)

Step 1: Synthesis of (Z)-5-((Z)-3-chloro-4-hydroxybenzylidene)-2-(propylimino)-3-(o-tolyl)thiazolidin-4-one (Compound 10.1)

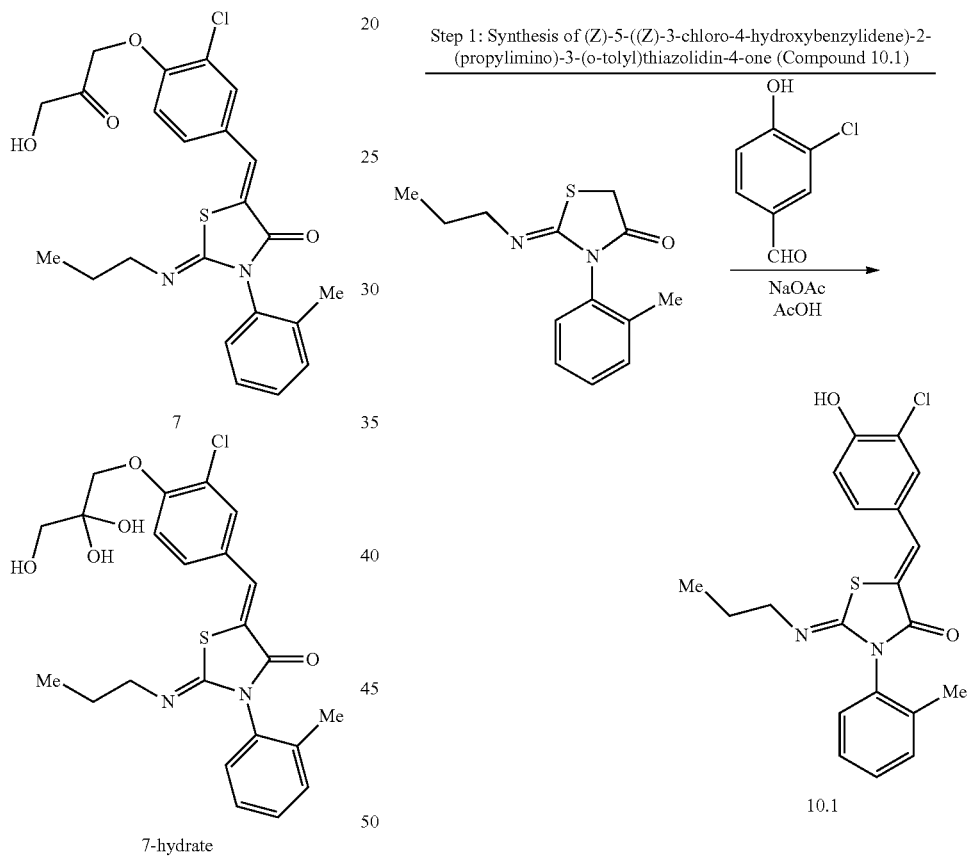

A round-bottom flask was charged with (Z)-2-(propylimino)-3-(o-tolyl)thiazolidin-4-one (300 mg, 1.20 mmol), 3-chloro-4-hydroxybenzaldehyde (189 mg, 2.4 mmol) and sodium acetate (198 mg, 2.04 mmol). The flask was sealed with a septum and flushed with argon. AcOH (6 mL) was added via syringe and the mixture was heated to 85° C. overnight. After cooling to room temperature, a precipitate formed. Et$_2$O (180 mL) was added and the resulting slurry was stirred for 3 min. Water (80 mL) was added and solids dissolved. Layers were separated, the organic layer was washed with water (80 mL), aq. saturated NaHCO$_3$(80 mL), water (80 mL, twice) and brine (50 mL). The combined organic layers were dried (MgSO$_4$) and concentrate. The residue was treated with MeOH (12 mL) and heated at 75° C. for 10 min to dissolve all solids. The mixture was set aside to cool down. The precipitate formed was collected through filtration and washed with MeOH (5 mL). The precipitate was air dried to give the product (175 mg, 37%) as a slightly yellow powder. The mother liquor was concentrated and loaded onto a 24 g ISCO column eluting with EtOAc/Hexane (0 to 40%). The pure fractions were combined and concentrated to afford the product (160 mg, 34% yield). The combined yield of (Z)-5-((Z)-3-chloro-4-hydroxybenzylidene)-2-(propylimino)-3-(o-tolyl)thiazolidin-4-one (Compound 10.1) was 335 mg, 71% yield, as a yellow solid. $^1$H-NMR (500 MHz; CDCl$_3$): δ 7.66 (s, 1H), 7.57 (d, J=1.6 Hz, 1H), 7.43 (dd, J=8.5, 1.6 Hz, 1H), 7.34-7.30 (m, 3H), 7.18 (d, J=7.4 Hz, 1H), 7.11 (d, J=8.5 Hz, 1H), 5.91 (s, 1H), 3.44-3.33 (m, 2H), 2.19 (s, 3H), 1.62 (qd, J=7.4, 1.8 Hz, 2H), 0.92 (t, J=7.4 Hz, 3H). LRMS (ESI): m/z calc. for C$_{20}$H$_{20}$ClN$_2$O$_2$S [M+H]$^+$: 387.09; found 387.10.

Step 2: Synthesis of tert-Butyl (E)-3-(2-chloro-4-((Z)-((Z)-4-oxo-2-(propylimino)-3-(o-tolyl)thiazolidin-5-ylidene)methyl) phenoxy)acrylate (Compound 10.2)

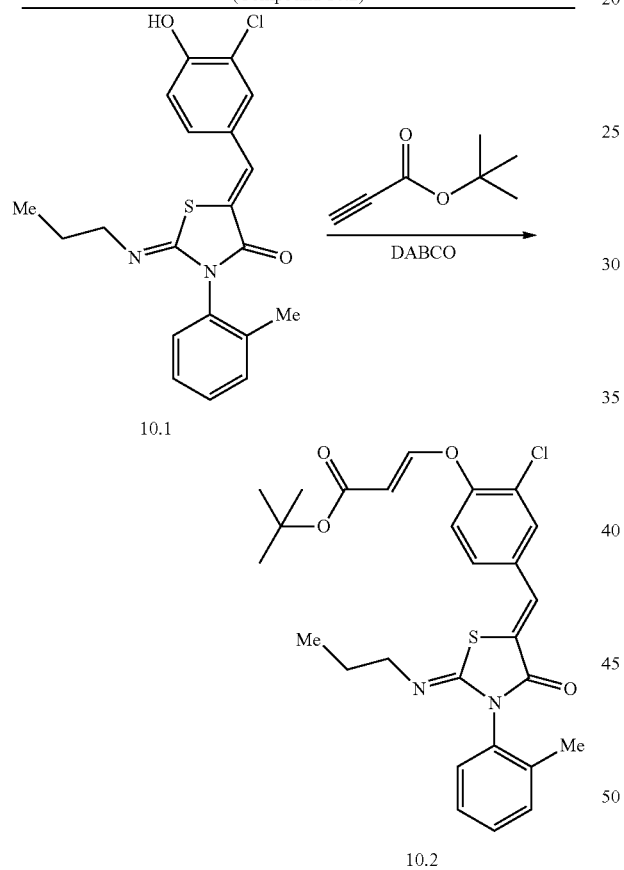

10.1

10.2

A reaction vial was charged with (Z)-5-((Z)-3-chloro-4-hydroxybenzylidene)-2-(propylimino)-3-(o-tolyl)thiazolidin-4-one (Compound 10.1; 60 mg, 0.155 mmol) and DABCO (2 mg, 0.015 mmol). The tube was sealed and flushed with argon. Dry THF (1.5 mL) was added and the resulting solution was stirred at room temperature. In a separate vial tert-butyl propiolate (60 μL) was charged with dry THF (400 μL) under argon. 200 μL of the resulting solution was charged to the reaction mixture over 10 min at room temperature. After 1 h the mixture was diluted with DCM (10 mL) and SiO$_2$ was added. The solvents were removed under vacuum and the adsorbed product was purified by 12 g ISCO SiO$_2$ column eluting with EtOAc in hexane (0 to 40%) to afford tert-Butyl (E)-3-(2-chloro-4-((Z)—((Z)-4-oxo-2-(propylimino)-3-(o-tolyl)thiazolidin-5-ylidene)methyl) phenoxy)acrylate (Compound 10.2) 65 mg; 82% yield as a colorless film. $^1$H-NMR (500 MHz; CDCl$_3$): δ 7.66 (m, 3H), 7.50 (dd, J=8.5, 1.8 Hz, 1H), 7.36-7.31 (m, 3H), 7.22 (d, J=8.5 Hz, 1H), 7.19 (d, J=7.4 Hz, 1H), 5.51 (d, J=12.2 Hz, 1H), 3.45-3.33 (m, 2H), 2.19 (s, 3H), 1.63 (qd, J=7.4, 2.1 Hz, 2H), 1.50 (s, 9H), 0.92 (t, J=7.4 Hz, 3H). LRMS (ESI): m/z calc. for C$_{27}$H$_{30}$ClN$_2$O$_4$S [M+H]$^+$: 513.16; found 513.38.

Step 3: Synthesis of (E)-3-(2-chloro-4-((Z)-((Z)-4-oxo-2-(propylimino)-3-(o-tolyl)thiazolidin-5-ylidene)methyl)phenoxy)acrylic acid (Compound 10A)

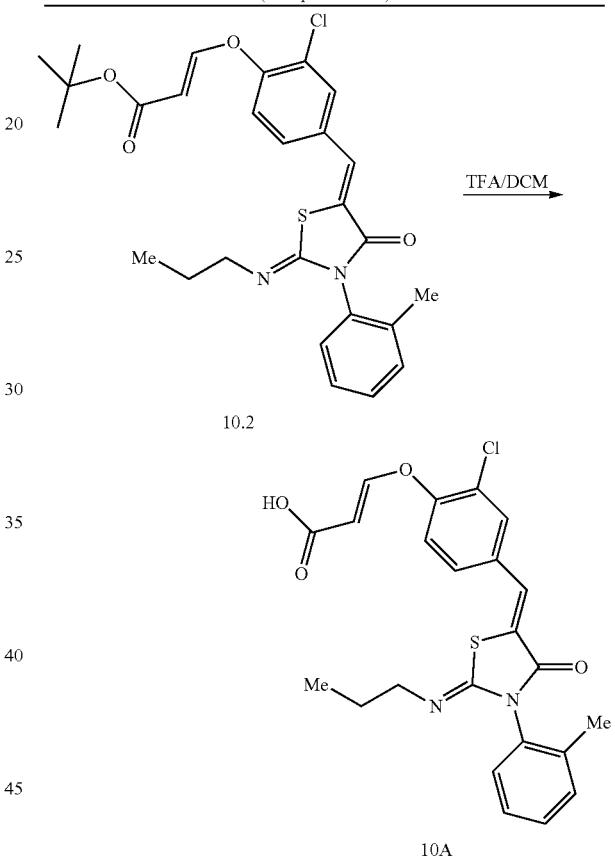

10.2

10A

A round-bottom flask was charged with a solution of tert-Butyl (E)-3-(2-chloro-4-((Z)—((Z)-4-oxo-2-(propylimino)-3-(o-tolyl)thiazolidin-5-ylidene)methyl) phenoxy)acrylate (Compound 10.2; 40 mg, 0.078 mmol) in dry DCM (2 mL). The solution was cooled in ice/water bath. TFA (2 mL) was added dropwise and the mixture was stirred at 0° C. After 3 h the mixture was concentrated to dryness to give a slightly yellow film. The residue was adsorbed on SiO$_2$ and purified by 12 g ISCO SiO$_2$ column eluting with EtOAc in hexane (0 to 60%). Fractions containing product were combined and evaporated to afford Compound 10, 36 mg; 83% yield, as a white powder. $^1$H-NMR (500 MHz; DMSO-d$_6$): δ 12.29 (broad s, 1H), 7.92 (s, 1H), 7.83 (d, J=12.1 Hz, 1H), 7.77 (s, 1H), 7.72 (d, J=8.5 Hz, 1H), 7.58 (d, J=8.4 Hz, 1H), 7.39 (s, 2H), 7.34-7.28 (m, 2H), 5.54 (d, J=12.1 Hz, 1H), 3.36-3.26 (m, 2H), 2.09 (s, 3H), 1.52 (q, J=6.8 Hz, 2H), 0.84 (t, J=7.2 Hz, 3H). $^{13}$C-NMR (75 MHz; DMSO-d$_6$): δ 166.9, 165.0, 157.6, 151.2, 146.1, 135.8, 134.6, 132.1, 131.7, 130.6, 129.7, 129.12, 129.00, 127.2, 126.8, 124.1, 122.3, 120.2, 104.2, 54.4, 23.3, 17.1, 11.7 ppm. HRMS (ESI): m/z calc. for $C_{23}H_{22}ClN_2O_4S$ $[M+H]^+$: 457.0983; found 457.0962.

What is claimed is:

1. A compound selected from the group consisting of:
(5-(3-chloro-4-(2,3-dihydroxypropoxy)benzylidene)-3-(o-tolyl)thiazolidine-2,4-dione) (Compound 1);
±(Z)-5-(3-chloro-4-(2,3-dihydroxypropoxy)benzylidene)-3-(o-tolyl)thiazolidine-2,4-dione (Compound 1A);
(R,Z)-5-(3-chloro-4-(2,3-dihydroxypropoxy)benzylidene)-3-(o-tolyl)thiazolidine-2,4-dione (Compound 1B);
(S,Z)-5-(3-chloro-4-(2,3-dihydroxypropoxy)benzylidene)-3-(o-tolyl)thiazolidine-2,4-dione (Compound 1C);
±(E)-5-(3-chloro-4-(2,3-dihydroxypropoxy)benzylidene)-3-(o-tolyl)thiazolidine-2,4-dione (Compound 1D);
(R,E)-5-(3-chloro-4-(2,3-dihydroxypropoxy)benzylidene)-3-(o-tolyl)thiazolidine-2,4-dione (Compound 1E); and
(S,E)-5-(3-chloro-4-(2,3-dihydroxypropoxy)benzylidene)-3-(o-tolyl)thiazolidine-2,4-dione (Compound 1F);
or a pharmaceutically acceptable salt, hydrate, or solvate thereof.

2. A compound of Formula (IA) or Formula (IB):

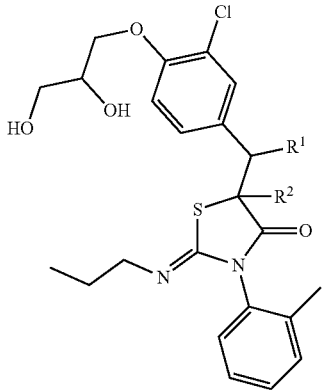

Formula (IA)

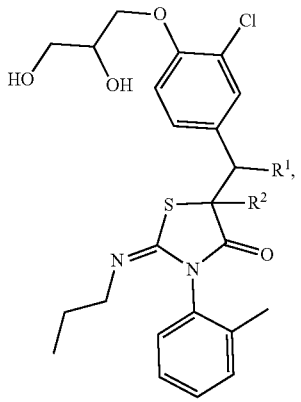

Formula (IB)

or a pharmaceutically acceptable salt, hydrate, or solvate thereof, wherein:
$R^1$ is =O or —OH; and
$R^2$ is —H; or
wherein $R^1$ and $R^2$ combine to form an epoxide ring with the carbon atoms to which they are attached.

3. The compound of claim 2, wherein the compound is selected from the group consisting of:
5-((3-chloro-4-(2,3-dihydroxypropoxy)phenyl)(hydroxy)methyl)-2-(propylimino)-3-(o-tolyl)thiazolidin-4-one;
(Z)-5-((3-chloro-4-((±)-2,3-dihydroxypropoxy)phenyl)(hydroxy)methyl)-2-(propylimino)-3-(o-tolyl)thiazolidin-4-one;
(Z)-5-((3-chloro-4-((R)-2,3-dihydroxypropoxy)phenyl)(hydroxy)methyl)-2-(propylimino)-3-(o-tolyl)thiazolidin-4-one;
(Z)-5-((3-chloro-4-((S)-2,3-dihydroxypropoxy)phenyl)(hydroxy)methyl)-2-(propylimino)-3-(o-tolyl)thiazolidin-4-one;
(E)-5-((3-chloro-4-((±)-2,3-dihydroxypropoxy)phenyl)(hydroxy)methyl)-2-(propylimino)-3-(o-tolyl)thiazolidin-4-one;
(E)-5-((3-chloro-4-((R)-2,3-dihydroxypropoxy)phenyl)(hydroxy)methyl)-2-(propylimino)-3-(o-tolyl)thiazolidin-4-one;
(E)-5-((3-chloro-4-((S)-2,3-dihydroxypropoxy)phenyl)(hydroxy)methyl)-2-(propylimino)-3-(o-tolyl)thiazolidin-4-one;
5-(3-chloro-4-(2,3-dihydroxypropoxy)benzoyl)-2-(propylimino)-3-(o-tolyl)thiazolidin-4-one;
(Z)-5-(3-chloro-4-((±)-2,3-dihydroxypropoxy)benzoyl)-2-(propylimino)-3-(o-tolyl)thiazolidin-4-one;
(Z)-5-(3-chloro-4-((R)-2,3-dihydroxypropoxy)benzoyl)-2-(propylimino)-3-(o-tolyl)thiazolidin-4-one;
(Z)-5-(3-chloro-4-((S)-2,3-dihydroxypropoxy)benzoyl)-2-(propylimino)-3-(o-tolyl)thiazolidin-4-one;
(E)-5-(3-chloro-4-((±)-2,3-dihydroxypropoxy)benzoyl)-2-(propylimino)-3-(o-tolyl)thiazolidin-4-one;
(E)-5-(3-chloro-4-((R)-2,3-dihydroxypropoxy)benzoyl)-2-(propylimino)-3-(o-tolyl)thiazolidin-4-one;
(E)-5-(3-chloro-4-((S)-2,3-dihydroxypropoxy)benzoyl)-2-(propylimino)-3-(o-tolyl)thiazolidin-4-one;
2-(3-chloro-4-(2,3-dihydroxypropoxy)phenyl)-5-(propylimino)-6-(o-tolyl)-1-oxa-4-thia-6-azaspiro[2.4]heptan-7-one;
(Z)-2-(3-chloro-4-((±)-2,3-dihydroxypropoxy)phenyl)-5-(propylimino)-6-(o-tolyl)-1-oxa-4-thia-6-azaspiro[2.4]heptan-7-one;
(Z)-2-(3-chloro-4-((R)-2,3-dihydroxypropoxy)phenyl)-5-(propylimino)-6-(o-tolyl)-1-oxa-4-thia-6-azaspiro[2.4]heptan-7-one;
(Z)-2-(3-chloro-4-((S)-2,3-dihydroxypropoxy)phenyl)-5-(propylimino)-6-(o-tolyl)-1-oxa-4-thia-6-azaspiro[2.4]heptan-7-one;
(E)-2-(3-chloro-4-((±)-2,3-dihydroxypropoxy)phenyl)-5-(propylimino)-6-(o-tolyl)-1-oxa-4-thia-6-azaspiro[2.4]heptan-7-one;
(E)-2-(3-chloro-4-((R)-2,3-dihydroxypropoxy)phenyl)-5-(propylimino)-6-(o-tolyl)-1-oxa-4-thia-6-azaspiro[2.4]heptan-7-one; and
(E)-2-(3-chloro-4-((S)-2,3-dihydroxypropoxy)phenyl)-5-(propylimino)-6-(o-tolyl)-1-oxa-4-thia-6-azaspiro[2.4]heptan-7-one;
or a pharmaceutically acceptable salt, hydrate, or solvate thereof.

4. A compound of Formula (IIA), Formula (IIB), Formula (IIC), or Formula (IID):

Formula (IIA)

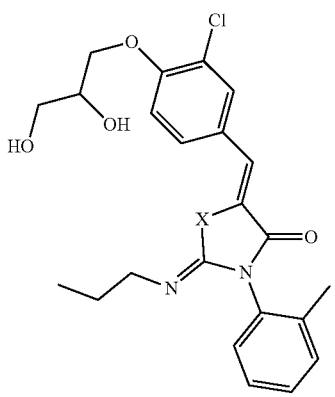

Formula (IIB)

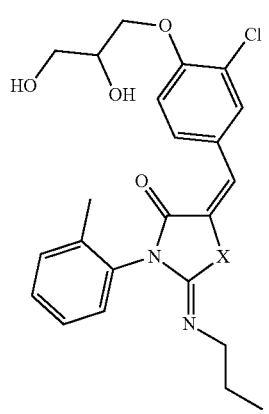

Formula (IIC)

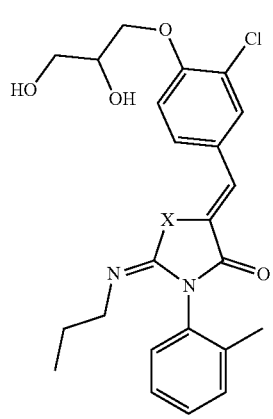

Formula (IID)

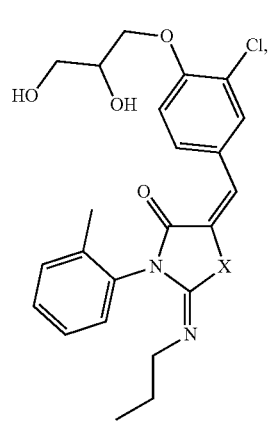

or a pharmaceutically acceptable salt, hydrate, or solvate thereof, wherein:

X is —O— or —S(O)—.

5. The compound of claim 4, wherein the compound is selected from the group consisting of:

5-(3-chloro-4-(2,3-dihydroxypropoxy)benzylidene)-2-(propylimino)-3-(o-tolyl)thiazolidin-4-one 1-oxide;

(Z)-5-((Z)-3-chloro-4-((±)-2,3-dihydroxypropoxy)benzylidene)-2-(propylimino)-3-(o-tolyl)thiazolidin-4-one 1-oxide;

(Z)-5-((Z)-3-chloro-4-((R)-2,3-dihydroxypropoxy)benzylidene)-2-(propylimino)-3-(o-tolyl)thiazolidin-4-one 1-oxide;

Z)-5-((Z)-3-chloro-4-((S)-2,3-dihydroxypropoxy)benzylidene)-2-(propylimino)-3-(o-tolyl)thiazolidin-4-one 1-oxide;

(Z)-5-((E)-3-chloro-4-((±)-2,3-dihydroxypropoxy)benzylidene)-2-(propylimino)-3-(o-tolyl)thiazolidin-4-one 1-oxide;

(Z)-5-((E)-3-chloro-4-((R)-2,3-dihydroxypropoxy)benzylidene)-2-(propylimino)-3-(o-tolyl)thiazolidin-4-one 1-oxide;

(Z)-5-((E)-3-chloro-4-((S)-2,3-dihydroxypropoxy)benzylidene)-2-(propylimino)-3-(o-tolyl)thiazolidin-4-one 1-oxide;

(E)-5-((Z)-3-chloro-4-((±)-2,3-dihydroxypropoxy)benzylidene)-2-(propylimino)-3-(o-tolyl)thiazolidin-4-one 1-oxide;

(E)-5-((Z)-3-chloro-4-((R)-2,3-dihydroxypropoxy)benzylidene)-2-(propylimino)-3-(o-tolyl)thiazolidin-4-one 1-oxide;

(E)-5-((Z)-3-chloro-4-((S)-2,3-dihydroxypropoxy)benzylidene)-2-(propylimino)-3-(o-tolyl)thiazolidin-4-one 1-oxide;

(E)-5-((E)-3-chloro-4-((±)-2,3-dihydroxypropoxy)benzylidene)-2-(propylimino)-3-(o-tolyl)thiazolidin-4-one 1-oxide;

(E)-5-((E)-3-chloro-4-((R)-2,3-dihydroxypropoxy)benzylidene)-2-(propylimino)-3-(o-tolyl)thiazolidin-4-one 1-oxide;

(E)-5-((E)-3-chloro-4-((S)-2,3-dihydroxypropoxy)benzylidene)-2-(propylimino)-3-(o-tolyl)thiazolidin-4-one 1-oxide;

5-(3-chloro-4-(2,3-dihydroxypropoxy)benzylidene)-2-(propylimino)-3-(o-tolyl)oxazolidin-4-one;

Z)-5-((Z)-3-chloro-4-((±)-2,3-dihydroxypropoxy)benzylidene)-2-(propylimino)-3-(o-tolyl)oxazolidin-4-one;

(Z)-5-((Z)-3-chloro-4-((R)-2,3-dihydroxypropoxy)benzylidene)-2-(propylimino)-3-(o-tolyl)oxazolidin-4-one;

(Z)-5-((Z)-3-chloro-4-((S)-2,3-dihydroxypropoxy)benzylidene)-2-(propylimino)-3-(o-tolyl)oxazolidin-4-one;

(Z)-5-((E)-3-chloro-4-((±)-2,3-dihydroxypropoxy)benzylidene)-2-(propylimino)-3-(o-tolyl)oxazolidin-4-one;

(Z)-5-((E)-3-chloro-4-((R)-2,3-dihydroxypropoxy)benzylidene)-2-(propylimino)-3-(o-tolyl)oxazolidin-4-one;

(Z)-5-((E)-3-chloro-4-((S)-2,3-dihydroxypropoxy)benzylidene)-2-(propylimino)-3-(o-tolyl)oxazolidin-4-one;

(E)-5-((Z)-3-chloro-4-((±)-2,3-dihydroxypropoxy)benzylidene)-2-(propylimino)-3-(o-tolyl)oxazolidin-4-one;

(E)-5-((Z)-3-chloro-4-((R)-2,3-dihydroxypropoxy)benzylidene)-2-(propylimino)-3-(o-tolyl)oxazolidin-4-one;

(E)-5-((Z)-3-chloro-4-((S)-2,3-dihydroxypropoxy)benzylidene)-2-(propylimino)-3-(o-tolyl)oxazolidin-4-one;

(E)-5-((E)-3-chloro-4-((±)-2,3-dihydroxypropoxy)benzylidene)-2-(propylimino)-3-(o-tolyl)oxazolidin-4-one;

(E)-5-((E)-3-chloro-4-((R)-2,3-dihydroxypropoxy)benzylidene)-2-(propylimino)-3-(o-tolyl)oxazolidin-4-one; and (E)-5-((E)-3-chloro-4-((S)-2,3-dihydroxypropoxy)benzylidene)-2-(propylimino)-3-(o-tolyl)oxazolidin-4-one;

or a pharmaceutically acceptable salt, hydrate, or solvate thereof.

6. A compound of Formula (IIIA), Formula (IIIB), Formula (IIIC), or Formula (IIID):

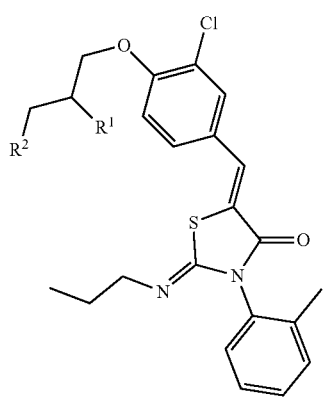

Formula (IIIA)

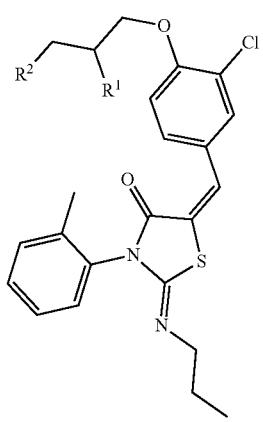

Formula (IIIB)

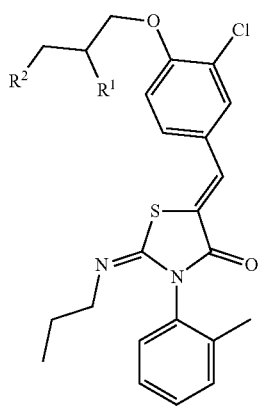

Formula (IIIC)

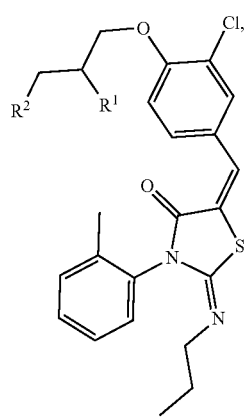

Formula (IIID)

or a pharmaceutically acceptable salt, hydrate, or solvate thereof, wherein:
one of $R^1$ or $R^2$ is —OH and the other of $R^1$ or $R^2$ is =O.

7. The compound of claim 6, wherein the compound is selected from the group consisting of:

5-(3-chloro-4-(3-hydroxy-2-oxopropoxy)benzylidene)-2-(propylimino)-3-(o-tolyl)thiazolidin-4-one;

(Z)-5-((Z)-3-chloro-4-(3-hydroxy-2-oxopropoxy)benzylidene)-2-(propylimino)-3-(o-tolyl)thiazolidin-4-one;

(Z)-5-((E)-3-chloro-4-(3-hydroxy-2-oxopropoxy)benzylidene)-2-(propylimino)-3-(o-tolyl)thiazolidin-4-one;

(E)-5-((Z)-3-chloro-4-(3-hydroxy-2-oxopropoxy)benzylidene)-2-(propylimino)-3-(o-tolyl)thiazolidin-4-one;

(E)-5-((E)-3-chloro-4-(3-hydroxy-2-oxopropoxy)benzylidene)-2-(propylimino)-3-(o-tolyl)thiazolidin-4-one;

3-(2-chloro-4-((4-oxo-2-(propylimino)-3-(o-tolyl)thiazolidin-5-ylidene)methyl)phenoxy)-2-hydroxypropanal;

(±)-3-(2-chloro-4-((Z)—((Z)-4-oxo-2-(propylimino)-3-(o-tolyl)thiazolidin-5-ylidene)methyl)phenoxy)-2-hydroxypropanal;

(S)-3-(2-chloro-4-((Z)—((Z)-4-oxo-2-(propylimino)-3-(o-tolyl)thiazolidin-5-ylidene)methyl)phenoxy)-2-hydroxypropanal;

(R)-3-(2-chloro-4-((Z)—((Z)-4-oxo-2-(propylimino)-3-(o-tolyl)thiazolidin-5-ylidene)methyl)phenoxy)-2-hydroxypropanal;

(±)-3-(2-chloro-4-((Z)—((E)-4-oxo-2-(propylimino)-3-(o-tolyl)thiazolidin-5-ylidene)methyl)phenoxy)-2-hydroxypropanal;

(S)-3-(2-chloro-4-((Z)—((E)-4-oxo-2-(propylimino)-3-(o-tolyl)thiazolidin-5-ylidene)methyl)phenoxy)-2-hydroxypropanal;

(R)-3-(2-chloro-4-((Z)—((E)-4-oxo-2-(propylimino)-3-(o-tolyl)thiazolidin-5-ylidene)methyl)phenoxy)-2-hydroxypropanal;

(±)-3-(2-chloro-4-((E)-((Z)-4-oxo-2-(propylimino)-3-(o-tolyl)thiazolidin-5-ylidene)methyl)phenoxy)-2-hydroxypropanal;

(R)-3-(2-chloro-4-((E)-((Z)-4-oxo-2-(propylimino)-3-(o-tolyl)thiazolidin-5-ylidene)methyl)phenoxy)-2-hydroxypropanal;

(S)-3-(2-chloro-4-((E)-((Z)-4-oxo-2-(propylimino)-3-(o-tolyl)thiazolidin-5-ylidene)methyl)phenoxy)-2-hydroxypropanal;

(±)-3-(2-chloro-4-((E)-((E)-4-oxo-2-(propylimino)-3-(o-tolyl)thiazolidin-5-ylidene)methyl)phenoxy)-2-hydroxypropanal;

(R)-3-(2-chloro-4-((E)-((E)-4-oxo-2-(propylimino)-3-(o-tolyl)thiazolidin-5-ylidene)methyl)phenoxy)-2-hydroxypropanal; and (S)-3-(2-chloro-4-((E)-((E)-4-oxo-2-(propylimino)-3-(o-tolyl)thiazolidin-5-ylidene)methyl)phenoxy)-2-hydroxypropanal;

or a pharmaceutically acceptable salt, hydrate, or solvate thereof.

8. A compound of Formula (IVA), Formula (IVB), Formula (IVC), Formula (IVD), Formula (IVE), Formula (IVF), Formula (IVG), or Formula (IVH):

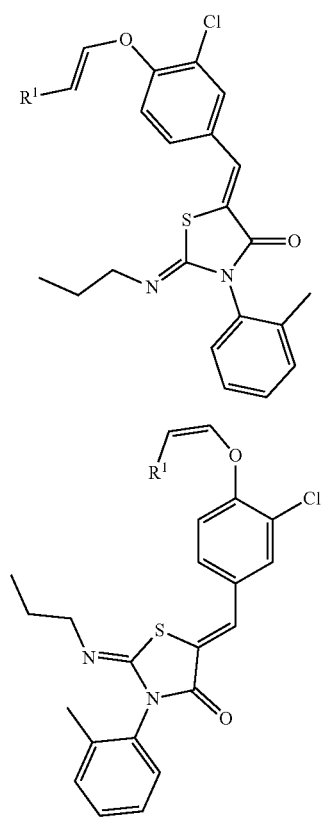

Formula (IVA)

Formula (IVB)

-continued

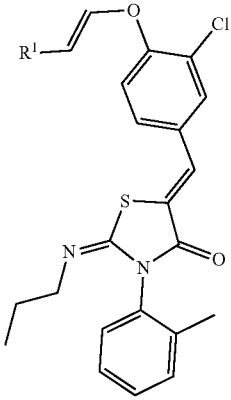

Formula (IVC)

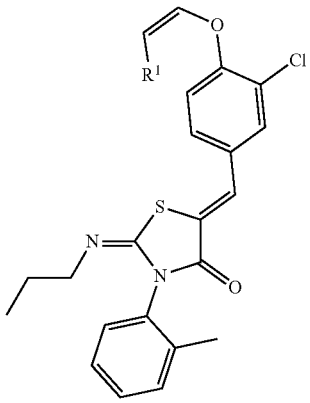

Formula (IVD)

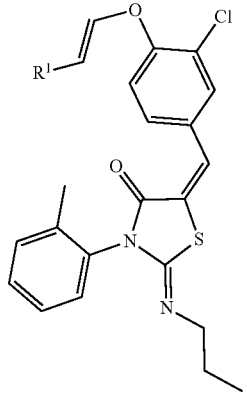

Formula (IVE)

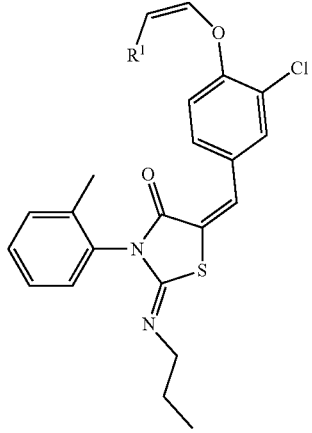

Formula (IVF)

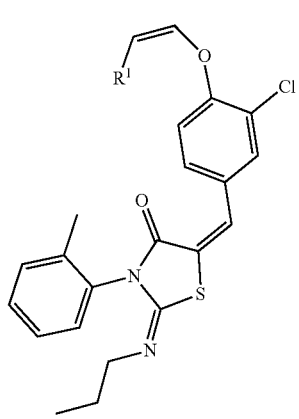

Formula (IVG)

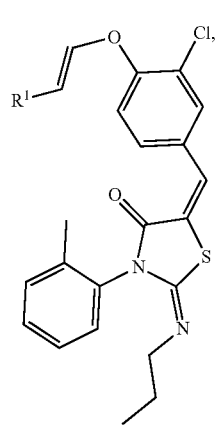

Formula (IVH)

or a pharmaceutically acceptable salt, hydrate, or solvate thereof, wherein:
R$^1$ is —C(O)H or —C(O)OH.

9. The compound of claim 8, wherein the compound is selected from the group consisting of:
3-(2-chloro-4-((4-oxo-2-(propylimino)-3-(o-tolyl)thiazolidin-5-ylidene)methyl)phenoxy)acrylaldehyde;
(E)-3-(2-chloro-4-((Z)—((Z)-4-oxo-2-(propylimino)-3-(o-tolyl)thiazolidin-5-ylidene)methyl)phenoxy)acrylaldehyde;
(Z)-3-(2-chloro-4-((Z)—((Z)-4-oxo-2-(propylimino)-3-(o-tolyl)thiazolidin-5-ylidene)methyl)phenoxy)acrylaldehyde;
(E)-3-(2-chloro-4-((Z)—((E)-4-oxo-2-(propylimino)-3-(o-tolyl)thiazolidin-5-ylidene)methyl)phenoxy)acrylaldehyde;
(Z)-3-(2-chloro-4-((Z)—((E)-4-oxo-2-(propylimino)-3-(o-tolyl)thiazolidin-5-ylidene)methyl)phenoxy)acrylaldehyde;
(E)-3-(2-chloro-4-((E)-((Z)-4-oxo-2-(propylimino)-3-(o-tolyl)thiazolidin-5-ylidene)methyl)phenoxy)acrylaldehyde;
Z)-3-(2-chloro-4-((E)-((Z)-4-oxo-2-(propylimino)-3-(o-tolyl)thiazolidin-5-ylidene)methyl)phenoxy)acrylaldehyde;
(Z)-3-(2-chloro-4-((E)-((E)-4-oxo-2-(propylimino)-3-(o-tolyl)thiazolidin-5-ylidene)methyl)phenoxy)acrylaldehyde;
(E)-3-(2-chloro-4-((E)-((E)-4-oxo-2-(propylimino)-3-(o-tolyl)thiazolidin-5-ylidene)methyl)phenoxy)acrylaldehyde;
3-(2-chloro-4-((4-oxo-2-(propylimino)-3-(o-tolyl)thiazolidin-5-ylidene)methyl)phenoxy)acrylic acid;
(E)-3-(2-chloro-4-((Z)—((Z)-4-oxo-2-(propylimino)-3-(o-tolyl)thiazolidin-5-ylidene)methyl)phenoxy)acrylic acid;
(Z)-3-(2-chloro-4-((Z)—((Z)-4-oxo-2-(propylimino)-3-(o-tolyl)thiazolidin-5-ylidene)methyl)phenoxy)acrylic acid;
(E)-3-(2-chloro-4-((Z)—((E)-4-oxo-2-(propylimino)-3-(o-tolyl)thiazolidin-5-ylidene)methyl)phenoxy)acrylic acid;
(Z)-3-(2-chloro-4-((Z)—((E)-4-oxo-2-(propylimino)-3-(o-tolyl)thiazolidin-5-ylidene)methyl)phenoxy)acrylic acid;
(E)-3-(2-chloro-4-((E)-((Z)-4-oxo-2-(propylimino)-3-(o-tolyl)thiazolidin-5-ylidene)methyl)phenoxy)acrylic acid;
(Z)-3-(2-chloro-4-((E)-((Z)-4-oxo-2-(propylimino)-3-(o-tolyl)thiazolidin-5-ylidene)methyl)phenoxy)acrylic acid;
(Z)-3-(2-chloro-4-((E)-((E)-4-oxo-2-(propylimino)-3-(o-tolyl)thiazolidin-5-ylidene)methyl)phenoxy)acrylic acid; and
(E)-3-(2-chloro-4-((E)-((E)-4-oxo-2-(propylimino)-3-(o-tolyl)thiazolidin-5-ylidene)methyl)phenoxy)acrylic acid;
or a pharmaceutically acceptable salt, hydrate, or solvate thereof.

10. A pharmaceutical composition comprising:
a. a compound of claim 1, or a pharmaceutically acceptable salt, hydrate, or solvate thereof; and
b. (Z)-5-((Z)-3-chloro-4-((R)-2,3-dihydroxypropoxy)benzylidene)-2-(propylimino)-3-(o-tolyl)thiazolidin-4-one, or a pharmaceutically acceptable salt, hydrate, or solvate thereof.

11. A pharmaceutical composition comprising:
a. a compound of claim 2, a pharmaceutically acceptable salt, hydrate, or solvate thereof, and
b. (Z)-5-((Z)-3-chloro-4-((R)-2,3-dihydroxypropoxy)benzylidene)-2-(propylimino)-3-(o-tolyl)thiazolidin-4-one, or a pharmaceutically acceptable salt, hydrate, or solvate thereof.

12. A pharmaceutical composition comprising:
a. a compound of claim 3, a pharmaceutically acceptable salt, hydrate, or solvate thereof, and
b. (Z)-5-((Z)-3-chloro-4-((R)-2,3-dihydroxypropoxy)benzylidene)-2-(propylimino)-3-(o-tolyl)thiazolidin-4-one, or a pharmaceutically acceptable salt, hydrate, or solvate thereof.

13. A pharmaceutical composition comprising:
a. a compound of claim 6, a pharmaceutically acceptable salt, hydrate, or solvate thereof, and
b. (Z)-5-((Z)-3-chloro-4-((R)-2,3-dihydroxypropoxy)benzylidene)-2-(propylimino)-3-(o-tolyl)thiazolidin-4-one, or a pharmaceutically acceptable salt, hydrate, or solvate thereof.

14. A pharmaceutical composition comprising:
a. a compound of claim 8, or a pharmaceutically acceptable salt, hydrate, or solvate thereof, and
b. (Z)-5-((Z)-3-chloro-4-((R)-2,3-dihydroxypropoxy)benzylidene)-2-(propylimino)-3-(o-tolyl)thiazolidin-4-one, or a pharmaceutically acceptable salt, hydrate, or solvate thereof.

15. A method of treating multiple sclerosis or psoriasis, wherein the method comprises administering to a patient in need thereof a compound of claim 1.

16. A method of treating multiple sclerosis or psoriasis, wherein the method comprises delivering a compound of claim 1 to a lymphocyte or lymphoid tissue of a patient in need thereof.

17. A method of treating multiple sclerosis or psoriasis, wherein the method comprises administering to a patient in need thereof a compound of claim 2.

18. A method of treating multiple sclerosis or psoriasis, wherein the method comprises administering to a patient in need thereof a compound of claim 4.

19. A method of treating multiple sclerosis or psoriasis, wherein the method comprises administering to a patient in need thereof a compound of claim 6.

20. A method of treating multiple sclerosis or psoriasis, wherein the method comprises administering to a patient in need thereof a compound of claim 8.

21. A method of treating multiple sclerosis or psoriasis, wherein the method comprises delivering a compound of claim 2 to a lymphocyte or lymphoid tissue of a patient in need thereof.

22. A method of treating multiple sclerosis or psoriasis, wherein the method comprises delivering a compound of claim 4 to a lymphocyte or lymphoid tissue of a patient in need thereof.

23. A method of treating multiple sclerosis or psoriasis, wherein the method comprises delivering a compound of claim 6 to a lymphocyte or lymphoid tissue of a patient in need thereof.

24. A method of treating multiple sclerosis or psoriasis, wherein the method comprises delivering a compound of claim 8 to a lymphocyte or lymphoid tissue of a patient in need thereof.

\* \* \* \* \*

UNITED STATES PATENT AND TRADEMARK OFFICE
CERTIFICATE OF CORRECTION

PATENT NO. : 11,014,940 B1  
APPLICATION NO. : 16/653223  
DATED : May 25, 2021  
INVENTOR(S) : Traverse et al.

Page 1 of 1

It is certified that error appears in the above-identified patent and that said Letters Patent is hereby corrected as shown below:

In the Claims

In Column 130, Line 44 (Claim 12), replace "a compound of claim 3" with "a compound of claim 4".

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*